US010342869B2

(12) United States Patent
Hann et al.

(10) Patent No.: US 10,342,869 B2
(45) Date of Patent: Jul. 9, 2019

(54) COMPOSITIONS COMPRISING ANTI-CD38 ANTIBODIES AND LENALIDOMIDE

(71) Applicants: SANOFI, Paris (FR); The Regents of the University of California, Oakland, CA (US)

(72) Inventors: Byron C. Hann, San Francisco, CA (US); Blake Tomkinson, Bridgewater, NJ (US); Thomas G. Martin, III, San Francisco, CA (US); Blake T. Aftab, San Francisco, CA (US)

(73) Assignees: THE REGENTS OF THE UNIVERSITY OF CALIFORNIA, Oakland, CA (US); SANOFI, Paris (FR)

( * ) Notice: Subject to any disclaimer, the term of this patent is extended or adjusted under 35 U.S.C. 154(b) by 0 days.

(21) Appl. No.: 14/098,710

(22) Filed: Dec. 6, 2013

(65) Prior Publication Data
US 2014/0161819 A1 Jun. 12, 2014

Related U.S. Application Data

(60) Provisional application No. 61/734,524, filed on Dec. 7, 2012, provisional application No. 61/769,247, filed on Feb. 26, 2013.

(51) Int. Cl.
*A61K 39/395* (2006.01)
*A61K 31/45* (2006.01)
*A61K 45/06* (2006.01)
*A61K 31/37* (2006.01)
*A61K 31/454* (2006.01)
*A61K 31/573* (2006.01)
*A61K 31/616* (2006.01)
*A61K 31/727* (2006.01)

(52) U.S. Cl.
CPC ........ *A61K 39/39558* (2013.01); *A61K 31/37* (2013.01); *A61K 31/45* (2013.01); *A61K 31/454* (2013.01); *A61K 31/573* (2013.01); *A61K 31/616* (2013.01); *A61K 31/727* (2013.01); *A61K 45/06* (2013.01)

(58) Field of Classification Search
CPC .......................... C07K 16/2896; A61K 31/454
See application file for complete search history.

(56) References Cited

U.S. PATENT DOCUMENTS

| 4,444,887 A | 4/1984 | Hoffmann |
| 4,716,111 A | 12/1987 | Osband et al. |
| 4,816,397 A | 3/1989 | Boss et al. |
| 4,816,567 A | 3/1989 | Cabilly et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,639,641 A | 6/1997 | Pedersen et al. |
| 5,807,715 A | 9/1998 | Morrison et al. |
| 5,814,318 A | 9/1998 | Lonberg et al. |
| 8,153,765 B2 | 4/2012 | Park et al. |
| 8,877,899 B2 * | 11/2014 | Rojkjaer et al. ............ 530/387.3 |
| 2009/0148449 A1 | 6/2009 | De Weers et al. |
| 2010/0092489 A1 | 4/2010 | Van De Winkel et al. |
| 2012/0201827 A1 | 8/2012 | Elias et al. |
| 2015/0118251 A1* | 4/2015 | Deslandes ............ A61K 31/573 424/172.1 |
| 2016/0022813 A1* | 1/2016 | Tomkinson ............ A61K 38/07 424/158.1 |

FOREIGN PATENT DOCUMENTS

| CN | 101616933 A | 12/2009 |
| EP | 0 239 400 A2 | 9/1987 |
| EP | 0 239 400 A3 | 9/1987 |
| EP | 0 239 400 B1 | 9/1987 |
| EP | 0 519 596 A1 | 12/1992 |
| EP | 0 519 596 B1 | 12/1992 |
| EP | 0 592 106 A1 | 4/1994 |
| EP | 2 191 840 A1 | 6/2010 |
| EP | 2 191 843 A1 | 6/2010 |
| JP | 2010-506582 A | 3/2010 |
| WO | WO-91/09967 A1 | 7/1991 |
| WO | WO-91/10741 A1 | 7/1991 |
| WO | WO-92/22653 A1 | 12/1992 |
| WO | WO-96/33735 A1 | 10/1996 |
| WO | WO-96/34096 A1 | 10/1996 |
| WO | WO-98/16654 A1 | 4/1998 |
| WO | WO-98/24893 A2 | 6/1998 |
| WO | WO-98/24893 A3 | 6/1998 |
| WO | WO-98/33735 A1 | 8/1998 |
| WO | WO-98/46645 A2 | 10/1998 |
| WO | WO-98/46645 A3 | 10/1998 |
| WO | WO-98/50433 A2 | 11/1998 |
| WO | WO-98/50433 A3 | 11/1998 |
| WO | WO2004/043377 A2 * | 5/2004 |

(Continued)

OTHER PUBLICATIONS

Strome et al., The Oncologist, 2007; 12:1084-95.*
Brand et al., Anticancer Res. 2006; 26:463-70.*
Richardson et al., Br. J. Haematol., 2011; 154:745-54.*
Kurtin et al., J Adv Pract Oncol. 2013; 4(6)Supt 1:5-14.*
Abstract #83 by Martin et al., presented at the 56th Annual Meeting of the American Society of Hematology, Dec. 6-9, 2014.*
ClinicalTrials.gov listing for NCT00574288, study first received Dec. 14, 2007, with appended history of changes for Sep. 30, 2008 (Year: 2007).*
Lokhorst et al., N Engl. J. Med 373:1207-19 (Year: 2015).*
Bataille. R. et al. (Sep. 2006). "The Phenotype of Normal, Reactive and Malignant Plasma Cells. Identification of "Many and Multiple Myelomas" and of New Targets for Myeloma Therapy," *Haematologica* 91(9):1234-1240.

(Continued)

Primary Examiner — Jessica H Roark
(74) Attorney, Agent, or Firm — Morrison & Foerster LLP

(57) ABSTRACT

Disclosed herein are compositions and kits which comprise anti-CD38 antibodies and lenalidomide compounds. Also disclosed are methods for treating cancers, such as multiple myeloma, in subjects with the compositions and kits.

14 Claims, 23 Drawing Sheets

Specification includes a Sequence Listing.

(56) References Cited

FOREIGN PATENT DOCUMENTS

| WO | WO-2008/047242 A2 | 4/2008 |
|---|---|---|
| WO | WO-2008/047242 A3 | 4/2008 |
| WO | WO-2008/047242 A9 | 4/2008 |
| WO | WO-2009/032661 A1 | 3/2009 |
| WO | WO-2010/061360 A1 | 6/2010 |
| WO | WO-2012/041800 A1 | 4/2012 |
| WO | WO-2014/089416 A1 | 6/2014 |

OTHER PUBLICATIONS

De Weers, M. et al. (Feb. 1, 2011; e-pub. Dec. 27, 2010). "Daratumumab, A Novel Therapeutic Human CD38 Monoclonal Antibody, Induces Killing of Multiple Myeloma and Other Hematological Tumors," *J. Immunol.* 186(3):1840-1848.
Dimopoulos, M.A. et al. (Jul. 2010; e-pub. Feb. 20, 2010). "Lenalidomide and Dexamethasone for the Treatment of Refractory/Relapsed Multiple Myeloma: Dosing of Lenalidomide According to Renal Function and Effect on Renal Impairment," *Eur. J. Haematology* 85(1):1-5.
Gillies, S.D. et al. (Dec. 20, 1989). "High-Level Expression of Chimeric Antibodies Using Adapted cDNA Variable Region Cassettes," *J. Immunol. Methods* 125(1-2):191-202.
International Search Report dated Mar. 31, 2014, for PCT Patent Application No. PCT/US2013/073540, filed on Dec. 6, 2013, six pages.
Morrison, S.L. (Sep. 20, 1985). "Transfectomas Provide Novel Chimeric Antibodies," *Science* 229(4719):1202-1207.
Oi, V.T. et al. (1986). "Chimeric Antibodies," *BioTechniques* 4(3):214-221.
Padlan, E.A. (Apr.-May 1991). "A Possible Procedure for Reducing the Immunogenicity of Antibody Variable Domains While Preserving Their Ligand-Binding Properties," *Molecular Immunology* 28(4/5):489-498.
Rajkumar, S.V. et al. (Jan. 2010; e-pub. Oct. 21, 2009). "Lenalidomide Plus High-Dose Dexamethasone Versus Lenalidomide Plus Low-Dose Dexamethasone as Initial Therapy for Newly Diagnosed Multiple Myeloma: An Open-Label Randomised Controlled Trial," *Lancet Onco.* 1 1(1):29-37.
Roguska, M.A. et al. (Feb. 1, 1994). "Humanization of Murine Monoclonal Antibodies Through Variable Domain Resurfacing," *PNAS* 91(3):969-973.
Studnicka, G.M. et al. (Jun. 1994). "Human-Engineered Monoclonal Antibodies Retain Full Specific Binding Activity by Preserving Non-CDR Complementarity-Modulating Residues," *Protein Engineering* 7(6):805-814.
Van Der Veer, M.S. et al. (Feb. 2011; e-pub. Nov. 25, 2010) "Towards Effective Immunotherapy of Myeloma: Enhanced Elimination of Myeloma Cells by Combination of Lenalidomide with the Human CD38 Monoclonal Antibody Daratumumab," *Haematologica* 96(2):284-290.
Wetzel, M-C. et al. (2013). "Hu3 8SB 19: Characterization of a Potent Phase I Humanized Anti-CD38 Antibody for the Treatment of Multiple Myeloma and other Hematologic Malignancies," AACR Annual Meeting 2013, Abstract #4735 (Abstract Only), 1 Total Page.
Clinical Trials. (2012). "A Phase I Dose Escalation Safety and Pharmacokinetic Study of Multiple Intravenous Administrations of a Humanized Monoclonal Antibody (SAR650984) Against CD38 in Patients with Selected CD38+ Hematological Malignancies," located at <clinicaltrials.gov/archive/NCT01084252/2012_09_13>, last visited on Mar. 17, 2016, four pages.
Clinical Trials. (2012). "A Phase 1b Study of SAR650984 (Anti-CD38 mAb) in Combination with Lenalidomide and Dexamethasone for the Treatment of Relapsed or Refractory Multiple Myeloma," located at </clinicaltrials.gov/archive/NCT01749969/2012_12_14>, last visited on Mar. 17, 2016, five pages.
Lejeune, P. et al. (Apr. 2009). "In Vivo Therapeutic Synergy of SAR650984, A Humanized Anti-CD38 Antibody, in Combination with Melphalan in a Multiple Myeloma Xenograft," *presented at the Proceedings of the American Association for Cancer Research Annual Meeting, 100th Annual Meeting if the American-Association-for-Cancer-Research*, Denver, CO, USA, Apr. 18-22, 2009, 50:676, Abstract No. 2797.
Martin, T. et al. (2014). "A Phase IB Dose Escalation Trial of SAR650984 (Anti-CD-38MAB) in Combination with Lenalidomide and Dexamethasone in Relapsed/Refractory Multiple Myeloma," *Haematologica* 99(s1):114.
Richardson, P.G. et al. (Nov. 15, 2006). "A Randomized Phase 2 Study of Lenalidonride Therapy for Patients with Relapsed or Relapsed and Refractory Multiple Myeloma," *Blood* 108(10): 3458-3464.
Van De Donk, N.W. et al. (Aug. 13, 2012). "Lenalidomide for the Treatment of Relapsed and Refractory Multiple Myeloma," *Cancer Management and Research* 4:253-268.
Van Der Veer, M.S. et al. (2010). "Improved Myeloma Targeting by Combination of the Human Anti-CD38 Antibody Daratumumab with Lenalidomide and Bortezomib," *Blood* 116(21):1249, Abstract No. 3030.
Van Der Veer, M.S. et al. (2010). "Towards Effective Immunotherapy of Multiple Myeloma: Enhanced Elimination of Myeloma Cells by Combination of Lenalidomide with the Human CD38 Monoclonal Antibody Daratumumab," Abstract presented at the $52^{nd}$ Annual Meeting of the American-Society-of-Hematology (ASH), Orlando, FL, USA Dec. 4-7, 2010, *Blood* 116(21):1262, Abstract No. 3059.
Extended European Search Report dated Apr. 8, 2016 for European Application No. 13861470.6 filed on Dec. 6, 2013, twenty two pages.
Cesarman-Maus, G. et al. (Apr. 2012). "Thrombosis in Multiple Myeloma (MM)," *Hematology* 17(Supplement 1):S177-S-180.
Hirsch, J. (Oct. 13, 1998). "Low-Molecular-Weight Heparin—A Review of the Results of Recent Studies of the Treatment of Venous Thromboembolism and Unstable Angina," *Circulation* 98(15):1575-1582.
Menon, S.P. et al. (Apr. 1, 2008). "Thromboembolic Events with Lenalidomide-based Therapy for Multiple Myeloma," *Cancer* 112(7):1522-1528.
Written Opinion dated Mar. 31, 2014, for PCT Patent Application No. PCT/US2013/073540, filed on Dec. 6, 2013, seven pages.
Dalton, W.S. et al. (Oct. 1986). "Characterization of a New Drug-Resistant Human Myeloma Cell Line That Expresses P-Glycoprotein," *Cancer Research* 46(10):5125-5130.
Klein, U. et al. (Jan. 2009; e-published Jul. 31, 2008). "Effective Prophylaxis of Thromboembolic Complications With Low Molecular Weight Heparin in Relapsed Multiple Myeloma Patients Treated With Lenalidomide and Dexamethasone," *Annals of Hematology* 88(1):67-71.
Kristinsson, S.Y. (2010). "Thrombosis in Multiple Myeloma," *Hematology Am Soc Hematol Educ Program.* 2010:437-444.
Lonial, S. et al. (Mar. 15, 2011). "Treatment Options for Relapsed and Refractory Multiple Myeloma," *Clinical Cancer Research* 17(6):1264-1277.
Weber, D.M. et al. (Nov. 22, 2007). "Lenalidomide Plus Dexamethasone for Relapsed Multiple Myeloma in North America," *The New England Journal of Medicine* 357(21):2133-2142.
Belikov, V.G. (1993). "Relation Between the Molecular Structure of Compounds and their Action on an Organism," *Pharmaceutical Chemistry* pp. 43-47, ten pages with English translation.
Martin, T. et al. (May 30-Jun. 3, 2014). "A Phase Ib Dose-Escalation Trial of SAR650984 (Anti-CD38 mAb) in Combination with Lenalidomide and Dexamethasone in Relapsed/Refractory Multiple Myeloma," Abstract 8512 *presented at the $50^{th}$ Annual Meeting of the American Society of Clinical Oncology*, Chicago, IL, USA, eighteen pages.
ClinicalTrials.gov. (Jun. 7, 2012). "An Open Label, International, Multicenter, Dose Escalating Phase I/II Trial Investigating the Safety of Daratumumab in Combination With Lenalidomide and Dexamethasone in Patients With Relapsed or Relapsed and Refractory Multiple Myeloma," located at < https://clinicaltrials.gov/ct2/history/NCT01615029?V_1=View >, last visited on Aug. 9, 2018, seven pages.
ClinicalTrials.gov. (Feb. 17, 2011). "A Phase 3, Randomized, Open Label Trial of Lenalidomide/Dexamethasone With or Without

(56) References Cited

OTHER PUBLICATIONS

Elotuzumab in Relapsed or Refractory Multiple Myeloma," located at < https://clinicaltrials.gov/ct2/history/NCT01239797?V_2= View>, last visited on Oct. 15, 2018, eleven pages.

Gandhi, A.K. et al. (2010). "Dexamethasone Synergizes with Lenalidomide to Inhibit Multiple Myeloma Tumor Growth, But Reduces Lenalidomide-Induced Immunomodulation of T and NK Cell Function," *Current Cancer Drug Targets* 10(2):155-167.

Li, S. et al. (May 12, 2011; e-pub. Mar. 9, 2011). "IMiD Immunomodulatory Compounds Block C/EBPβ translation through eIF4E Down-Regulation Resulting in Inhibition of MM," *Blood* 117(19):5157-5165.

Lopez-Girona, A. et al. (2011; e-pub. Jun. 24, 2011). "Lenalidomide Downregulates the Cell Survival Factor, Interferon Regulatory Factor-4, Providing a Potential Mechanistic Link for Predicting Response," *British Journal of Haematology* 154:325-336.

Martin, T. et al. (Jun. 22, 2017; e-pub. May 8, 2017). "A Phase 1b Study of Isatuximab Plus Lenalidomide and Dexamethasone for Relapsed/Refractory Multiple Myeloma," *Blood* 129(25):3294-3303.

\* cited by examiner

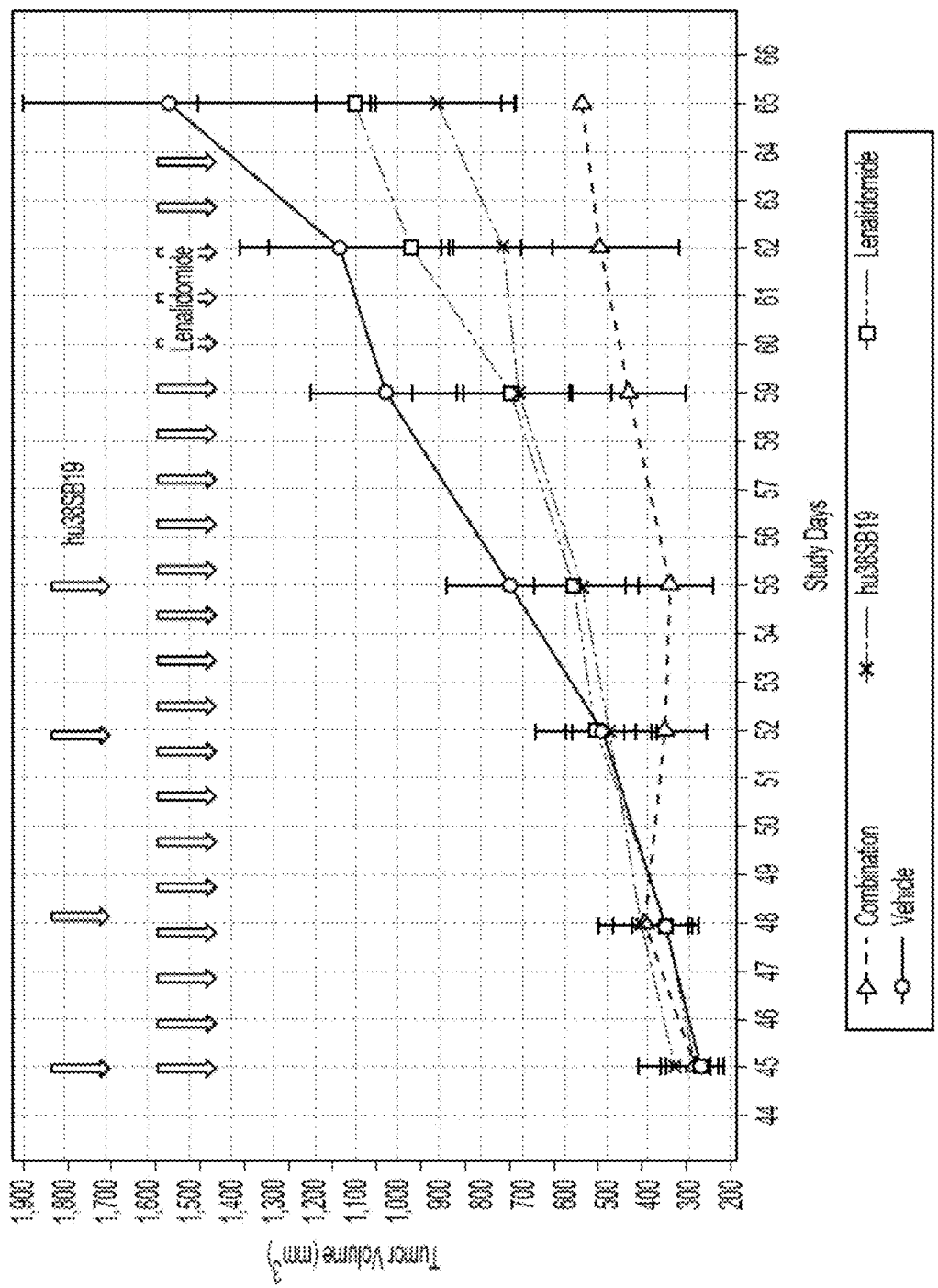

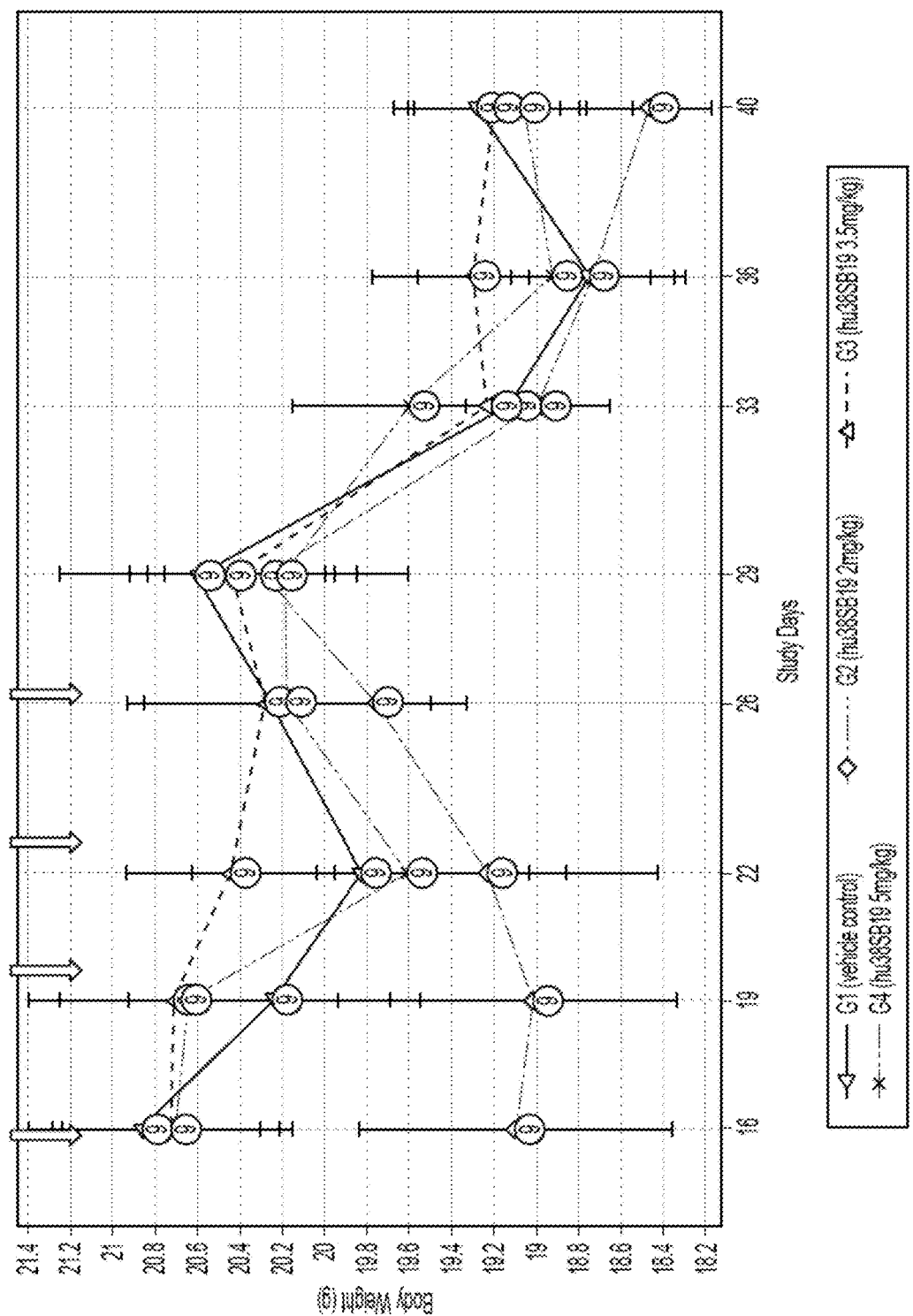

SEQUENCE LISTING

```
<160> NUMBER OF SEQ ID NOS: 81

<210> SEQ ID NO 1
<211> LENGTH: 5
<212> TYPE: PRT
<213> ORGANISM: Mus sp.

<400> SEQUENCE: 1

Ser Tyr Gly Met Asn
1               5

<210> SEQ ID NO 2
<211> LENGTH: 17
<212> TYPE: PRT
<213> ORGANISM: Mus sp.

<400> SEQUENCE: 2

Trp Ile Asn Thr Tyr Thr Gly Glu Pro Thr Tyr Ala Asp Asp Phe Lys
1               5                   10                  15

Gly

<210> SEQ ID NO 3
<211> LENGTH: 5
<212> TYPE: PRT
```

```
<213> ORGANISM: Mus sp.

<400> SEQUENCE: 3

Arg Gly Phe Ala Tyr
1               5

<210> SEQ ID NO 4
<211> LENGTH: 15
<212> TYPE: PRT
<213> ORGANISM: Mus sp.

<400> SEQUENCE: 4

Arg Ala Ser Glu Ser Val Glu Ile Tyr Gly Asn Gly Phe Met Asn
1               5                   10                  15

<210> SEQ ID NO 5
<211> LENGTH: 7
<212> TYPE: PRT
<213> ORGANISM: Mus sp.

<400> SEQUENCE: 5

Arg Ala Ser Asn Leu Glu Ser
1               5

<210> SEQ ID NO 6
<211> LENGTH: 9
<212> TYPE: PRT
<213> ORGANISM: Mus sp.

<400> SEQUENCE: 6

Gln Gln Ile Asn Glu Asp Pro Phe Thr
1               5

<210> SEQ ID NO 7
<211> LENGTH: 5
<212> TYPE: PRT
<213> ORGANISM: Mus sp.

<400> SEQUENCE: 7

Asn Ser Gly Met Asn
1               5

<210> SEQ ID NO 8
<211> LENGTH: 17
<212> TYPE: PRT
<213> ORGANISM: Mus sp.

<400> SEQUENCE: 8

Trp Ile Asn Thr Tyr Thr Gly Glu Pro Thr Tyr Ala Asp Asp Phe Lys
1               5                   10                  15

Gly

<210> SEQ ID NO 9
<211> LENGTH: 5
<212> TYPE: PRT
<213> ORGANISM: Mus sp.

<400> SEQUENCE: 9

Arg Gly Phe Val Tyr
1               5

<210> SEQ ID NO 10
<211> LENGTH: 15
<212> TYPE: PRT
```

<213> ORGANISM: Mus sp.

<400> SEQUENCE: 10

Arg Ala Ser Glu Ser Val Ala Ile Tyr Gly Asn Ser Phe Leu Lys
1               5                   10                  15

<210> SEQ ID NO 11
<211> LENGTH: 7
<212> TYPE: PRT
<213> ORGANISM: Mus sp.

<400> SEQUENCE: 11

Arg Ala Ser Asn Leu Glu Ser
1               5

<210> SEQ ID NO 12
<211> LENGTH: 9
<212> TYPE: PRT
<213> ORGANISM: Mus sp.

<400> SEQUENCE: 12

Gln Gln Ile Asn Glu Asp Pro Tyr Thr
1               5

<210> SEQ ID NO 13
<211> LENGTH: 5
<212> TYPE: PRT
<213> ORGANISM: Mus sp.

<400> SEQUENCE: 13

Asp Tyr Trp Met Gln
1               5

<210> SEQ ID NO 14
<211> LENGTH: 17
<212> TYPE: PRT
<213> ORGANISM: Mus sp.

<400> SEQUENCE: 14

Thr Ile Tyr Pro Gly Asp Gly Asp Thr Gly Tyr Ala Gln Lys Phe Lys
1               5                   10                  15

Gly

<210> SEQ ID NO 15
<211> LENGTH: 11
<212> TYPE: PRT
<213> ORGANISM: Mus sp.

<400> SEQUENCE: 15

Gly Asp Tyr Tyr Gly Ser Asn Ser Leu Asp Tyr
1               5                   10

<210> SEQ ID NO 16
<211> LENGTH: 11
<212> TYPE: PRT
<213> ORGANISM: Mus sp.

<400> SEQUENCE: 16

Lys Ala Ser Gln Asp Val Ser Thr Val Val Ala
1               5                   10

<210> SEQ ID NO 17
<211> LENGTH: 7
<212> TYPE: PRT

```
<213> ORGANISM: Mus sp.

<400> SEQUENCE: 17

Ser Ala Ser Tyr Arg Tyr Ile
1               5

<210> SEQ ID NO 18
<211> LENGTH: 9
<212> TYPE: PRT
<213> ORGANISM: Mus sp.

<400> SEQUENCE: 18

Gln Gln His Tyr Ser Pro Pro Tyr Thr
1               5

<210> SEQ ID NO 19
<211> LENGTH: 5
<212> TYPE: PRT
<213> ORGANISM: Mus sp.

<400> SEQUENCE: 19

Gly Ser Trp Met Asn
1               5

<210> SEQ ID NO 20
<211> LENGTH: 17
<212> TYPE: PRT
<213> ORGANISM: Mus sp.

<400> SEQUENCE: 20

Arg Ile Tyr Pro Gly Asp Gly Asp Ile Ile Tyr Asn Gly Asn Phe Arg
1               5                   10                  15

Asp

<210> SEQ ID NO 21
<211> LENGTH: 10
<212> TYPE: PRT
<213> ORGANISM: Mus sp.

<400> SEQUENCE: 21

Trp Gly Thr Phe Thr Pro Ser Phe Asp Tyr
1               5                   10

<210> SEQ ID NO 22
<211> LENGTH: 11
<212> TYPE: PRT
<213> ORGANISM: Mus sp.

<400> SEQUENCE: 22

Lys Ala Ser Gln Asp Val Val Thr Ala Val Ala
1               5                   10

<210> SEQ ID NO 23
<211> LENGTH: 7
<212> TYPE: PRT
<213> ORGANISM: Mus sp.

<400> SEQUENCE: 23

Ser Ala Ser His Arg Tyr Thr
1               5

<210> SEQ ID NO 24
<211> LENGTH: 9
<212> TYPE: PRT
```

<213> ORGANISM: Mus sp.

<400> SEQUENCE: 24

Gln Gln His Tyr Thr Thr Pro Thr Thr
1               5

<210> SEQ ID NO 25
<211> LENGTH: 5
<212> TYPE: PRT
<213> ORGANISM: Mus sp.

<400> SEQUENCE: 25

Ser Tyr Thr Leu Ser
1               5

<210> SEQ ID NO 26
<211> LENGTH: 17
<212> TYPE: PRT
<213> ORGANISM: Mus sp.

<400> SEQUENCE: 26

Thr Ile Ser Ile Gly Gly Arg Tyr Thr Tyr Tyr Pro Asp Ser Val Glu
1               5                   10                  15

Gly

<210> SEQ ID NO 27
<211> LENGTH: 8
<212> TYPE: PRT
<213> ORGANISM: Mus sp.

<400> SEQUENCE: 27

Asp Phe Asn Gly Tyr Ser Asp Phe
1               5

<210> SEQ ID NO 28
<211> LENGTH: 11
<212> TYPE: PRT
<213> ORGANISM: Mus sp.

<400> SEQUENCE: 28

Lys Ala Ser Gln Val Val Gly Ser Ala Val Ala
1               5                   10

<210> SEQ ID NO 29
<211> LENGTH: 7
<212> TYPE: PRT
<213> ORGANISM: Mus sp.

<400> SEQUENCE: 29

Trp Ala Ser Thr Arg His Thr
1               5

<210> SEQ ID NO 30
<211> LENGTH: 9
<212> TYPE: PRT
<213> ORGANISM: Mus sp.

<400> SEQUENCE: 30

Gln Gln Tyr Asn Ser Tyr Pro Tyr Thr
1               5

<210> SEQ ID NO 31
<211> LENGTH: 5
<212> TYPE: PRT

```
<213> ORGANISM: Mus sp.

<400> SEQUENCE: 31

Asn Phe Gly Met His
1               5

<210> SEQ ID NO 32
<211> LENGTH: 17
<212> TYPE: PRT
<213> ORGANISM: Mus sp.

<400> SEQUENCE: 32

Tyr Ile Arg Ser Gly Ser Gly Thr Ile Tyr Tyr Ser Asp Thr Val Lys
1               5                   10                  15

Gly

<210> SEQ ID NO 33
<211> LENGTH: 11
<212> TYPE: PRT
<213> ORGANISM: Mus sp.

<400> SEQUENCE: 33

Ser Tyr Tyr Asp Phe Gly Ala Trp Phe Ala Tyr
1               5                   10

<210> SEQ ID NO 34
<211> LENGTH: 11
<212> TYPE: PRT
<213> ORGANISM: Mus sp.

<400> SEQUENCE: 34

Lys Ala Ser Gln Asn Val Gly Thr Asn Val Ala
1               5                   10

<210> SEQ ID NO 35
<211> LENGTH: 7
<212> TYPE: PRT
<213> ORGANISM: Mus sp.

<400> SEQUENCE: 35

Ser Ala Ser Ser Arg Tyr Ser
1               5

<210> SEQ ID NO 36
<211> LENGTH: 9
<212> TYPE: PRT
<213> ORGANISM: Mus sp.

<400> SEQUENCE: 36

Gln Gln Tyr Asn Ser Tyr Pro Leu Thr
1               5

<210> SEQ ID NO 37
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 37 aac att gtg ctg acc caa tct cca gct tct ttg gct gtg tct ctt ggg    48
Asn Ile Val Leu Thr Gln Ser Pro Ala Ser Leu Ala Val Ser Leu Gly
1               5                   10                  15
```

| | |
|---|---|
| cag agg gcc acc ata tcc tgc aga gcc agt gaa agt gtt gag att tat<br>Gln Arg Ala Thr Ile Ser Cys Arg Ala Ser Glu Ser Val Glu Ile Tyr<br>        20                   25                  30 | 96 |
| ggc aat ggt ttt atg aac tgg ttc cag cag aaa cca gga cag cca ccc<br>Gly Asn Gly Phe Met Asn Trp Phe Gln Gln Lys Pro Gly Gln Pro Pro<br>         35                   40                   45 | 144 |
| aaa ctc ctc atc tat cgt gca tcc aac cta gaa tct ggg atc cct gcc<br>Lys Leu Leu Ile Tyr Arg Ala Ser Asn Leu Glu Ser Gly Ile Pro Ala<br>    50                   55                   60 | 192 |
| agg ttc agt ggc agt ggg tct agg aca gag ttc acc ctc acc att gat<br>Arg Phe Ser Gly Ser Gly Ser Arg Thr Glu Phe Thr Leu Thr Ile Asp<br>65                  70                   75                 80 | 240 |
| cct gtg gag gct gat gat gtt gca acc tat tac tgt caa caa att aat<br>Pro Val Glu Ala Asp Asp Val Ala Thr Tyr Tyr Cys Gln Gln Ile Asn<br>                   85                   90                 95 | 288 |
| gag gat cca ttc acg ttc ggc tcg ggg aca aag ttg gaa ata aaa cgg<br>Glu Asp Pro Phe Thr Phe Gly Ser Gly Thr Lys Leu Glu Ile Lys Arg<br>            100                     105               110 | 336 |

<210> SEQ ID NO 38
<211> LENGTH: 112
<212> TYPE: PRT
<213> ORGANISM: Mus sp.

<400> SEQUENCE: 38

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Ile Tyr
            20                  25                  30

Gly Asn Gly Phe Met Asn Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Glu Phe Thr Leu Thr Ile Asp
65                  70                  75                  80

Pro Val Glu Ala Asp Asp Val Ala Thr Tyr Tyr Cys Gln Gln Ile Asn
                85                  90                  95

Glu Asp Pro Phe Thr Phe Gly Ser Gly Thr Lys Leu Glu Ile Lys Arg
            100                 105                 110

<210> SEQ ID NO 39
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 39

| | |
|---|---|
| gac att gta ctg acc caa tct cca gct tct ttg gct gtg tct cta ggg<br>Asp Ile Val Leu Thr Gln Ser Pro Ala Ser Leu Ala Val Ser Leu Gly<br>1                 5                     10                   15 | 48 |
| cag agg gcc acc ata tcc tgc aga gcc agt gag agt gtt gct att tat<br>Gln Arg Ala Thr Ile Ser Cys Arg Ala Ser Glu Ser Val Ala Ile Tyr<br>        20                   25                   30 | 96 |
| ggc aat agt ttt ctg aaa tgg ttc cag cag aaa ccg gga cag cca ccc<br>Gly Asn Ser Phe Leu Lys Trp Phe Gln Gln Lys Pro Gly Gln Pro Pro<br>         35                   40                   45 | 144 |
| aaa ctc ctc atc tat cgt gca tcc aac cta gaa tct ggg atc cct gcc<br>Lys Leu Leu Ile Tyr Arg Ala Ser Asn Leu Glu Ser Gly Ile Pro Ala<br>    50                   55                   60 | 192 |

```
agg ttc agt ggc agt ggg tct ggg aca gac ttc acc ctc acc att aat     240
Arg Phe Ser Gly Ser Gly Ser Gly Thr Asp Phe Thr Leu Thr Ile Asn
 65                  70                  75                  80 cct gtg gag gct gat gat gtt gca acc tat tac tgt cag caa att aat     288
Pro Val Glu Ala Asp Asp Val Ala Thr Tyr Tyr Cys Gln Gln Ile Asn
                 85                  90                  95 gag gat ccg tac acg ttc gga ggg ggg acc aag ctg gaa ata aaa cgg     336
Glu Asp Pro Tyr Thr Phe Gly Gly Gly Thr Lys Leu Glu Ile Lys Arg
            100                 105                 110

<210> SEQ ID NO 40
<211> LENGTH: 112
<212> TYPE: PRT
<213> ORGANISM: Mus sp.

<400> SEQUENCE: 40

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Ala Ile Tyr
             20                  25                  30

Gly Asn Ser Phe Leu Lys Trp Phe Gln Gln Lys Pro Gly Gln Pro Pro
         35                  40                  45

Lys Leu Leu Ile Tyr Arg Ala Ser Asn Leu Glu Ser Gly Ile Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asp Asp Val Ala Thr Tyr Tyr Cys Gln Gln Ile Asn
                 85                  90                  95

Glu Asp Pro Tyr Thr Phe Gly Gly Gly Thr Lys Leu Glu Ile Lys Arg
            100                 105                 110

<210> SEQ ID NO 41
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 41 gac att gtg atg gcc cag tct cac aaa ttc atg tcc aca tca gtt gga      48
Asp Ile Val Met Ala Gln Ser His Lys Phe Met Ser Thr Ser Val Gly
 1               5                  10                  15 gac agg gtc agc atc acc tgc aag gcc agt cag gat gtg agt act gtt      96
Asp Arg Val Ser Ile Thr Cys Lys Ala Ser Gln Asp Val Ser Thr Val
             20                  25                  30 gtg gcc tgg tat caa cag aaa cca gga caa tct cct aaa cga ctg att     144
Val Ala Trp Tyr Gln Gln Lys Pro Gly Gln Ser Pro Lys Arg Leu Ile
         35                  40                  45 tac tcg gca tcc tat cgg tat att gga gtc cct gat cgc ttc act ggc     192
Tyr Ser Ala Ser Tyr Arg Tyr Ile Gly Val Pro Asp Arg Phe Thr Gly
 50                  55                  60 agt gga tct ggg acg gat ttc act ttc acc atc agc agt gtg cag gct     240
Ser Gly Ser Gly Thr Asp Phe Thr Phe Thr Ile Ser Ser Val Gln Ala
 65                  70                  75                  80 gaa gac ctg gca gtt tat tac tgt cag caa cat tat agt cct ccg tac     288
Glu Asp Leu Ala Val Tyr Tyr Cys Gln Gln His Tyr Ser Pro Pro Tyr
                 85                  90                  95 acg ttc gga ggg ggg acc aag ctg gaa ata aaa cgg                     324
Thr Phe Gly Gly Gly Thr Lys Leu Glu Ile Lys Arg
```

<210> SEQ ID NO 42
<211> LENGTH: 108
<212> TYPE: PRT
<213> ORGANISM: Mus sp.

<400> SEQUENCE: 42

```
Asp Ile Val Met Ala Gln Ser His Lys Phe Met Ser Thr Ser Val Gly
1               5                   10                  15

Asp Arg Val Ser Ile Thr Cys Lys Ala Ser Gln Asp Val Ser Thr Val
            20                  25                  30

Val Ala Trp Tyr Gln Lys Pro Gly Gln Ser Pro Lys Arg Leu Ile
        35                  40                  45

Tyr Ser Ala Ser Tyr Arg Tyr Ile Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105
```

<210> SEQ ID NO 43
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 43

```
gac att gtg atg acc cag tct cac aaa ttc ttg tcc aca tca gtt gga      48
Asp Ile Val Met Thr Gln Ser His Lys Phe Leu Ser Thr Ser Val Gly
1               5                   10                  15 gac agg gtc agt atc acc tgc aag gcc agt cag gat gtg gtt act gct      96
Asp Arg Val Ser Ile Thr Cys Lys Ala Ser Gln Asp Val Val Thr Ala
            20                  25                  30 gtt gcc tgg ttt caa cag aaa cca gga caa tct cca aaa cta ctg att     144
Val Ala Trp Phe Gln Gln Lys Pro Gly Gln Ser Pro Lys Leu Leu Ile
        35                  40                  45 tat tcg gca tcc cac cgg tac act gga gtc cct gat cgc ttc act ggc     192
Tyr Ser Ala Ser His Arg Tyr Thr Gly Val Pro Asp Arg Phe Thr Gly
    50                  55                  60 agt gga tct ggg aca gat ttc act ttc acc atc atc agt gtg cag gct     240
Ser Gly Ser Gly Thr Asp Phe Thr Phe Thr Ile Ile Ser Val Gln Ala
65                  70                  75                  80 gaa gac ctg gca gtt tat tac tgt caa caa cat tat act act ccc acg     288
Glu Asp Leu Ala Val Tyr Tyr Cys Gln Gln His Tyr Thr Thr Pro Thr
                85                  90                  95 acg ttc ggt gga ggc acc aag ctg gac ttc aga cgg                     324
Thr Phe Gly Gly Gly Thr Lys Leu Asp Phe Arg Arg
            100                 105
```

<210> SEQ ID NO 44
<211> LENGTH: 108
<212> TYPE: PRT
<213> ORGANISM: Mus sp.

<400> SEQUENCE: 44

Asp Ile Val Met Thr Gln Ser His Lys Phe Leu Ser Thr Ser Val Gly

```
                1               5                       10                      15
            Asp Arg Val Ser Ile Thr Cys Lys Ala Ser Gln Asp Val Val Thr Ala
                            20                      25                      30

Val Ala Trp Phe Gln Gln Lys Pro Gly Gln Ser Pro Lys Leu Leu Ile
                        35                      40                      45

Tyr Ser Ala Ser His Arg Tyr Thr Gly Val Pro Asp Arg Phe Thr Gly
                    50                      55                      60

Ser Gly Ser Gly Thr Asp Phe Thr Phe Thr Ile Ile Ser Val Gln Ala
            65                      70                      75                      80

Glu Asp Leu Ala Val Tyr Tyr Cys Gln Gln His Tyr Thr Thr Pro Thr
                                85                      90                      95

Thr Phe Gly Gly Gly Thr Lys Leu Asp Phe Arg Arg
                            100                     105

<210> SEQ ID NO 45
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 45 gac act gtg atg acc cag tct cac aaa ttc ata tcc aca tca gtt gga        48
Asp Thr Val Met Thr Gln Ser His Lys Phe Ile Ser Thr Ser Val Gly
1               5                       10                      15 gac agg gtc agc atc acc tgc aag gcc agt cag gtt gtg ggt agt gct        96
Asp Arg Val Ser Ile Thr Cys Lys Ala Ser Gln Val Val Gly Ser Ala
                20                      25                      30 gta gcc tgg tat caa cag aaa cca ggg caa tct cct aaa cta ctg att       144
Val Ala Trp Tyr Gln Gln Lys Pro Gly Gln Ser Pro Lys Leu Leu Ile
            35                      40                      45 tac tgg gca tcc acc cgg cac act gga gtc cct gat cgc ttc aca ggc       192
Tyr Trp Ala Ser Thr Arg His Thr Gly Val Pro Asp Arg Phe Thr Gly
        50                      55                      60 agt gga tct ggg aca gat ttc act ctc acc att agc aat gtg cag tct       240
Ser Gly Ser Gly Thr Asp Phe Thr Leu Thr Ile Ser Asn Val Gln Ser
65                      70                      75                      80 gaa gac ttg gca gat tat ttc tgt cag caa tat aac agc tat ccg tac       288
Glu Asp Leu Ala Asp Tyr Phe Cys Gln Gln Tyr Asn Ser Tyr Pro Tyr
                85                      90                      95 acg ttc gga ggg ggg acc aag ctg gaa ata aaa cgg                       324
Thr Phe Gly Gly Gly Thr Lys Leu Glu Ile Lys Arg
                100                     105

<210> SEQ ID NO 46
<211> LENGTH: 108
<212> TYPE: PRT
<213> ORGANISM: Mus sp.

<400> SEQUENCE: 46

Asp Thr Val Met Thr Gln Ser His Lys Phe Ile Ser Thr Ser Val Gly
1               5                       10                      15

Asp Arg Val Ser Ile Thr Cys Lys Ala Ser Gln Val Val Gly Ser Ala
                20                      25                      30

Val Ala Trp Tyr Gln Gln Lys Pro Gly Gln Ser Pro Lys Leu Leu Ile
            35                      40                      45

Tyr Trp Ala Ser Thr Arg His Thr Gly Val Pro Asp Arg Phe Thr Gly
        50                      55                      60
```

```
Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Asn Ser Tyr Pro Tyr
                 85                  90                  95

Thr Phe Gly Gly Gly Thr Lys Leu Glu Ile Lys Arg
            100                 105

<210> SEQ ID NO 47
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 47 gac att gtg atg acc cag tct caa aaa ttc atg tcc aca tca gta gga      48
Asp Ile Val Met Thr Gln Ser Gln Lys Phe Met Ser Thr Ser Val Gly
 1                5                   10                  15 gac agg gtc agc gtc acc tgc aag gcc agt cag aat gtg ggt act aat     96
Asp Arg Val Ser Val Thr Cys Lys Ala Ser Gln Asn Val Gly Thr Asn
             20                  25                  30 gtt gcc tgg tat caa cac aaa cca gga caa tcc cct aaa ata atg att    144
Val Ala Trp Tyr Gln His Lys Pro Gly Gln Ser Pro Lys Ile Met Ile
         35                  40                  45 tat tcg gcg tcc tcc cgg tac agt gga gtc cct gat cgc ttc aca ggc    192
Tyr Ser Ala Ser Ser Arg Tyr Ser Gly Val Pro Asp Arg Phe Thr Gly
     50                  55                  60 agt gga tct ggg aca ctt ttc act ctc acc atc aac aat gtg cag tct    240
Ser Gly Ser Gly Thr Leu Phe Thr Leu Thr Ile Asn Asn Val Gln Ser
 65                  70                  75                  80 gaa gac ttg gca gag tat ttc tgt cag caa tat aac agc tat cct ctc    288
Glu Asp Leu Ala Glu Tyr Phe Cys Gln Gln Tyr Asn Ser Tyr Pro Leu
                 85                  90                  95 acg ttc ggc tcg ggg aca aag ttg gaa ata aaa cgg                    324
Thr Phe Gly Ser Gly Thr Lys Leu Glu Ile Lys Arg
            100                 105

<210> SEQ ID NO 48
<211> LENGTH: 108
<212> TYPE: PRT
<213> ORGANISM: Mus sp.

<400> SEQUENCE: 48

Asp Ile Val Met Thr Gln Ser Gln Lys Phe Met Ser Thr Ser Val Gly
 1                5                   10                  15

Asp Arg Val Ser Val Thr Cys Lys Ala Ser Gln Asn Val Gly Thr Asn
             20                  25                  30

Val Ala Trp Tyr Gln His Lys Pro Gly Gln Ser Pro Lys Ile Met Ile
         35                  40                  45

Tyr Ser Ala Ser Ser Arg Tyr Ser Gly Val Pro Asp Arg Phe Thr Gly
     50                  55                  60

Ser Gly Ser Gly Thr Leu Phe Thr Leu Thr Ile Asn Asn Val Gln Ser
 65                  70                  75                  80

Glu Asp Leu Ala Glu Tyr Phe Cys Gln Gln Tyr Asn Ser Tyr Pro Leu
                 85                  90                  95

Thr Phe Gly Ser Gly Thr Lys Leu Glu Ile Lys Arg
            100                 105

<210> SEQ ID NO 49
```

```
<211> LENGTH: 342
<212> TYPE: DNA
<213> ORGANISM: Mus sp.
<220> FEATURE:
<221> NAME/KEY: CDS
<222> LOCATION: (1)..(342)

<400> SEQUENCE: 49 cag atc cag ttg gtg cag tct gga cct gag ctg aag aag cct gga gag     48
Gln Ile Gln Leu Val Gln Ser Gly Pro Glu Leu Lys Lys Pro Gly Glu
1               5                   10                  15 aca gtc aag atc tcc tgc aag gct tct ggg tat acc ctc aca agc tac     96
Thr Val Lys Ile Ser Cys Lys Ala Ser Gly Tyr Thr Leu Thr Ser Tyr
            20                  25                  30 gga atg aac tgg gtg aag cag gct cca gga aag ggt tta aag tgg atg    144
Gly Met Asn Trp Val Lys Gln Ala Pro Gly Lys Gly Leu Lys Trp Met
        35                  40                  45 ggc tgg ata aac acc tac act gga gaa cca aca tat gct gat gac ttt    192
Gly Trp Ile Asn Thr Tyr Thr Gly Glu Pro Thr Tyr Ala Asp Asp Phe
    50                  55                  60 aag gga cgt ttt gcc ttc tct ttg gaa acc tct gcc agc act gcc ttt    240
Lys Gly Arg Phe Ala Phe Ser Leu Glu Thr Ser Ala Ser Thr Ala Phe
65                  70                  75                  80 ttg cag atc aac aac ctc aaa aat gag gac acg gct aca tat ttc tgt    288
Leu Gln Ile Asn Asn Leu Lys Asn Glu Asp Thr Ala Thr Tyr Phe Cys
                85                  90                  95 gta aga cgc ggg ttt gct tac tgg ggc caa ggg act ctg gtc act gtc    336
Val Arg Arg Gly Phe Ala Tyr Trp Gly Gln Gly Thr Leu Val Thr Val
            100                 105                 110 tct gca                                                            342
Ser Ala

<210> SEQ ID NO 50
<211> LENGTH: 114
<212> TYPE: PRT
<213> ORGANISM: Mus sp.

<400> SEQUENCE: 50

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Leu Thr Ser Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Val Arg Arg Gly Phe Ala Tyr Trp Gly Gln Gly Thr Leu Val Thr Val
            100                 105                 110

Ser Ala

<210> SEQ ID NO 51
<211> LENGTH: 342
<212> TYPE: DNA
<213> ORGANISM: Mus sp.
<220> FEATURE:
<221> NAME/KEY: CDS
<222> LOCATION: (1)..(342)
```

<400> SEQUENCE: 51

```
cag atc cag ttg gtg cag tct gga cct gag ctg aag aag cct gga gag        48
Gln Ile Gln Leu Val Gln Ser Gly Pro Glu Leu Lys Lys Pro Gly Glu
1               5                   10                  15 aca gtc aag atc tcc tgc aag gct tct ggg tat acc ttc aca aac tct        96
Thr Val Lys Ile Ser Cys Lys Ala Ser Gly Tyr Thr Phe Thr Asn Ser
            20                  25                  30 gga atg aac tgg gtg aag cag gct cca gga aag ggt tta aag tgg atg       144
Gly Met Asn Trp Val Lys Gln Ala Pro Gly Lys Gly Leu Lys Trp Met
        35                  40                  45 ggc tgg ata aac acc tac act gga gag ccg aca tat gct gat gac ttc       192
Gly Trp Ile Asn Thr Tyr Thr Gly Glu Pro Thr Tyr Ala Asp Asp Phe
    50                  55                  60 aag gga cgg ttt gcc ttc tct ttg gaa acc tct gcc agc tct gcc tat       240
Lys Gly Arg Phe Ala Phe Ser Leu Glu Thr Ser Ala Ser Ser Ala Tyr
65                  70                  75                  80 ttg cag atc agt aac ctc aaa aat gag gac acg gct aca tat ttc tgt       288
Leu Gln Ile Ser Asn Leu Lys Asn Glu Asp Thr Ala Thr Tyr Phe Cys
                85                  90                  95 gca aga agg ggt ttt gtt tac tgg ggc caa ggg act ctg gta act gtc       336
Ala Arg Arg Gly Phe Val Tyr Trp Gly Gln Gly Thr Leu Val Thr Val
            100                 105                 110 tct gca                                                                342
Ser Ala
```

<210> SEQ ID NO 52
<211> LENGTH: 114
<212> TYPE: PRT
<213> ORGANISM: Mus sp.

<400> SEQUENCE: 52

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Ser
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Ser Ala Tyr
65                  70                  75                  80

Leu Gln Ile Ser Asn Leu Lys Asn Glu Asp Thr Ala Thr Tyr Phe Cys
                85                  90                  95

Ala Arg Arg Gly Phe Val Tyr Trp Gly Gln Gly Thr Leu Val Thr Val
            100                 105                 110

Ser Ala
```

<210> SEQ ID NO 53
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 53

```
cag gtt cag ctc cag cag tct ggg gct gag ctg gca aga cct ggg act        48
Gln Val Gln Leu Gln Gln Ser Gly Ala Glu Leu Ala Arg Pro Gly Thr
1               5                   10                  15
```

```
tca gtg aag ttg tcc tgt aag gct tct ggc tac acc ttt act gac tac      96
Ser Val Lys Leu Ser Cys Lys Ala Ser Gly Tyr Thr Phe Thr Asp Tyr
        20                  25                  30 tgg atg cag tgg gta aaa cag agg cct gga cag ggt ctg gag tgg att     144
Trp Met Gln Trp Val Lys Gln Arg Pro Gly Gln Gly Leu Glu Trp Ile
        35                  40                  45 ggg act att tat cct gga gat ggt gat act ggg tac gct cag aag ttc     192
Gly Thr Ile Tyr Pro Gly Asp Gly Asp Thr Gly Tyr Ala Gln Lys Phe
    50                  55                  60 aag ggc aag gcc aca ttg act gcg gat aaa tcc tcc aaa aca gtc tac     240
Lys Gly Lys Ala Thr Leu Thr Ala Asp Lys Ser Ser Lys Thr Val Tyr
65                  70                  75                  80 atg cac ctc agc agt ttg gct tct gag gac tct gcg gtc tat tac tgt     288
Met His Leu Ser Ser Leu Ala Ser Glu Asp Ser Ala Val Tyr Tyr Cys
                85                  90                  95 gca aga ggg gat tac tac ggt agt aat tct ttg gac tat tgg ggt caa    336
Ala Arg Gly Asp Tyr Tyr Gly Ser Asn Ser Leu Asp Tyr Trp Gly Gln
            100                 105                 110 gga acc tca gtc acc gtc tcc tca                                     360
Gly Thr Ser Val Thr Val Ser Ser
            115                 120

<210> SEQ ID NO 54
<211> LENGTH: 120
<212> TYPE: PRT
<213> ORGANISM: Mus sp.

<400> SEQUENCE: 54

Gln Val Gln Leu Gln Gln Ser Gly Ala Glu Leu Ala Arg Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Lys Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
            115                 120

<210> SEQ ID NO 55
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 55 cag gtc cag tta cag caa tct gga cct gaa ctg gtg agg cct ggg gcc      48
Gln Val Gln Leu Gln Gln Ser Gly Pro Glu Leu Val Arg Pro Gly Ala
1               5                   10                  15 tca gtg aag att tcc tgc aaa act tct ggc tac gca ttc agt ggc tcc     96
Ser Val Lys Ile Ser Cys Lys Thr Ser Gly Tyr Ala Phe Ser Gly Ser
            20                  25                  30
```

```
tgg atg aac tgg gtg aag cag agg cct gga cag ggt cta gag tgg att    144
Trp Met Asn Trp Val Lys Gln Arg Pro Gly Gln Gly Leu Glu Trp Ile
        35                  40                  45 gga cgg att tat ccg gga gat gga gat atc att tac aat ggg aat ttc    192
Gly Arg Ile Tyr Pro Gly Asp Gly Asp Ile Ile Tyr Asn Gly Asn Phe
 50                  55                  60 agg gac aag gtc aca ctg tct gca gac aaa tcc tcc aac aca gcc tac    240
Arg Asp Lys Val Thr Leu Ser Ala Asp Lys Ser Ser Asn Thr Ala Tyr
65                  70                  75                  80 atg cag ctc agc agc ctg acc tct gtg gac tct gcg gtc tat ttt tgt    288
Met Gln Leu Ser Ser Leu Thr Ser Val Asp Ser Ala Val Tyr Phe Cys
                85                  90                  95 tcg aga tgg ggg aca ttt acg ccg agt ttt gac tat tgg ggc caa ggc    336
Ser Arg Trp Gly Thr Phe Thr Pro Ser Phe Asp Tyr Trp Gly Gln Gly
            100                 105                 110 acc act ctc aca gtc tcc tca                                         357
Thr Thr Leu Thr Val Ser Ser
            115

<210> SEQ ID NO 56
<211> LENGTH: 119
<212> TYPE: PRT
<213> ORGANISM: Mus sp.

<400> SEQUENCE: 56

Gln Val Gln Leu Gln Gln Ser Gly Pro Glu Leu Val Arg Pro Gly Ala
 1               5                   10                  15

Ser Val Lys Ile Ser Cys Lys Thr Ser Gly Tyr Ala Phe Ser Gly Ser
                20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Ile Ile Tyr Asn Gly Asn Phe
 50                  55                  60

Arg Asp Lys Val Thr Leu Ser Ala Asp Lys Ser Ser Asn Thr Ala Tyr
65                  70                  75                  80

Met Gln Leu Ser Ser Leu Thr Ser Val Asp Ser Ala Val Tyr Phe Cys
                85                  90                  95

Ser Arg Trp Gly Thr Phe Thr Pro Ser Phe Asp Tyr Trp Gly Gln Gly
            100                 105                 110

Thr Thr Leu Thr Val Ser Ser
            115

<210> SEQ ID NO 57
<211> LENGTH: 351
<212> TYPE: DNA
<213> ORGANISM: Mus sp.
<220> FEATURE:
<221> NAME/KEY: CDS
<222> LOCATION: (1)..(351)

<400> SEQUENCE: 57 gac gtg aag ctg gtg gag tct ggg gga ggc tta gtg aag cct gga ggg     48
Asp Val Lys Leu Val Glu Ser Gly Gly Gly Leu Val Lys Pro Gly Gly
 1               5                   10                  15 tcc ctg aaa ctc tcc tgt gaa gcc tct gga ttc act ttc agt agc tat     96
Ser Leu Lys Leu Ser Cys Glu Ala Ser Gly Phe Thr Phe Ser Ser Tyr
                20                  25                  30 acc ctg tct tgg gtt cgc cag act ccg gag acg agg ctg gag tgg gtc    144
Thr Leu Ser Trp Val Arg Gln Thr Pro Glu Thr Arg Leu Glu Trp Val
            35                  40                  45
```

```
gca acc att agt att ggt ggt cgc tac acc tat tat cca gac agt gtg    192
Ala Thr Ile Ser Ile Gly Gly Arg Tyr Thr Tyr Tyr Pro Asp Ser Val
 50                  55                  60 gag ggc cga ttc acc atc tcc aga gac aat gcc aag aac acc ctg tac    240
Glu Gly Arg Phe Thr Ile Ser Arg Asp Asn Ala Lys Asn Thr Leu Tyr
 65                  70                  75                  80 ctg caa atg aac agt ctg aag tct gag gac aca gcc atg tat tac tgt    288
Leu Gln Met Asn Ser Leu Lys Ser Glu Asp Thr Ala Met Tyr Tyr Cys
                 85                  90                  95 aca aga gat ttt aat ggt tac tct gac ttc tgg ggc caa ggc acc act    336
Thr Arg Asp Phe Asn Gly Tyr Ser Asp Phe Trp Gly Gln Gly Thr Thr
                100                 105                 110 ctc aca gtc tcc tca                                                351
Leu Thr Val Ser Ser
            115
```

```
<210> SEQ ID NO 58
<211> LENGTH: 117
<212> TYPE: PRT
<213> ORGANISM: Mus sp.

<400> SEQUENCE: 58

Asp Val Lys Leu Val Glu Ser Gly Gly Gly Leu Val Lys Pro Gly Gly
 1               5                  10                  15

Ser Leu Lys Leu Ser Cys Glu Ala Ser Gly Phe Thr Phe Ser Ser Tyr
             20                  25                  30

Thr Leu Ser Trp Val Arg Gln Thr Pro Glu Thr Arg Leu Glu Trp Val
         35                  40                  45

Ala Thr Ile Ser Ile Gly Gly Arg Tyr Thr Tyr Tyr Pro Asp Ser Val
 50                  55                  60

Glu Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Met Tyr Tyr Cys
                 85                  90                  95

Thr Arg Asp Phe Asn Gly Tyr Ser Asp Phe Trp Gly Gln Gly Thr Thr
                100                 105                 110

Leu Thr Val Ser Ser
            115
```

```
<210> SEQ ID NO 59
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 59 aat gta cag ctg gta gag tct ggg gga ggc tta gtg cag cct gga ggg     48
Asn Val Gln Leu Val Glu Ser Gly Gly Gly Leu Val Gln Pro Gly Gly
 1               5                  10                  15 tcc cgg aaa ctc tcc tgt gca gcc tct gga ttc act ttc agt aac ttt     96
Ser Arg Lys Leu Ser Cys Ala Ala Ser Gly Phe Thr Phe Ser Asn Phe
             20                  25                  30 gga atg cac tgg gtt cgt cag gct cca gag aag ggt ctg gag tgg gtc    144
Gly Met His Trp Val Arg Gln Ala Pro Glu Lys Gly Leu Glu Trp Val
         35                  40                  45 gca tac att cgt agt ggc agt ggt acc atc tac tat tca gac aca gtg    192
Ala Tyr Ile Arg Ser Gly Ser Gly Thr Ile Tyr Tyr Ser Asp Thr Val
 50                  55                  60
```

```
aag ggc cga ttc acc atc tcc aga gac aat ccc aag aac acc ctg ttc      240
Lys Gly Arg Phe Thr Ile Ser Arg Asp Asn Pro Lys Asn Thr Leu Phe
 65                  70                  75                  80 ctg caa atg acc agt cta agg tct gag gac acg gcc atg tat tac tgt      288
Leu Gln Met Thr Ser Leu Arg Ser Glu Asp Thr Ala Met Tyr Tyr Cys
                 85                  90                  95 gca aga tcc tac tat gat ttc ggg gcc tgg ttt gct tac tgg ggc caa      336
Ala Arg Ser Tyr Tyr Asp Phe Gly Ala Trp Phe Ala Tyr Trp Gly Gln
            100                 105                 110 ggg act ctg gtc act gtc tct gca                                      360
Gly Thr Leu Val Thr Val Ser Ala
        115                 120

<210> SEQ ID NO 60
<211> LENGTH: 120
<212> TYPE: PRT
<213> ORGANISM: Mus sp.

<400> SEQUENCE: 60

Asn Val Gln Leu Val Glu Ser Gly Gly Gly Leu Val Gln Pro Gly Gly
  1               5                  10                  15

Ser Arg Lys Leu Ser Cys Ala Ala Ser Gly Phe Thr Phe Ser Asn Phe
             20                  25                  30

Gly Met His Trp Val Arg Gln Ala Pro Glu Lys Gly Leu Glu Trp Val
         35                  40                  45

Ala Tyr Ile Arg Ser Gly Ser Gly Thr Ile Tyr Tyr Ser Asp Thr Val
     50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Ser Tyr Tyr Asp Phe Gly Ala Trp Phe Ala Tyr Trp Gly Gln
            100                 105                 110

Gly Thr Leu Val Thr Val Ser Ala
        115                 120

<210> SEQ ID NO 61
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 61 gat atc gta atg acc cag tcc cac ctg agt atg agt acc tcc ctg gga       48
Asp Ile Val Met Thr Gln Ser His Leu Ser Met Ser Thr Ser Leu Gly
  1               5                  10                  15 gat cct gtg tca atc act tgc aag gcc tca cag gat gtg agc acc gtc       96
Asp Pro Val Ser Ile Thr Cys Lys Ala Ser Gln Asp Val Ser Thr Val
             20                  25                  30 gtt gct tgg tat cag cag aag ccc ggg caa tca ccc aga cgt ctc atc      144
Val Ala Trp Tyr Gln Gln Lys Pro Gly Gln Ser Pro Arg Arg Leu Ile
         35                  40                  45 tac tca gca tca tac cgt tac atc ggg gtg cct gac cga ttt act ggc      192
Tyr Ser Ala Ser Tyr Arg Tyr Ile Gly Val Pro Asp Arg Phe Thr Gly
     50                  55                  60 tct ggc gct ggc aca gat ttc acc ttt aca att agt tcc gtc cag gcc      240
Ser Gly Ala Gly Thr Asp Phe Thr Phe Thr Ile Ser Ser Val Gln Ala
 65                  70                  75                  80
```

```
gaa gac ctg gcc gtg tac tac tgc cag cag cac tac agt ccc cca tac      288
Glu Asp Leu Ala Val Tyr Tyr Cys Gln Gln His Tyr Ser Pro Pro Tyr
                85                  90                  95 act ttc ggg gga ggg act aag ctc gaa atc aaa cgt                      324
Thr Phe Gly Gly Gly Thr Lys Leu Glu Ile Lys Arg
            100                 105
```

<210> SEQ ID NO 62
<211> LENGTH: 108
<212> TYPE: PRT
<213> ORGANISM: Homo sapiens

<400> SEQUENCE: 62

```
Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
                20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
        50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105
```

<210> SEQ ID NO 63
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 63

```
gac att gtt atg gct caa agc cat ctg tct atg agc aca tct ctg gga      48
Asp Ile Val Met Ala Gln Ser His Leu Ser Met Ser Thr Ser Leu Gly
1               5                   10                  15 gat cct gtg tcc atc act tgc aaa gcc agt caa gac gtg tct aca gtt      96
Asp Pro Val Ser Ile Thr Cys Lys Ala Ser Gln Asp Val Ser Thr Val
                20                  25                  30 gtt gca tgg tat caa cag aag cca ggc cag tca ccc aga cgg ctc att      144
Val Ala Trp Tyr Gln Gln Lys Pro Gly Gln Ser Pro Arg Arg Leu Ile
            35                  40                  45 tac tca gct tct tac cga tac atc ggg gtc cct gac aga ttt aca ggt      192
Tyr Ser Ala Ser Tyr Arg Tyr Ile Gly Val Pro Asp Arg Phe Thr Gly
        50                  55                  60 agt ggg gcc ggt act gac ttc act ttt act atc tca tcc gta caa gcc      240
Ser Gly Ala Gly Thr Asp Phe Thr Phe Thr Ile Ser Ser Val Gln Ala
65                  70                  75                  80 gaa gac ctg gca gta tat tac tgc cag caa cat tat tcc cca ccc tac      288
Glu Asp Leu Ala Val Tyr Tyr Cys Gln Gln His Tyr Ser Pro Pro Tyr
                85                  90                  95 aca ttc ggc ggg ggt act aag ctg gaa att aaa cgt                      324
Thr Phe Gly Gly Gly Thr Lys Leu Glu Ile Lys Arg
            100                 105
```

<210> SEQ ID NO 64

```
<211> LENGTH: 108
<212> TYPE: PRT
<213> ORGANISM: Homo sapiens

<400> SEQUENCE: 64

Asp Ile Val Met Ala Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105

<210> SEQ ID NO 65
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 65 cag gta cag ctc gtt cag tcc ggc gcc gag gta gct aag cct ggt act      48
Gln Val Gln Leu Val Gln Ser Gly Ala Glu Val Ala Lys Pro Gly Thr
1               5                   10                  15 tcc gta aaa ttg tcc tgt aag gct tcc ggg tac aca ttt aca gac tac      96
Ser Val Lys Leu Ser Cys Lys Ala Ser Gly Tyr Thr Phe Thr Asp Tyr
            20                  25                  30 tgg atg cag tgg gta aaa cag cgg cca ggt cag ggc ctg gag tgg att     144
Trp Met Gln Trp Val Lys Gln Arg Pro Gly Gln Gly Leu Glu Trp Ile
        35                  40                  45 gga aca ata tat ccc ggc gac ggc gac aca ggc tat gcc cag aag ttt     192
Gly Thr Ile Tyr Pro Gly Asp Gly Asp Thr Gly Tyr Ala Gln Lys Phe
    50                  55                  60 caa ggc aag gca acc ctt act gct gat aaa tct tcc aag act gtc tac     240
Gln Gly Lys Ala Thr Leu Thr Ala Asp Lys Ser Ser Lys Thr Val Tyr
65                  70                  75                  80 atg cat ctg tct tcc ttg gca tct gag gat agc gct gtc tat tac tgt     288
Met His Leu Ser Ser Leu Ala Ser Glu Asp Ser Ala Val Tyr Tyr Cys
                85                  90                  95 gct agg ggg gac tac tat ggg tca aat tcc ctg gat tac tgg ggc cag     336
Ala Arg Gly Asp Tyr Tyr Gly Ser Asn Ser Leu Asp Tyr Trp Gly Gln
            100                 105                 110 ggc acc agt gtc acc gtg agc agc                                     360
Gly Thr Ser Val Thr Val Ser Ser
            115                 120

<210> SEQ ID NO 66
<211> LENGTH: 120
<212> TYPE: PRT
<213> ORGANISM: Homo sapiens

<400> SEQUENCE: 66

Gln Val Gln Leu Val Gln Ser Gly Ala Glu Val Ala Lys Pro Gly Thr
```

```
             1               5                  10                 15
            Ser Val Lys Leu Ser Cys Lys Ala Ser Gly Tyr Thr Phe Thr Asp Tyr
                           20                 25                 30

Trp Met Gln Trp Val Lys Gln Arg Pro Gly Gln Gly Leu Glu Trp Ile
                       35                 40                 45

Gly Thr Ile Tyr Pro Gly Asp Gly Asp Thr Gly Tyr Ala Gln Lys Phe
                   50                 55                 60

Gln Gly Lys Ala Thr Leu Thr Ala Asp Lys Ser Ser Lys Thr Val Tyr
             65                 70                 75                 80

Met His Leu Ser Ser Leu Ala Ser Glu Asp Ser Ala Val Tyr Tyr Cys
                           85                 90                 95

Ala Arg Gly Asp Tyr Tyr Gly Ser Asn Ser Leu Asp Tyr Trp Gly Gln
                          100                105                110

Gly Thr Ser Val Thr Val Ser Ser
                          115                120

<210> SEQ ID NO 67
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 67 gac acc gtg atg acc cag tcc ccc tcc acc atc tcc acc tct gtg ggc     48
Asp Thr Val Met Thr Gln Ser Pro Ser Thr Ile Ser Thr Ser Val Gly
 1               5                  10                 15 gac cgg gtg tcc atc acc tgt aag gcc tcc cag gtg gtg ggc tcc gcc     96
Asp Arg Val Ser Ile Thr Cys Lys Ala Ser Gln Val Val Gly Ser Ala
                 20                 25                 30 gtg gcc tgg tat cag cag aag cct ggc cag tcc cct aag ctg ctg atc    144
Val Ala Trp Tyr Gln Gln Lys Pro Gly Gln Ser Pro Lys Leu Leu Ile
             35                 40                 45 tac tgg gcc tcc acc cgg cat acc ggc gtg cct gac cgg ttc acc ggc    192
Tyr Trp Ala Ser Thr Arg His Thr Gly Val Pro Asp Arg Phe Thr Gly
         50                 55                 60 tcc ggc agc ggc acc gac ttc acc ctg acc atc tcc aac gtg cag tcc    240
Ser Gly Ser Gly Thr Asp Phe Thr Leu Thr Ile Ser Asn Val Gln Ser
 65                 70                 75                 80 gac gac ctg gcc gac tac ttc tgc cag cag tac aac tcc tac cct tac    288
Asp Asp Leu Ala Asp Tyr Phe Cys Gln Gln Tyr Asn Ser Tyr Pro Tyr
                 85                 90                 95 acc ttt ggc ggc gga aca aag ctg gag atc aag cgt                    324
Thr Phe Gly Gly Gly Thr Lys Leu Glu Ile Lys Arg
            100                105

<210> SEQ ID NO 68
<211> LENGTH: 108
<212> TYPE: PRT
<213> ORGANISM: Homo sapiens

<400> SEQUENCE: 68

Asp Thr Val Met Thr Gln Ser Pro Ser Thr Ile Ser Thr Ser Val Gly
 1               5                  10                 15

Asp Arg Val Ser Ile Thr Cys Lys Ala Ser Gln Val Val Gly Ser Ala
                 20                 25                 30

Val Ala Trp Tyr Gln Gln Lys Pro Gly Gln Ser Pro Lys Leu Leu Ile
             35                 40                 45
```

```
Tyr Trp Ala Ser Thr Arg His Thr Gly Val Pro Asp Arg Phe Thr Gly
         50                  55                  60

Ser Gly Ser Gly Thr Asp Phe Thr Leu Thr Ile Ser Asn Val Gln Ser
 65                  70                  75                  80

Asp Asp Leu Ala Asp Tyr Phe Cys Gln Gln Tyr Asn Ser Tyr Pro Tyr
                 85                  90                  95

Thr Phe Gly Gly Gly Thr Lys Leu Glu Ile Lys Arg
            100                 105
```

```
<210> SEQ ID NO 69
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 69
```

```
gac acc gtg atg acc cag tcc ccc tcc tcc atc tcc acc tcc atc ggc      48
Asp Thr Val Met Thr Gln Ser Pro Ser Ser Ile Ser Thr Ser Ile Gly
 1               5                  10                  15 gac cgg gtg tcc atc acc tgt aag gcc tcc cag gtg gtg ggc tcc gcc      96
Asp Arg Val Ser Ile Thr Cys Lys Ala Ser Gln Val Val Gly Ser Ala
             20                  25                  30 gtg gcc tgg tat cag cag aag cct ggc cag tcc cct aag ctg ctg atc     144
Val Ala Trp Tyr Gln Gln Lys Pro Gly Gln Ser Pro Lys Leu Leu Ile
         35                  40                  45 tac tgg gcc tcc acc cgg cat acc ggc gtg cct gcc cgg ttc acc ggc     192
Tyr Trp Ala Ser Thr Arg His Thr Gly Val Pro Ala Arg Phe Thr Gly
     50                  55                  60 tcc ggc agc ggc acc gac ttc acc ctg acc atc tcc aac gtg cag tcc     240
Ser Gly Ser Gly Thr Asp Phe Thr Leu Thr Ile Ser Asn Val Gln Ser
 65                  70                  75                  80 gag gac ctg gcc gac tac ttc tgc cag cag tac aac tcc tac cct tac     288
Glu Asp Leu Ala Asp Tyr Phe Cys Gln Gln Tyr Asn Ser Tyr Pro Tyr
                 85                  90                  95 acc ttt ggc ggc gga aca aag ctg gag atc aag cgt                     324
Thr Phe Gly Gly Gly Thr Lys Leu Glu Ile Lys Arg
            100                 105
```

```
<210> SEQ ID NO 70
<211> LENGTH: 108
<212> TYPE: PRT
<213> ORGANISM: Homo sapiens

<400> SEQUENCE: 70
```

```
Asp Thr Val Met Thr Gln Ser Pro Ser Ser Ile Ser Thr Ser Ile Gly
 1               5                  10                  15

Asp Arg Val Ser Ile Thr Cys Lys Ala Ser Gln Val Val Gly Ser Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Ala Arg Phe Thr Gly
     50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Asn Ser Tyr Pro Tyr
                 85                  90                  95

Thr Phe Gly Gly Gly Thr Lys Leu Glu Ile Lys Arg
            100                 105
```

```
<210> SEQ ID NO 71
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 71 gag gtg cag ctg gtg gag tct ggc ggc gga ctg gtg aag cct ggc ggc      48
Glu Val Gln Leu Val Glu Ser Gly Gly Gly Leu Val Lys Pro Gly Gly
1               5                   10                  15 tcc ctg agg ctg tcc tgt gag gcc tcc ggc ttc acc ttc tcc tcc tac      96
Ser Leu Arg Leu Ser Cys Glu Ala Ser Gly Phe Thr Phe Ser Ser Tyr
            20                  25                  30 acc ctg tcc tgg gtg agg cag acc cct ggc aag ggc ctg gag tgg gtg     144
Thr Leu Ser Trp Val Arg Gln Thr Pro Gly Lys Gly Leu Glu Trp Val
        35                  40                  45 gcc acc atc tcc atc ggc ggc agg tac acc tac tac cct gac tcc gtg     192
Ala Thr Ile Ser Ile Gly Gly Arg Tyr Thr Tyr Tyr Pro Asp Ser Val
    50                  55                  60 aag ggc cgg ttc acc atc tcc cgg gac aac gcc aag aac acc ctg tac     240
Lys Gly Arg Phe Thr Ile Ser Arg Asp Asn Ala Lys Asn Thr Leu Tyr
65                  70                  75                  80 ctg cag atg aac tcc ctg aag tcc gag gac acc gcc atg tac tac tgt     288
Leu Gln Met Asn Ser Leu Lys Ser Glu Asp Thr Ala Met Tyr Tyr Cys
                85                  90                  95 acc cgg gac ttc aac ggc tac tcc gac ttc tgg ggc cag ggc acc aca     336
Thr Arg Asp Phe Asn Gly Tyr Ser Asp Phe Trp Gly Gln Gly Thr Thr
            100                 105                 110 ctg acc gtg tcc tcc                                                  351
Leu Thr Val Ser Ser
        115

<210> SEQ ID NO 72
<211> LENGTH: 117
<212> TYPE: PRT
<213> ORGANISM: Homo sapiens

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Ser Tyr
            20                  25                  30

Thr Leu Ser Trp Val Arg Gln Thr Pro Gly Lys Gly Leu Glu Trp Val
        35                  40                  45

Ala Thr Ile Ser Ile Gly Gly Arg Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Thr Arg Asp Phe Asn Gly Tyr Ser Asp Phe Trp Gly Gln Gly Thr Thr
            100                 105                 110

Leu Thr Val Ser Ser
        115

<210> SEQ ID NO 73
<211> LENGTH: 36
```

<212> TYPE: DNA
<213> ORGANISM: Mus sp.

<400> SEQUENCE: 73
ggaggatcca tagacagatg ggggtgtcgt tttggc                                    36

<210> SEQ ID NO 74
<211> LENGTH: 32
<212> TYPE: DNA
<213> ORGANISM: Mus sp.

<400> SEQUENCE: 74
ggaggatccc ttgaccaggc atcctagagt ca                                        32

<210> SEQ ID NO 75
<211> LENGTH: 32
<212> TYPE: DNA
<213> ORGANISM: Mus sp.
<220> FEATURE:
<221> NAME/KEY: misc_feature
<222> LOCATION: (1)..(32)
<223> OTHER INFORMATION: mixed bases are defined as follows: H=A+T+C,
     S=G+C, Y=C+T, K=G+T, M=A+C, R=A+G, W=A+T, V = A+C+G, N = A+C+G+T

<400> SEQUENCE: 75
cttccggaat tcsargtnma gctgsagsag tc                                        32

<210> SEQ ID NO 76
<211> LENGTH: 35
<212> TYPE: DNA
<213> ORGANISM: Mus sp.
<220> FEATURE:
<221> NAME/KEY: misc_feature
<222> LOCATION: (1)..(35)
<223> OTHER INFORMATION: mixed bases are defined as follows: H=A+T+C,
     S=G+C, Y=C+T, K=G+T, M=A+C, R=A+G, W=A+T, V = A+C+G, N = A+C+G+T

<400> SEQUENCE: 76
cttccggaat tcsargtnma gctgsagsag tcwgg                                     35

<210> SEQ ID NO 77
<211> LENGTH: 31
<212> TYPE: DNA
<213> ORGANISM: Mus sp.
<220> FEATURE:
<221> NAME/KEY: misc_feature
<222> LOCATION: (1)..(31)
<223> OTHER INFORMATION: mixed bases are defined as follows: H=A+T+C,
     S=G+C, Y=C+T, K=G+T, M=A+C, R=A+G, W=A+T, V = A+C+G, N = A+C+G+T

<400> SEQUENCE: 77
ggagctcgay attgtgmtsa cmcarwctmc a                                         31

<210> SEQ ID NO 78
<211> LENGTH: 46
<212> TYPE: DNA
<213> ORGANISM: Mus sp.

<400> SEQUENCE: 78
tatagagctc aagcttggat ggtgggaaga tggatacagt tggtgc                         46

<210> SEQ ID NO 79
<211> LENGTH: 21
<212> TYPE: DNA
<213> ORGANISM: Mus sp.

<400> SEQUENCE: 79

```
atggagtcac agattcaggt c                                      21

<210> SEQ ID NO 80
<211> LENGTH: 32
<212> TYPE: DNA
<213> ORGANISM: Mus sp.

<400> SEQUENCE: 80
ttttgaattc cagtaacttc aggtgtccac tc                          32

<210> SEQ ID NO 81
<211> LENGTH: 17
<212> TYPE: PRT
<213> ORGANISM: Homo sapiens

<400> SEQUENCE: 81

Thr Ile Tyr Pro Gly Asp Gly Asp Thr Gly Tyr Ala Gln Lys Phe Gln
1               5                   10                  15

Gly
```

US 10,342,869 B2

COMPOSITIONS COMPRISING ANTI-CD38 ANTIBODIES AND LENALIDOMIDE

CROSS-REFERENCE TO RELATED APPLICATIONS

This application claims the benefit of U.S. Application No. 61/734,524, filed 7 Dec. 2012, and U.S. Application No. 61/769,247, filed 26 Feb. 2013, both of which are herein incorporated by reference in their entirety.

REFERENCE TO A SEQUENCE LISTING SUBMITTED VIA EFS-WEB

The content of the ASCII text file of the sequence listing named "20130404_034543_001P3_seq" which is 56.7 kb in size was created on 4 Apr. 2013 and electronically submitted via EFS-Web herewith the application is incorporated herein by reference in its entirety.

BACKGROUND OF THE INVENTION

1. Field of the Invention

The field of the present invention relates to anti-CD38 antibodies, lenalidomide, and cancer treatments.

2. Description of the Related Art

Multiple myeloma (MM) is a B cell malignancy. In MM, abnormal plasma cells accumulate in the bone marrow where they interfere with the production of normal cells. Current therapy of MM includes administration of proteasome inhibitors such as bortezomib, immunomodulatory drugs such as lenalidomide and thalidomide, and chemotherapy such as melphalan and prednisone. While these agents have improved survival in multiple myeloma, invariably resistance becomes problematic and patients succumb from their illness. Multiple myeloma thus remains ultimately fatal, with a median survival of approximately 3 to 5 years only.

CD38 is expressed on malignant plasma cells. CD38 is a 45 kD type II transmembrane glycolprotein with a long C-terminal extracellular domain and a short N-terminal cytoplasmic domain. The CD38 protein is a bifunctional ectoenzyme that can catalyze the conversion of $NAD^+$ into cyclic ADP-ribose (cADPR) and also hydrolyze cADPR into ADP-ribose. CD38 is up-regulated and has been implicated in many hematopoietic malignancies.

Thus, some proposed MM treatments include the administration of anti-CD38 antibodies. See, for example, WO 2012/041800; de Weers et al. (2011) J Immunol 186:1840-1848; and Van der Veer et al. (2011) Haematologica 96(2): 284-290. Unfortunately, like various drugs and chemotherapies, not all antibodies are the same and not all antibodies against the same antigen exhibit the same activities.

There is thus a need for new and efficacious treatments for extending survival and improving outcome of treatments of multiple myeloma, and more generally of blood cancers.

DESCRIPTION OF THE DRAWINGS

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

This invention is further understood by reference to the drawings wherein:

FIG. 4A shows the tumor volume of tumors in RPMI8226 models after treatment with the indicated dose of hu38SB19 at the indicated times (top arrows) and the indicated dose of lenalidomide at the indicated times (bottom arrows).

FIG. 6B shows the body weight of the H929 models after treatment with the indicated dose of hu38SB19 at the indicated times (arrows).

SUMMARY OF THE INVENTION

Figure 1A:
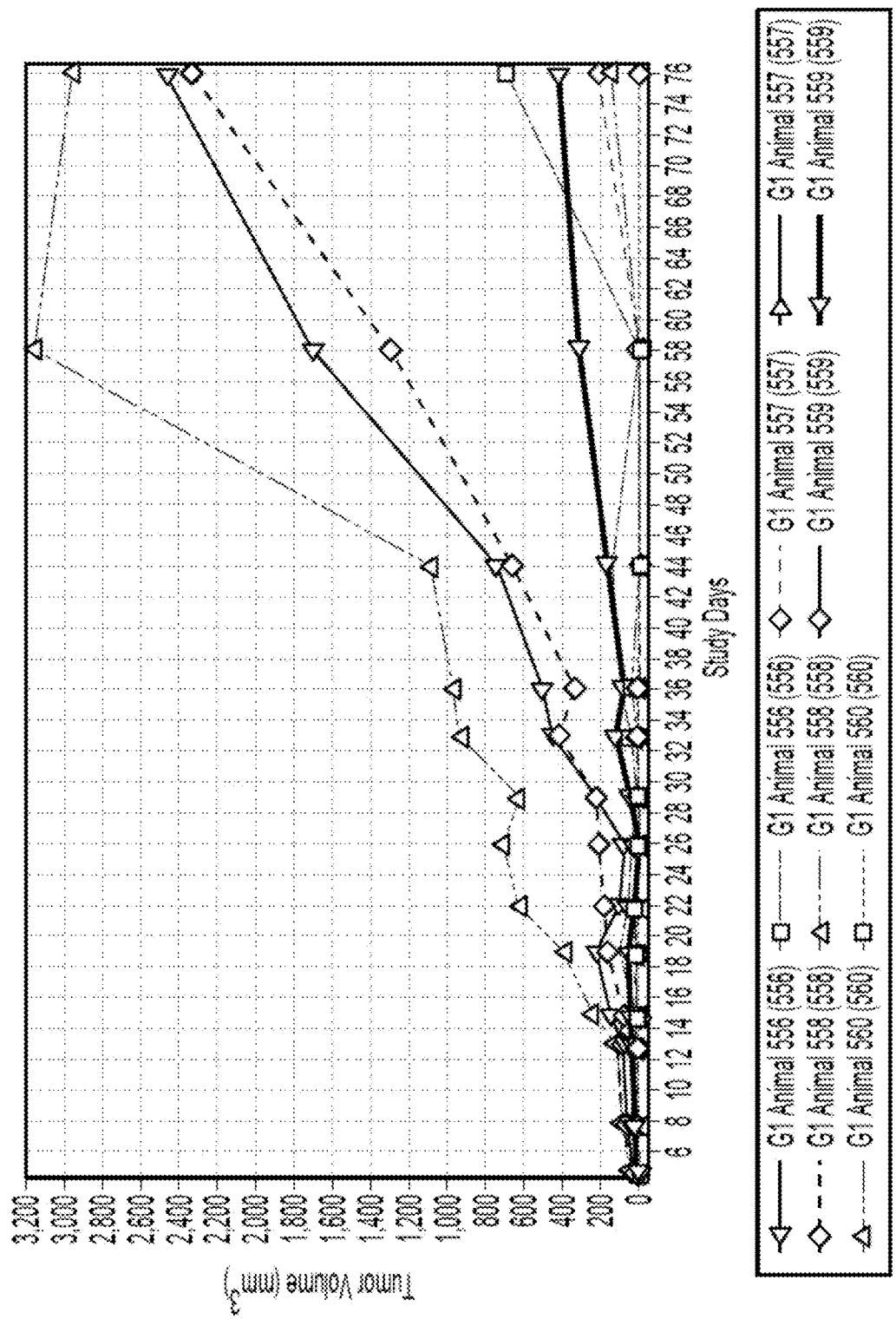
FIG. 1A shows the growth rate of tumors in xenograft models implanted with H929 cells (H929 models).
Figure 1B:
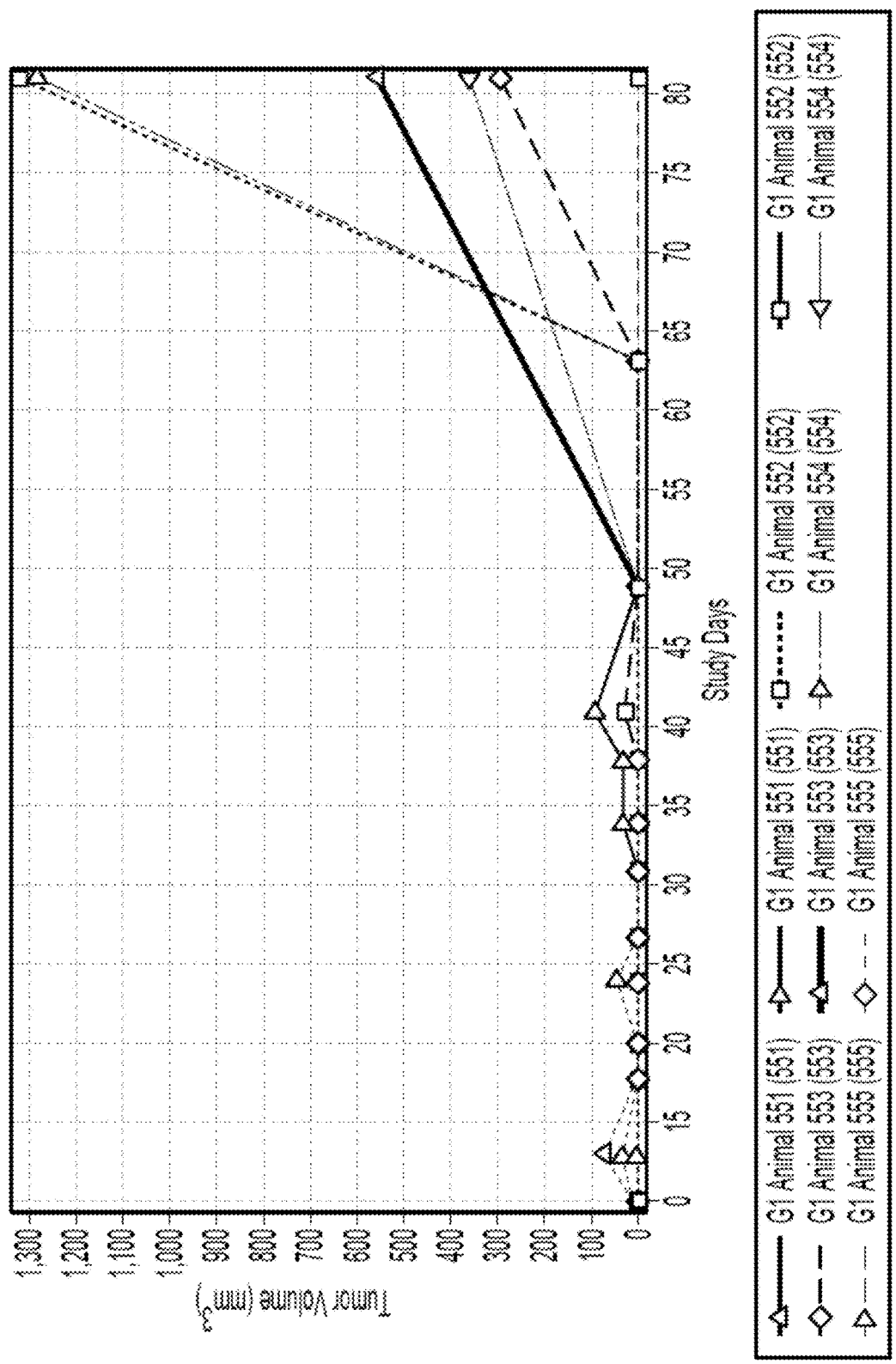
FIG. 1B shows the growth rate of tumors in xenograft models implanted with RPMI8226 cells (RPMI8226 models).
Figure 2A:
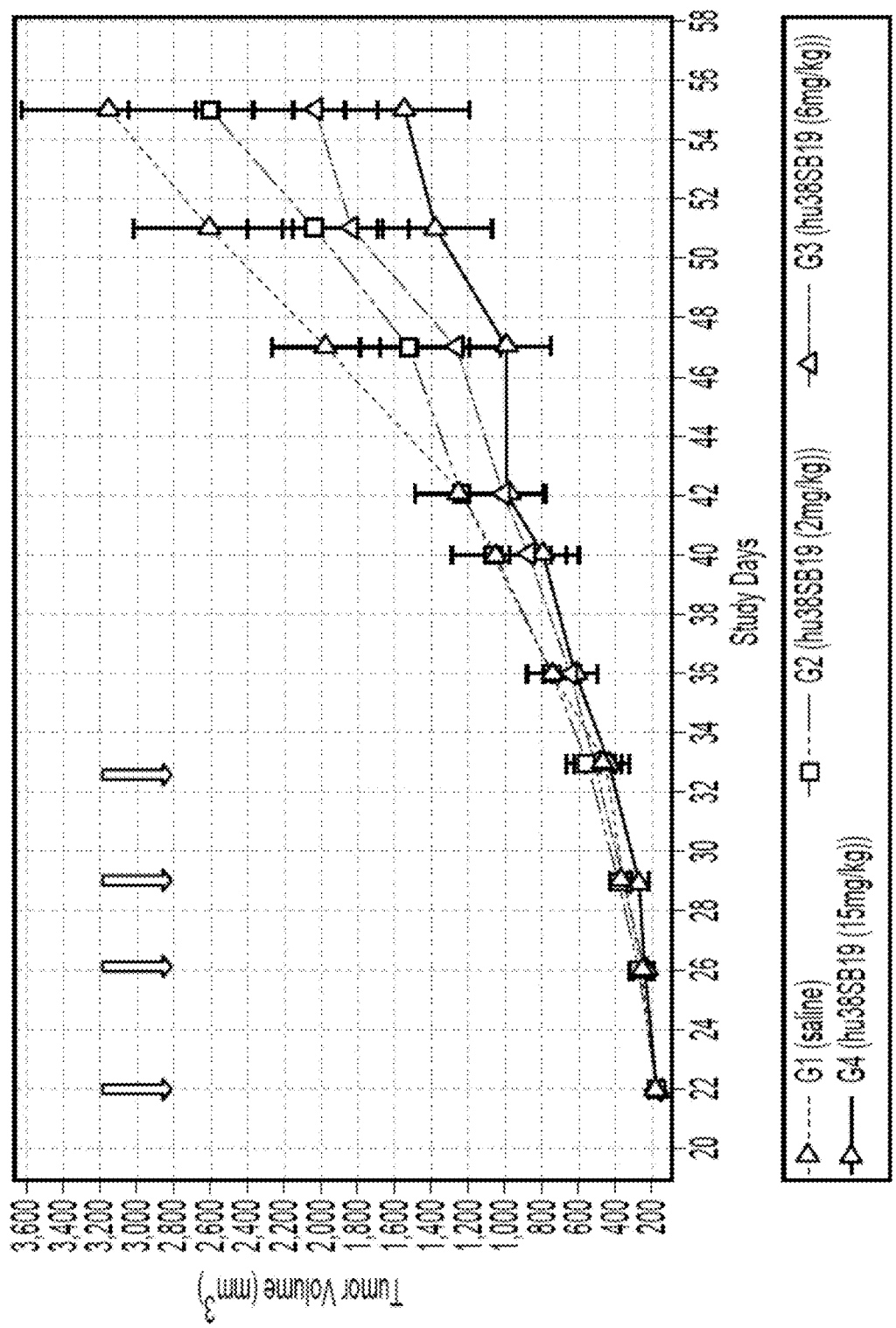
FIG. 2A shows the tumor volume of tumors in RPMI8226 models after treatment with the indicated dose of hu38SB19 at the indicated times (arrows).
Figure 2B:
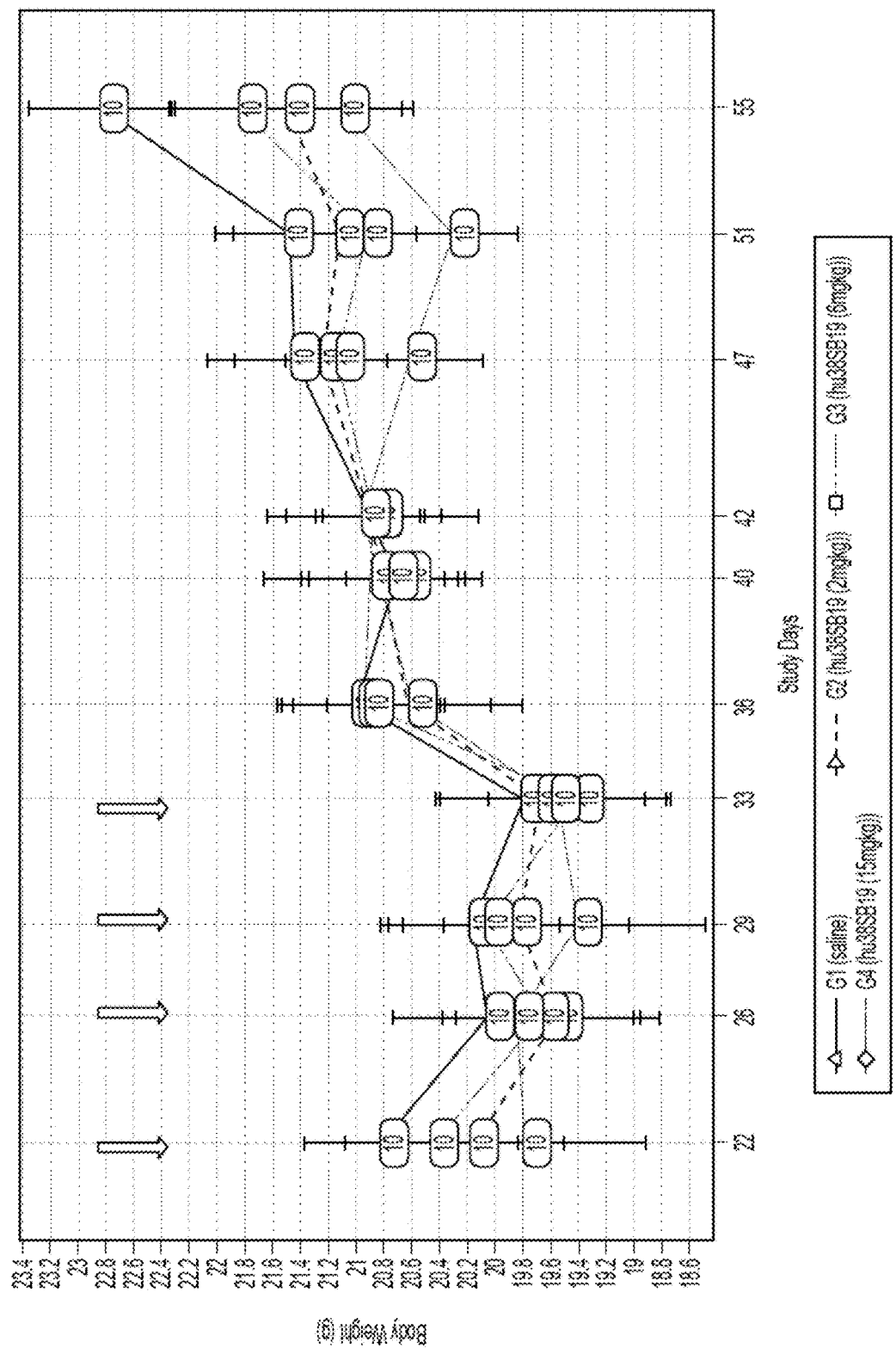
FIG. 2B shows the body weight of the RPMI8226 models after treatment with the indicated dose of hu38SB19 at the indicated times (arrows).
Figure 3A:
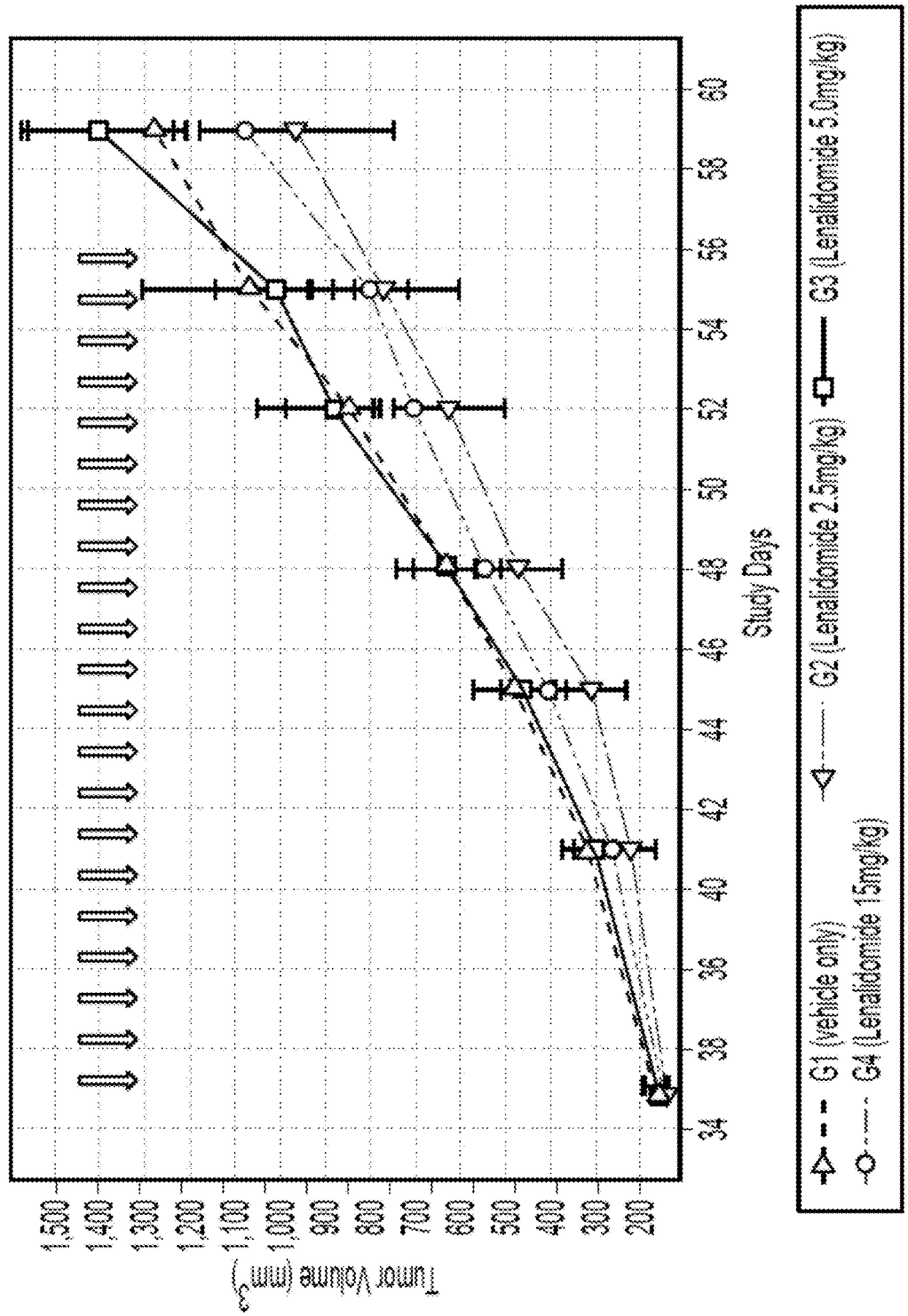
FIG. 3A shows the tumor volume of tumors in RPMI8226 models after treatment with the indicated dose of lenalidomide at the indicated times (arrows).
Figure 3B:
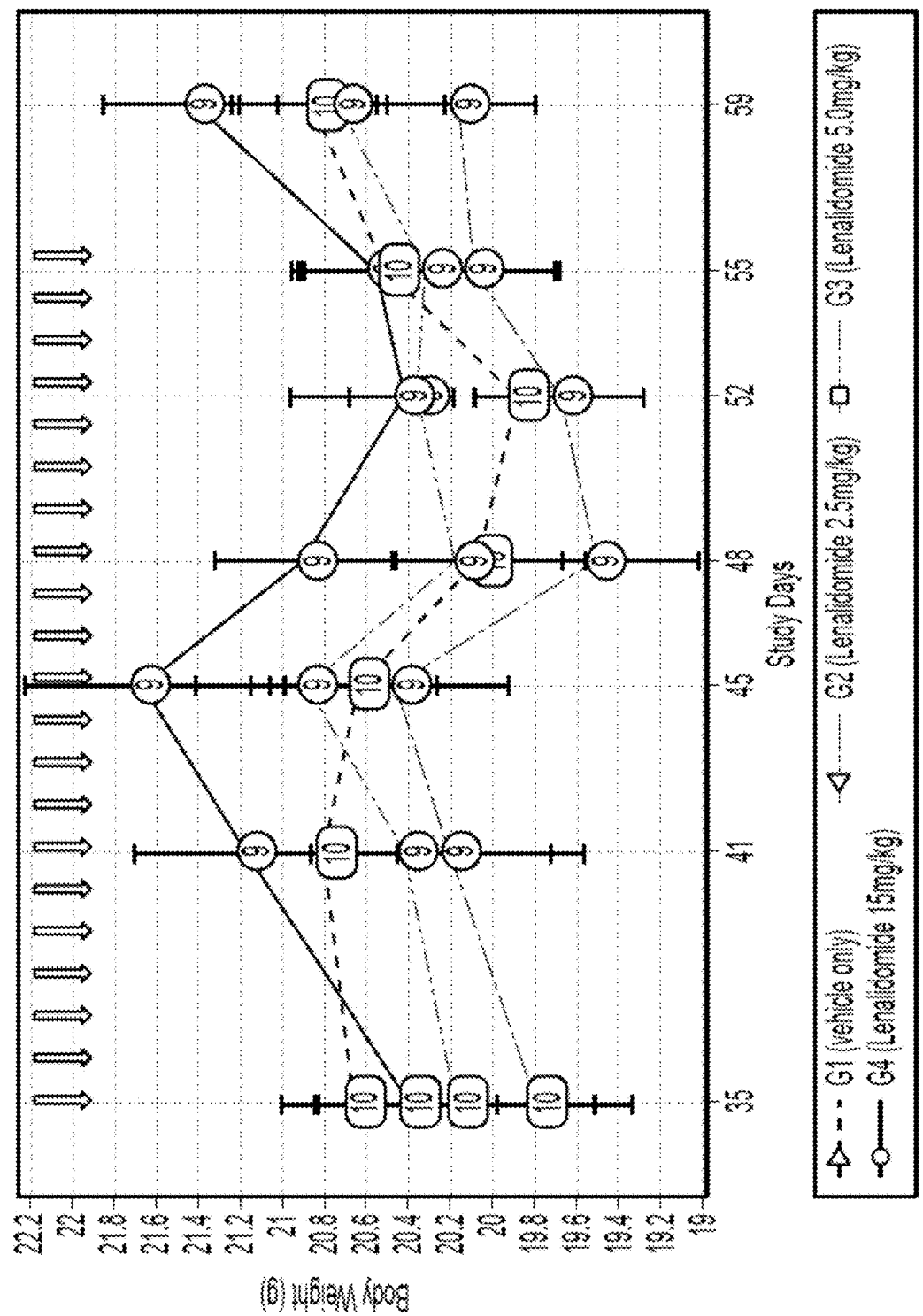
FIG. 3B shows the body weight of the RPMI8226 models after treatment with the indicated dose of lenalidomide at the indicated times (arrows).

In some embodiments, the present invention relates to a method of treating a cancer in a subject which comprises administering one or more anti-CD38 antibodies and one or more lenalidomide compounds to the subject. In some embodiments, the cancer is a hematological malignancy. In some embodiments, the cancer is multiple myeloma. In some embodiments, the cancer is a relapsed multiple myeloma or a refractory multiple myeloma. In some embodiments, the one or more lenalidomide compounds is lenalidomide. In some embodiments, the one or more anti-CD38 antibodies are administered in an effective amount, preferably a synergistic amount. In some embodiments, the one or more anti-CD38 antibodies and/or the one or more lenalidomide compounds are administered in a therapeutically effective amount. In some embodiments, at least one of the one or more anti-CD38 antibodies is capable of killing a CD38+ cell by apoptosis, antibody-dependent cell-mediated cytotoxicity (ADCC), and complement-dependent cytotoxicity (CDC). In some embodiments, the antibody is hu38SB19. In some embodiments, at least one of the one or more anti-CD38 antibodies comprises one or more complementarity-determining region having an amino acid sequence selected from the group consisting of SEQ ID NOs: 13, 14, 81, 15, 16, 17, 18, 1, 2, 3, 4, 5, 6, 7, 8, 9, 10, 11, 12, 19, 20, 21, 22, 23, 24, 25, 26, 27, 28, 29, 30, 31, 32, 33, 34, 35 and 36. In some embodiments, at least one of the one or more anti-CD38 antibodies is selected from the group consisting of: a) an antibody comprising a heavy chain comprising three sequential CDRs having amino acid sequences consisting of SEQ ID NOs: 13, 15 and either SEQ ID NO: 14 or SEQ ID NO: 81, and a light chain comprising three sequential CDRs having amino acid sequences consisting of SEQ ID NOs: 16, 17 and 18; b) an antibody comprising a heavy chain comprising three sequential CDRs having amino acid sequences consisting of SEQ ID NOs: 25, 26 and 27, and a light chain comprising three sequential CDRs having amino acid sequences consisting of SEQ ID NOs: 28, 29 and 30; c) an antibody comprising a heavy chain comprising three sequential CDRs having amino acid sequences consisting of SEQ ID NOs: 1, 2 and 3, and a light chain comprising three sequential CDRs having amino acid sequences consisting of SEQ ID NOs: 4, 5 and 6; d) an antibody comprising a heavy chain comprising three sequential CDRs having amino acid sequences consisting of SEQ ID NOs: 7, 8 and 9, and a light chain comprising three sequential CDRs having amino acid sequences consisting of SEQ ID NOs: 10, 11 and 12; e) an antibody comprising a heavy chain comprising three sequential CDRs having amino acid sequences consisting of SEQ ID NOs: 19, 20 and 21, and a light chain comprising three sequential CDRs having amino acid sequences consisting of SEQ ID NOs: 22, 23 and 24; and f) an antibody comprising a heavy chain comprising three sequential CDRs having amino acid sequences consisting of SEQ ID NOs: 31, 32 and 33, and a light chain comprising three sequential CDRs having amino acid sequences consisting of SEQ ID NOs: 34, 35 and 36. In some embodiments, the antibody comprises a heavy chain having a VH variable region represented by SEQ ID NO: 66, and a light chain having a VL variable region represented by either SEQ ID NO: 62 or SEQ ID NO: 64. In some embodiments, the antibody comprises a heavy chain having a VH variable region represented by SEQ ID NO: 72, and a light chain having a VL variable region represented by either SEQ ID NO: 68 or SEQ ID NO: 70. In some embodiments, the one or more anti-CD38 antibodies are administered intravenously. In some embodiments, the one or more lenalidomide compounds are administered orally. In some embodiments, the one or more anti-CD38 antibodies and the one or more lenalidomide compounds are administered sequentially. In some embodiments, the method further comprises administering a dexamethasone compound, preferably dexamethasone, to the subject. In some embodiments, the dexamethasone compound is administered orally. In some embodiments, the dexamethasone compound is administered at a low dose. In some embodiments, the one or more anti-CD38 antibodies, the one or more lenalidomide compounds, and the dexamethasone compound are administered sequentially. In some embodiments, the method further comprises administering an anti-coagulation agent to the subject. In some embodiments, the anti-coagulation agent is selected from the group consisting of aspirin, warfarin, and low molecular weight heparin. In some embodiments, the one or more anti-CD38 antibodies, the one or more lenalidomide compounds, and the anti-coagulation agent are administered sequentially.

In some embodiments, the present invention relates to a composition comprising a) at least one anti-CD38 antibody, preferably the antibody is capable of killing a CD38+ cell by apoptosis, antibody-dependent cell-mediated cytotoxicity (ADCC), and complement-dependent cytotoxicity (CDC); and b) at least one lenalidomide compound, preferably lenalidomide; and, optionally c) a dexamethasone compound, preferably dexamethasone; and, optionally d) an anti-coagulation agent. In some embodiments, the present invention relates to a composition comprising a) at least one anti-CD38 antibody; and b) at least one lenalidomide compound; and, optionally i) a dexamethasone compound; and/or ii) an anti-coagulation agent. In some embodiments, the antibody is capable of killing a CD38+ cell by apoptosis, antibody-dependent cell-mediated cytotoxicity (ADCC), and complement-dependent cytotoxicity (CDC). In some embodiments, the antibody is hu38SB19. In some embodiments, the lenalidomide compound is lenalidomide. In some embodiments, the dexamethasone compound is dexamethasone.

In some embodiments, the present invention is directed to a kit comprising a) a first composition comprising at least one anti-CD38 antibody, preferably the antibody is capable of killing a CD38+ cell by apoptosis, antibody-dependent cell-mediated cytotoxicity (ADCC), and complement-dependent cytotoxicity (CDC); and b) a second composition comprising at least one lenalidomide compound, preferably lenalidomide. In some embodiments, the compositions in the kit are packaged for sequential administration to a subject. In some embodiments, the antibody is hu38SB19. In some embodiments, the kit further includes a dexamethasone compound, preferably dexamethasone, and/or an anti-coagulation agent. In some embodiments, the dexamethasone compound and/or the anti-coagulation agent are packaged sequential administration to a subject.

In some embodiments, the present invention is directed to a kit comprising at least one anti-CD38 antibody capable of killing a CD38+ cell by apoptosis, antibody-dependent cell-mediated cytotoxicity (ADCC), and complement-dependent cytotoxicity (CDC), packaged together with a label having one or more messages that the at least one anti-CD38 antibody shall be administered in combination with lenalidomide, and optionally with dexamethasone and/or an anti-coagulation agent. In some embodiments, the antibody is hu38SB19. In some embodiments, the kit further includes a dexamethasone compound, preferably dexamethasone, and/or an anti-coagulation agent. In some embodiments, the dexamethasone compound and/or the anti-coagulation agent are packaged sequential administration to a subject.

In some embodiments, the present invention is directed to a combination of: (i) at least one anti-CD38 antibody, preferably the antibody is capable of killing a CD38+ cell by apoptosis, antibody-dependent cell-mediated cytotoxicity (ADCC), and complement-dependent cytotoxicity (CDC); and (ii) at least one lenalidomide compound, preferably lenalidomide; and, optionally (iii) a dexamethasone compound, preferably dexamethasone; and, optionally (iv) an anti-coagulation agent. In some embodiments, the present invention relates to a combination comprising a) at least one anti-CD38 antibody; and b) at least one lenalidomide compound; and, optionally i) a dexamethasone compound; and/or ii) an anti-coagulation agent. In some embodiments, the antibody is capable of killing a CD38+ cell by apoptosis, antibody-dependent cell-mediated cytotoxicity (ADCC), and complement-dependent cytotoxicity (CDC). In some embodiments, the antibody is hu38SB19. In some embodiments, the lenalidomide compound is lenalidomide. In some embodiments, the dexamethasone compound is dexamethasone. In some embodiments, the combination is for sequential use in the treatment of a hematological malignancy, preferably multiple myeloma.

In some embodiments, the present invention is directed to use of (i) at least one anti-CD38 antibody, preferably the antibody is capable of killing a CD38+ cell by apoptosis, antibody-dependent cell-mediated cytotoxicity (ADCC), and complement-dependent cytotoxicity (CDC); and (ii) at least one lenalidomide compound, preferably lenalidomide; and, optionally (iii) a dexamethasone compound, preferably dexamethasone; and, optionally (iv) an anti-coagulation agent for the treatment of a hematological malignancy, preferably multiple myeloma. In some embodiments, the present invention relates to use of a) at least one anti-CD38 antibody; and b) at least one lenalidomide compound; and, optionally i) a dexamethasone compound; and/or ii) an anti-coagulation agent for the treatment of a hematological malignancy, preferably multiple myeloma. In some embodiments, the antibody is capable of killing a CD38+ cell by apoptosis, antibody-dependent cell-mediated cytotoxicity (ADCC), and complement-dependent cytotoxicity (CDC). In some embodiments, the antibody is hu38SB19. In some embodiments, the lenalidomide compound is lenalidomide. In some embodiments, the dexamethasone compound is dexamethasone.

In some of the various embodiments of the present invention, the subject to be treated is mammalian. In some of the various embodiments of the present invention, the subject to be treated is a test animal such as a mouse. In some of the various embodiments of the present invention, the subject to be treated is human.

DETAILED DESCRIPTION OF THE INVENTION

The present invention relates to methods of treating a cancer in a subject which comprises administering one or more anti-CD38 antibodies and one or more lenalidomide jurors will compounds to the subject. As used herein, "treat" or "treating" means to alleviate symptoms, eliminate the causation of the symptoms either on a temporary or permanent basis, or to prevent or slow the appearance of symptoms of the named disorder or condition. As disclosed herein, the efficacy of a lenalidomide compound is considerably improved when administered in conjunction with one or more anti-CD38 antibodies according to the present invention. In fact, the administration of one or more anti-CD38 antibodies which exhibit (a) the capability of killing a $CD38^+$ cell by apoptosis, (b) antibody-dependent cell-mediated cytotoxicity (ADCC), and (c) complement-dependent cytotoxicity (CDC) is believed to considerably improve the efficacy of lenalidomide compounds in the treatment of hematological malignancies, including MM, to a degree that is unexpectedly more than other anti-CD38 antibodies which do not exhibit all three (a)-(c) activities. Therefore, in some embodiments, the one or more anti-CD38 antibodies are capable of (a) killing a $CD38^+$ cell by apoptosis, (b) antibody-dependent cell-mediated cytotoxicity (ADCC), and (c) complement-dependent cytotoxicity (CDC). In some embodiments, the one or more anti-CD38 antibodies and/or the one or more lenalidomide compounds are administered in a therapeutically effective amount. As used herein, a "therapeutically effective amount" of a substance refers to an amount of that substance that results in the alleviation of one or more symptoms, elimination of the causation of the symptoms either on a temporary or permanent basis, and/or the prevention or reduction in the appearance of symptoms of the named disorder or condition in the majority of subjects afflicted with and similarly treated for the named disease or disorder.

In some embodiments, the cancer is one in which CD38 is expressed by the malignant cells. In some embodiments, the cancer is a hematological malignancy of the blood, bone marrow, and/or lymph nodes. In some embodiments, the cancer is a blood cancer. Blood cancers include myeloma, lymphoma and leukemia. The blood cancer might, for instance, be selected from the group consisting of multiple myeloma, non-Hodgkin's lymphoma, Hodgkin's lymphoma, hairy cell leukemia, chronic lymphocytic leukemia, chronic myeloid leukemia, acute myeloid leukemia, and acute lymphocytic leukemia. In some embodiments, the cancer is multiple myeloma (MM). In some embodiments, the cancer is a relapse MM or refractory MM. As used herein, relapsed MM refers to clinically active MM after a period of remission and refractory MM refers to progressive or stable disease while being treated or progressive disease within 3 months of the last does of the prior treatment. See Dimopoulos et al. (2010) Eur J Haematology 88:1-15.

In some embodiments, the subject is mammalian, preferably human. In some embodiments, the subject is an adult human, e.g., at least 18 years. In some embodiments, the subject is in need of treatment for the cancer. In some embodiments, the subject has been diagnosed as having the cancer. In some embodiments, the cancer is in partial or complete remission, however, the one or more lenalidomide compounds and the one or more anti-CD38 antibodies are administered to the subject so as to reduce the likelihood of relapse. In some embodiments, the subject has a Karnofsky performance status equal or superior to 60%. The Karnofsky status runs from 100 to 0, where 100 is "perfect" health and 0 is death (Karnofsky and Burchenal, 1949, "The Clinical Evaluation of Chemotherapeutic Agents in Cancer." In: MacLeod CM (Ed), Evaluation of Chemotherapeutic Agents. Columbia Univ Press). In some embodiments, the subject has undergone at least one or two prior therapies for multiple myeloma, induction therapy being considered one prior therapy. In some embodiments, the subject exhibits evidence that either the cancer progressed while the subject underwent a prior therapy, or that the subject was refractory to the prior therapy.

In some embodiments, the anti-CD38 antibodies specifically bind CD38. In some embodiments, the anti-CD38 antibodies are raised against CD38 or an epitope thereof. In some embodiments, the anti-CD38 antibodies are monoclonal antibodies. In some embodiments, one or more of the anti-CD38 antibodies according to the present invention are monoclonal antibodies as described in WO 2008/047242, which is herein incorporated by reference in its entirety. In some embodiments, one or more of the anti-CD38 antibodies are monoclonal antibodies 38SB13, 38SB18, 38SB19, 38SB30, 38SB31, and 38SB39 as described in WO 2008/047242, which is herein incorporated by reference in its entirety. In some embodiments, the one or more anti-CD38 antibodies are capable of killing CD38$^+$ cells by three different cytotoxic mechanisms, induction of apoptosis, antibody-dependent cell-mediated cytotoxicity (ADCC), and complement-dependent cytotoxicity (CDC).

The term "antibody" is used herein in the broadest sense and includes monoclonal antibodies (including full length monoclonal antibodies) of any isotype such as IgG, IgM, IgA, IgD and IgE, polyclonal antibodies, multispecific antibodies, chimeric antibodies, and antibody fragments. As used herein, the prefix "anti-" when in conjunction with an antigen, indicates that the given antibody is reactive with the given antigen. An antibody reactive with a specific antigen can be generated by synthetic and/or recombinant methods such as selection of libraries of recombinant antibodies in phage or similar vectors, or by immunizing an animal with the antigen or an antigen-encoding nucleic acid.

A typical IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions outside of the CDRs are called the "framework regions". As used herein, "$V_H$" or "VH" refers to the variable region of an immunoglobulin heavy chain of an antibody, including the heavy chain of an Fv, scFv, dsFv, Fab, Fab' or F(ab')$_2$ fragment. Reference to "$V_L$" or "VL" refers to the variable region of the immunoglobulin light chain of an antibody, including the light chain of an Fv, scFv, dsFv, Fab, Fab' or F(ab')$_2$ fragment.

The antibodies according to the present invention may be, e.g., murine, chimeric, and/or humanized antibodies. As used herein, a "chimeric antibody" is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass. Methods for producing chimeric antibodies are known in the art. See e.g., Morrison, 1985, Science, 229: 1202; Oi et al., 1986, BioTechniques, 4: 214; Gillies et al., 1989, J. Immunol. Methods, 125: 191-202; U.S. Pat. Nos. 5,807,715; 4,816,567; and 4,816,397, which are incorporated herein by reference in their entireties. The term "humanized antibody", as used herein, refers to a chimeric antibody which contain minimal sequence derived from non-human immunoglobulin. The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modelling, statistical analysis and mutagenesis to alter the non-CDR surfaces of antibody variable regions to resemble the surfaces of known antibodies of the target host. The CDR grafting technology involves substituting the complementarity determining regions of, for example, a mouse antibody, into a human framework domain, e.g., see WO 92/22653. Humanized chimeric antibodies preferably have constant regions and variable regions other than the complementarity determining regions (CDRs) derived substantially or exclusively from the corresponding human antibody regions and CDRs derived substantially or exclusively from a mammal other than a human.

Strategies and methods for the resurfacing of antibodies, and other methods for reducing immunogenicity of antibodies within a different host, are disclosed in U.S. Pat. No. 5,639,641, which is hereby incorporated in its entirety by reference. Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, Molecular Immunology 28(4/5): 489-498; Studnicka G. M. et al., 1994, Protein Engineering, 7(6): 805-814; Roguska M. A. et al., 1994, PNAS, 91: 969-973), chain shuffling (U.S. Pat. No. 5,565,332), and identification of flexible residues (PCT/US2008/074381). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

In some embodiments, one or more of the anti-CD38 antibodies according to the invention are capable of killing a CD38$^+$ cell by apoptosis, antibody-dependent cell-mediated cytotoxicity (ADCC), and complement-dependent cytotoxicity (CDC). In some embodiments, one or more of the anti-CD38 antibodies according to the invention are capable of killing said CD38$^+$ cells by apoptosis even in the absence of stroma cells or stroma-derived cytokines. These activities can be assessed as described in WO 2008/047242, which is hereby incorporated by reference in its entirety.

In some embodiments according to the invention, one or more anti-CD38 antibodies are selected from the group consisting of 38SB13, 38SB18, 38SB19, 38SB30, 38SB31, 38SB39, and antibodies cross-competing with 38SB13, 38SB18, 38SB19, 38SB30, 38SB31 or 38SB39. The hybridoma cell lines producing the 38SB13, 38SB18, 38SB19, 38SB30, 38SB31, and 38SB39 murine anti-CD38 antibodies have been deposited at the American Type Culture Collection (10801 University Bld, Manassas, Va., 20110-2209, USA), on 21 Jun. 21 2006, under the deposit numbers PTA-7667, PTA-7669, PTA-7670, PTA-7666, PTA-7668, and PTA-7671, respectively (as described in WO 2008/047242, which is herein incorporated by reference in its entirety).

As disclosed herein, references to SEQ ID NOs refers to the sequences set forth in the Sequence Listing submitted herewith and also as recited in WO 2008/047242, which is herein incorporated by reference in its entirety. In some embodiments, the anti-CD38 antibodies according to the present invention may, for instance, comprise a heavy chain comprising three sequential CDRs having amino acid sequences represented by SEQ ID NOs: 1, 2, and 3, and a light chain comprising three sequential CDRs having amino acid sequences represented by SEQ ID NOs: 4, 5, and 6. An example of such an antibody is the 38SB13 antibody, which comprises a heavy chain having a $V_H$ variable region represented by SEQ ID NO: 50, and a light chain having a $V_L$ variable region represented by SEQ ID NO: 38.

In some embodiments, the anti-CD38 antibodies according to the present invention may, for instance, comprise a heavy chain comprising three sequential CDRs having amino acid sequences represented by SEQ ID NOs: 7, 8, and 9, and a light chain comprising three sequential CDRs having amino acid sequences represented by SEQ ID NOs: 10, 11, and 12. An example of such an antibody is the 38SB18 antibody, which comprises a heavy chain having a $V_H$ variable region represented by SEQ ID NO: 52 and a light chain having a $V_L$ variable region represented by SEQ ID NO: 40.

In some embodiments, the anti-CD38 antibodies according to the present invention may, for instance, comprise a heavy chain comprising three sequential CDRs having amino acid sequences represented by SEQ ID NO: 13, SEQ ID NO: 15 and either SEQ ID NO: 14 or SEQ ID NO: 81, and a light chain comprising three sequential CDRs having amino acid sequences represented by SEQ ID NOs: 16, 17, and 18. An example of such an antibody is the 38SB19 antibody, which comprises a heavy chain having a $V_H$ variable region represented by SEQ ID NO: 54 and a light chain having a $V_L$ variable region represented by SEQ ID NO: 42. Specific examples of humanized versions of 38SB19 (hu38SB19) include antibodies comprising a heavy chain having a $V_H$ variable region represented by SEQ ID NO: 66, and a light chain having a $V_L$ variable region represented by either SEQ ID NO: 62 or SEQ ID NO: 64. hu38SB19 is a humanized anti-CD38 antibody currently undergoing clinical evaluation in CD38-positive hematologic malignancies, including multiple myeloma. Previous and current studies demonstrate that the anti-myeloma activity associated with this agent involve mechanisms of ADCC, and CDC, as well as novel, direct apoptotic and anti-ADP-ribosyl cyclase activity. See Marie-Cecile Wetzel, Celine Nicolazzi, François Vallee, et al. hu38SB19: characterization of a potent phase I humanized anti-CD38 antibody for the treatment of multiple myeloma and other hematologic malignancies. AACR Annual Meeting 2013, Abstract #4735.

In some embodiments, the anti-CD38 antibodies according to the present invention may, for instance, comprise a heavy chain comprising three sequential CDRs having amino acid sequences represented by SEQ ID NOs: 19, 20, and 21, and a light chain comprising three sequential CDRs having amino acid sequences represented by SEQ ID NOs: 22, 23, and 24. An example of such an antibody is the 38SB30 antibody, which comprises a heavy chain having a $V_H$ variable region represented by SEQ ID NO: 56 and a light chain having a $V_L$ variable region represented by SEQ ID NO: 44.

In some embodiments, the anti-CD38 antibodies according to the present invention may, for instance, comprise a heavy chain comprising three sequential CDRs having amino acid sequences represented by SEQ ID NOs: 25, 26, and 27, and a light chain comprising three sequential CDRs having amino acid sequences represented by SEQ ID NOs: 28, 29, and 30. An example of such an antibody is the 38SB31 antibody, which comprises a heavy chain having a $V_H$ variable region represented by SEQ ID NO: 58 and a light chain having a $V_L$ variable region represented by SEQ ID NO: 46. Specific examples of humanized versions of 38SB31 (hu38SB31) include antibodies comprising a heavy chain having a $V_H$ variable region represented by SEQ ID NO: 72, and a light chain having a $V_L$ variable region represented by either SEQ ID NO: 68 or SEQ ID NO: 70.

In some embodiments, the anti-CD38 antibodies according to the present invention may, for instance, comprise a heavy chain comprising three sequential CDRs having amino acid sequences represented by SEQ ID NOs: 31, 32 and 33, and a light chain comprising three sequential CDRs having amino acid sequences represented by SEQ ID NOs: 34, 35, and 36. An example of such an antibody is the 38SB39 antibody, which comprises a heavy chain having a $V_H$ variable region represented by SEQ ID NO: 60 and a light chain having a $V_L$ variable region represented by SEQ ID NO: 48.

In some embodiments, the anti-CD38 antibodies according to the invention are humanized antibodies consisting of two identical heavy chains and of two identical light chains, wherein each chain consists of one constant region and of one variable region.

As used herein, a "lenalidomide compound" refers to lenalidomide ((RS)-3-(4-amino-1-oxo-3H-isoindol-2-yl)piperidine-2,6-dione) and lenalidomide derivatives. As used herein, "lenalidomide derivatives" refers to compounds which have 4-amino-1-oxo-3H-2-isoindolyl, i.e.,

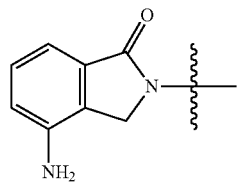

which may or may not be substituted, as part of its structural formula. For example, "lenalidomide derivatives" include those having the following formula:

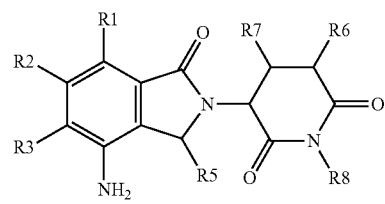

wherein R1-R8 are each independently H, a halogen, an alkyl, an alkoxy, amino, or an alkylamine, and wherein R5 may additionally be a double bonded oxygen. In some embodiments, R5 is H. In some embodiments, R8 is H. In some embodiments, both R5 and R8 are H.

In some embodiments, the one or more anti-CD38 antibodies are administered in an effective amount. As used herein, an effective amount of the one or more anti-CD38 antibodies is an amount which results in an additive or a synergistic effect with the one or more lenalidomide compounds. As used herein, a "synergistic amount" is one that results in a synergistic effect. As used herein, a "synergistic effect" refers to the effect of the combination of the one or more anti-CD38 antibodies and the one or more lenalidomide compounds which is more than their expected additive effect. In some embodiments, the one or more anti-CD38 antibodies are administered before, during, and/or after the administration of the one or more lenalidomide compounds. In some embodiments, the one or more anti-CD38 antibodies and the one or more lenalidomide compounds are co-administered in the form of a single composition, e.g., as a mixture.

Thus, in some embodiments, the present invention is directed to compositions comprising a mixture of at least one anti-CD38 antibody and at least one lenalidomide compound. In some embodiments, the mixture comprises the at least one anti-CD38 antibody in an amount that results in an additive or a synergistic effect with the at least one lenalidomide compound in a subject when both are administered. In some embodiments, the at least one anti-CD38 antibody in the mixture is one which is capable of killing a $CD38^+$ cell by apoptosis, antibody-dependent cell-mediated cytotoxicity (ADCC), and complement-dependent cytotoxicity (CDC); and at least one lenalidomide compound.

For the purposes of the present invention, the methods and compositions of the present invention are not exclusively limited to those which are obtained by physical association of the anti-CD38 antibodies and the lenalidomide compound, but also to those which permit a separate administration, which can be simultaneous or spaced out over a period of time. Thus, in some embodiments, the present invention is directed to a first composition comprising the one or more anti-CD38 antibodies, and a second composition comprising one or more lenalidomide compounds. In some embodiments, the at least one anti-CD38 antibody is one which is capable of killing a $CD38^+$ cell by apoptosis, antibody-dependent cell-mediated cytotoxicity (ADCC), and complement-dependent cytotoxicity (CDC); and at least one lenalidomide compound. In some embodiments, the amount of the one or more anti-CD38 antibodies provided in the first composition is one that results in an additive or a synergistic effect with the at least one lenalidomide compound in the second composition in a subject when both are administered.

In some embodiments, the first and second compositions may be packaged in a kit. Thus, in some embodiments, the present invention is directed to kits which comprise a first composition comprising the one or more anti-CD38 antibodies, and a second composition comprising one or more lenalidomide compounds. In some embodiments, the first and second composition may be mixed together before administering to a subject. In some embodiments, the first and second compositions, may be administered either simultaneously or sequentially (i.e., spaced out over a period of time) so as to obtain the maximum efficacy, additivity, synergy, or a combination thereof of the combination. In some embodiments, the present invention is directed to kits comprising at least one anti-CD38 antibody packaged together with a label having one or more messages that the anti-CD38 antibody shall or might be administered in combination with lenalidomide and optionally with dexamethasone and/or an anti-coagulation agent. The kits according to the present invention may further comprise one or more messages that the antibody shall or might be administered to a subject suffering from a blood cancer such as multiple myeloma (e.g., relapsed or refractory multiple myeloma). In some embodiments, the one or more anti-CD38 antibodies in the kits of the present invention are those which are capable of killing a $CD38^+$ cell by apoptosis, antibody-dependent cell-mediated cytotoxicity (ADCC), and complement-dependent cytotoxicity (CDC).

In some embodiments, the compositions of the present invention are pharmaceutical compositions. As used herein, the term "pharmaceutical composition" refers to a composition comprising at least one active principle (e.g., an anti-CD38 antibody or a lenalidomide compound) and at least one pharmaceutically acceptable carrier. Pharmaceutically acceptable carriers are well known to the skilled in the art, and usually depend on the chosen route of administration. Pharmaceutical compositions according to the present invention may be provided in any form or formulation that is suitable for the chosen route of administration, such as e.g., a solution in case of an intravenous route of administration, e.g., capsules, pills or tablets in case of an oral route of administration, etc.

The dosage regimen of the active principles and of the pharmaceutical composition described herein can be chosen by prescribing physicians, based on their knowledge of the art, including information published by regulatory authorities. For example, lenalidomide is typically administered orally. According to the European Medicines Agency (EMA), the recommended dose of lenalidomide is 25 mg orally once daily on days 1-21 of repeated 28-day cycles. Since, however, co-administration of the one or more anti-CD38 antibodies and the one or more lenalidomide compounds results in an additive or a synergistic effect, the dosing of the lenalidomide compound may be adjusted accordingly, e.g., the dose changed and/or the dosing schedule modified. Of course, prescribing physicians might reconsider which dose and schedule to use depending on the condition and disease status of the patient and based upon clinical and laboratory findings.

As lenalidomide is approved for the treatment of MM in combination with dexamethasone, the methods and compositions of the present invention may further include dexamethasone, which is member of the glucocorticoid class of steroid drugs, and acts as an anti-inflammatory and immunosuppressant. Thus, in some embodiments, the treatment methods of the present invention further comprise administering a dexamethasone compound to the subject being treated with the one or more anti-CD38 antibodies and the one or more lenalidomide compounds. Similarly, the compositions and kits of the present invention which comprise the one or more anti-CD38 antibodies and/or the one or more lenalidomide compounds may further comprise a dexamethasone compound. As used herein, a "dexamethasone compound" refers to dexamethasone ((8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one) and dexamethasone derivatives. As used herein, a "dexamethasone derivative" refers to a compound having the following structural formula:

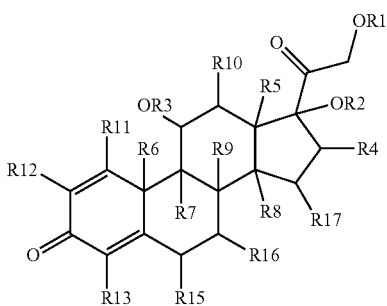

wherein R1-R17 are each independently H, a halogen, an alkyl, an alkoxy, amino, or an alkylamine. In some preferred embodiments, R1-R3 are H. In some preferred embodiments, R4-R6 are methyl. In some preferred embodiments, R7 is a halogen, preferably fluorine. In some preferred embodiments, R8 is H. In some preferred embodiments, R1-R3 are H, R4-R6 are methyl, R7 is a halogen, preferably fluorine, and R8 is H.

In some embodiments, the dexamethasone compound may be administered orally. According to the EMA, when combined with lenalidomide, the recommended dose of dexamethasone is 40 mg orally once daily on days 1-4, 9-12, and 17-20 of each 28-day cycle for the first 4 cycles of therapy and then 40 mg once daily on days 1-4 every 28 days. Prescribing physicians might also re-evaluate which dose of dexamethasone to use upon clinical and laboratory findings.

However, in some embodiments, the dexamethasone compound may be administered at a lower dose than the dose recommended for dexamethasone by the EMA. Indeed, recent studies suggest that lenalidomide plus low dose dexamethasone is associated with better short-term overall survival and with lower toxicity than lenalidomide plus high-dose dexamethasone in patients with newly diagnosed myeloma (Rajkumar et al. (2010) Lancet Onco. 11:29-37). Therefore, in some embodiments of the present invention, the dexamethasone compound is administered at low dose. The term "low dose" in this context refers to any dose that is at least 20, 30 or 40% lower that the dose of dexamethasone recommended by EMA at the date of first marketing approval of the lenalidomide plus dexamethasone combination. For instance, administration of 40 mg of dexamethasone on days 1, 8, 15, and 22 of a 28-day cycle is considered as a low dose of dexamethasone.

In some embodiments, the methods and compositions of the present invention may further include an anti-coagulation agent, such as e.g., aspirin, warfarin, low molecular weight heparin or equivalent anti-platelet therapeutic. For example, in some embodiments, the treatment methods of the present invention further comprise administering an anti-coagulation agent to the subject being treated with the one or more anti-CD38 antibodies and the one or more lenalidomide compounds. Similarly, the compositions and kits of the present invention which comprise the one or more anti-CD38 antibodies and/or the one or more lenalidomide compounds may further comprise an anti-coagulation agent.

The compositions of the present invention may be used as a medicament and/or for use in the manufacture of a medicament. In some embodiments, the compositions of the present invention may be used as a medicament and/or for use in the manufacture of a medicament for use in the treatment of a cancer such as a hematological malignancy of the blood, bone marrow, and/or lymph nodes, preferably a blood cancer.

Several documents are cited throughout the text of this specification. Each of the documents herein (including any journal article or abstract, published or unpublished patent application, issued patent, manufacturer's specifications, instructions, etc.) are hereby incorporated by reference. However, there is no admission that any document cited herein is indeed prior art in respect of the present invention.

The following examples are intended to illustrate but not to limit the invention.

EXAMPLES hu38SB19 was provided in solution at 5 mg/ml, stored at 4° C. It was diluted into sterile saline in preparation for dosing, stored at 4° C. and used within 10 days of dilution.

Lenolidomide was obtained from AK Scientific Inc. (Mountain View, Calif.) and prepared as a suspension in 1% (w/v) carboxymethyl cellulose (Sigma). Preparation was made using a mortar and pestle to generate a slurry suspension in the vehicle, diluted to the appropriate concentration, and used for dosing by oral gavage.

Example 1

Effect of the Administration of Both Anti-CD38 Antibody and Lenalidomide in a Mice Model of MM These studies under this Example were done under approval of the UCSF IACUC.

The subcutaneous multiple myeloma (MM) xenograft mouse models were established using H929 and RPMI8226 cell lines. Specifically, 5-6 week old female Balb/c Scid mice were obtained from Jackson Lab. Mice were housed for 7-10 days prior to implantation. Mice were housed in a dedicated room in the UCSF Mt Zion Animal Barrier Facility. NCI-H929 and RPMI-8226 cells were obtained from the German Collection of Microorganisms and Cell Cultures, DSMZ, (Deutsche Sammlung von Mikroorganismen and Zellkulturen), and grown in sterile suspension culture in T225 flasks as follows: NCI-H929:RPMI1640+ 20% FBS+4 mM L-glutamine+1 mM sodium pyruvate+50 µM mercaptoethanol. RPMI-8226:RPMI1640+10% FBS+4 mM L-glutamine.

At the time of implantation, mice were shaved on the right flank and shoulder region and anesthetized with ip avertin. MM cells suspended in serum free RPMI 1640 media diluted 1:1 with Matrigel (BD) at a concentration of $1 \times 10^8$ cells per ml were injected sc into the right flank in 100 µL volume ($1 \times 10^7$ cells) using a 1 ml syringe and 25 g needle. Mice were monitored twice weekly for the appearance of tumors and once tumors were visible, measurements were collected twice weekly for body weight and tumor volume. Electronic balance and calipers were used and data was collected directly into a study management program (Study Director). When the mean tumor volume reached about 150-200 mm³, the mice were distributed into treatment groups of 8-10 mice per groups and dosing was begun.

The dosing schedule was hu38SB19 was 2×/wk×2 wk (iv lateral tail vein) and lenalidomide was qdx7×3 wk (po) (orally, one dose per day, 7 days a week, for 21 days). Dose levels for use in combination studies are as follows:

| Cell Type | Lenalidomide | hu38SB19 |
|---|---|---|
| H929 | 1 mpk | 0.5 mpk |
| RPMI8226 | 15 mpk | 15 mpk | mpk = mg per kg body weight

Data were collected using electronic balance and calipers using a study management application called StudyLog (Study Director). Graphs are taken directly from the application. The experimental results are provided in FIGS. 1A-11B.

Based on the single agent results of hu38SB19 and lenalidomide in RPMI-8226 and NCI-H929 multiple myeloma xenograft models, NCI-H929 appears to be a more sensitive model to both agents while RPMI-8226 seems to be more resistant to the treatments even at the highest doses tested (FIGS. 1-3, 5-8). Therefore in the combination studies, a suboptimal dose for each agent was chosen to evaluate the activity of the combination treatment (lenalidomide+ hu38SB19) in the NCI-H929 model while higher doses of lenalidomide and hu38SB19 were tested in the RPMI-8226 model.

Antitumor activity was determined according to NCI standards based on the ratio of the median tumor volume change of the treated/median tumor volume change of the control×100 (% $\Delta T/\Delta C$). Low numerical values for $\Delta T/\Delta C$ describe stronger anti-tumor activity. Anti-tumor activity is defined as $\Delta T/\Delta C \leq 40\%$ at minimum. $\Delta T/\Delta C < 10\%$ is considered high anti-tumor activity.

Figure 4B:
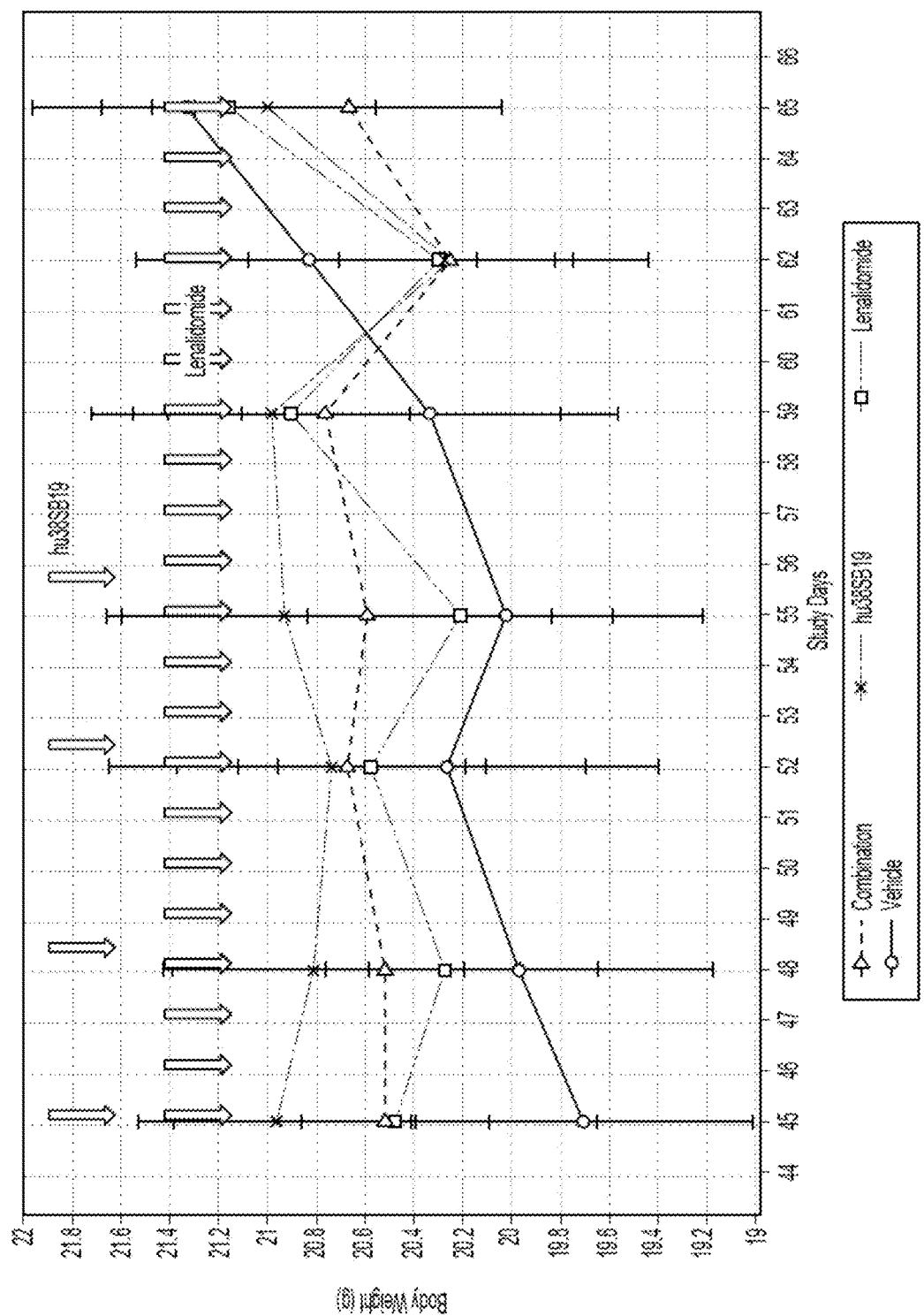
FIG. 4B shows the body weight of the RPMI8226 models after treatment with the indicated dose of hu38SB19 at the indicated times (top arrows) and the indicated dose of lenalidomide at the indicated times (bottom arrows).
Figure 5A:
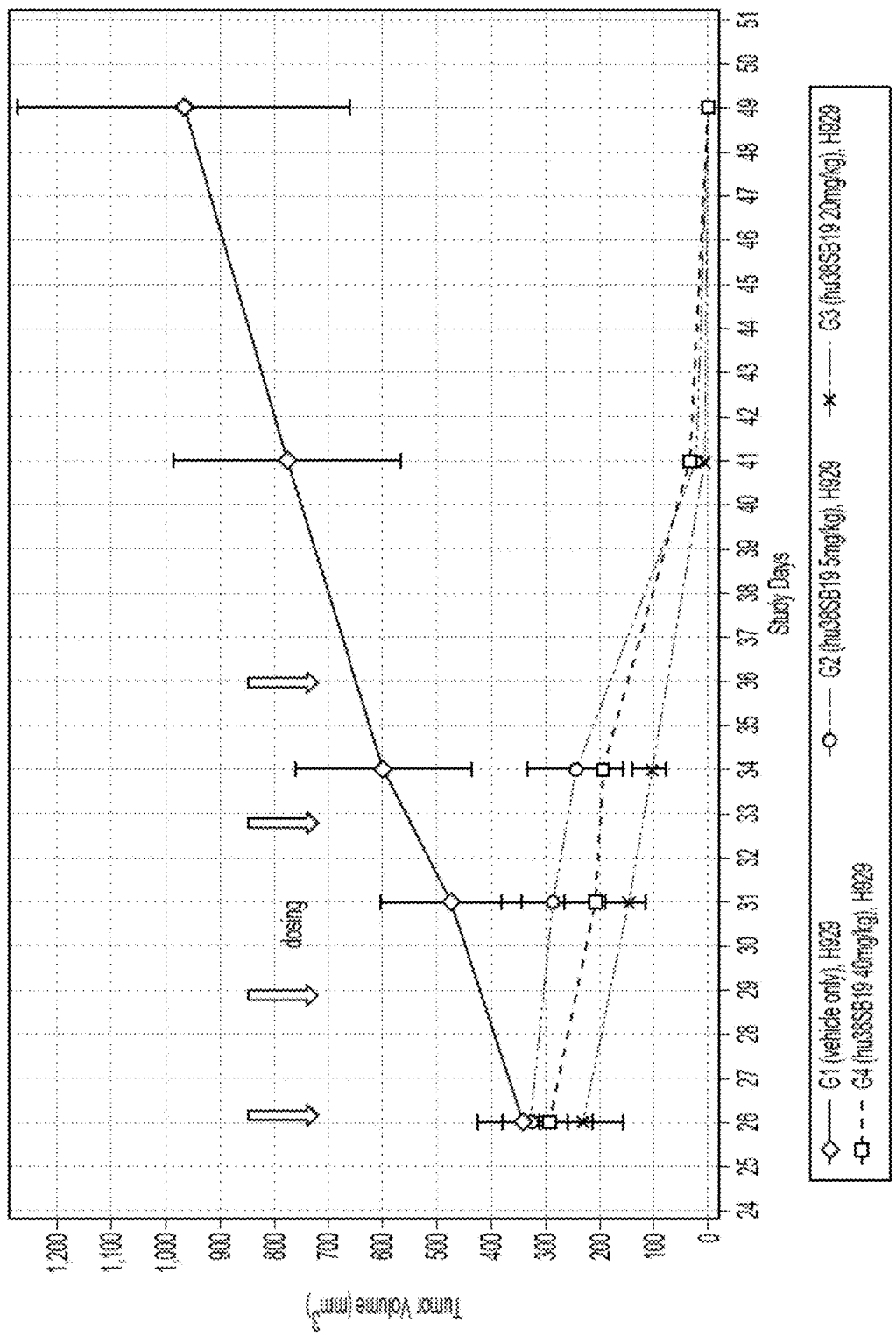
FIG. 5A shows the tumor volume of tumors in H929 models after treatment with the indicated dose of hu38SB19 at the indicated times (arrows).
Figure 5B:
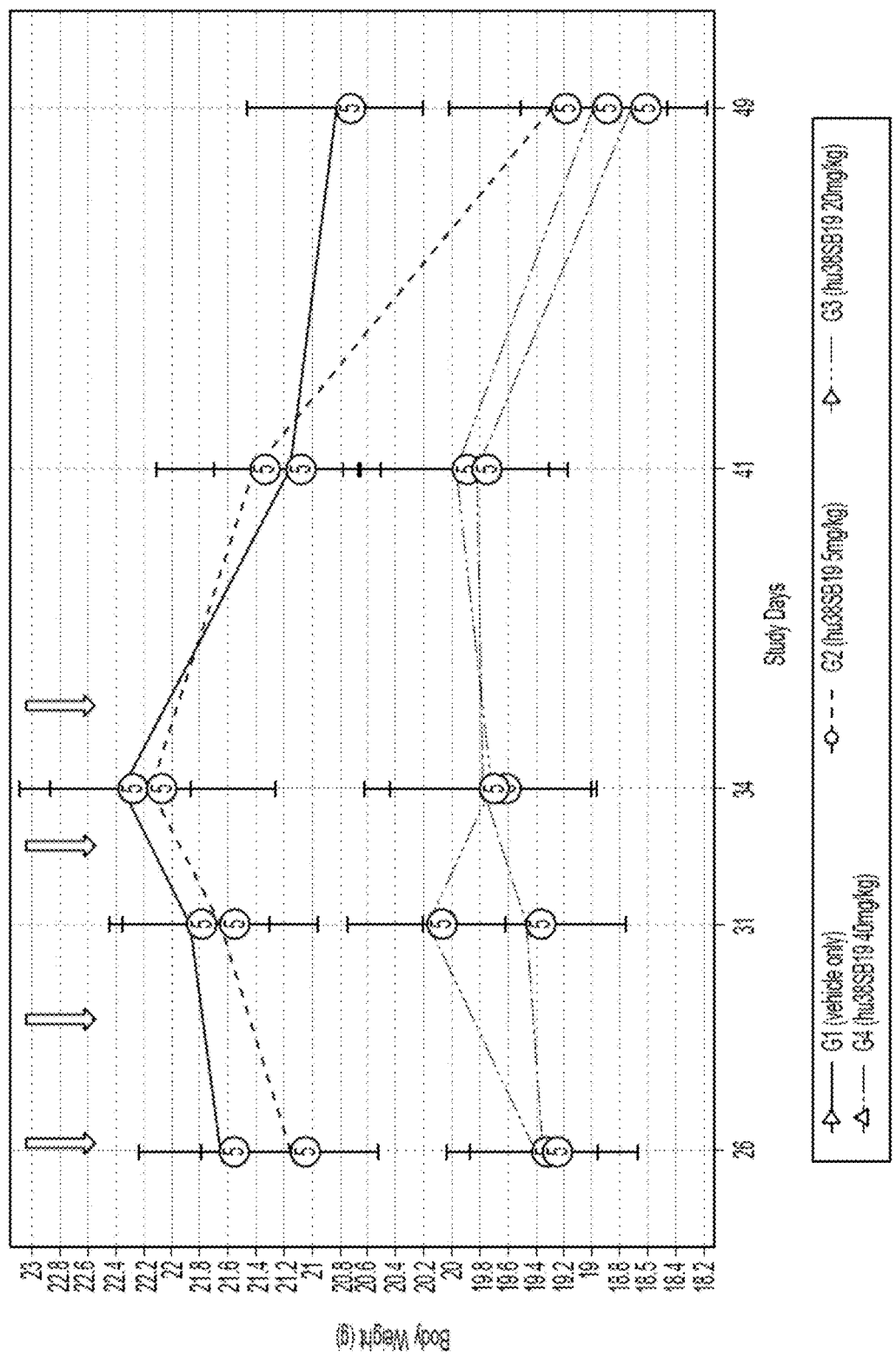
FIG. 5B shows the body weight of the H929 models after treatment with the indicated dose of hu38SB19 at the indicated times (arrows).
Figure 6A:
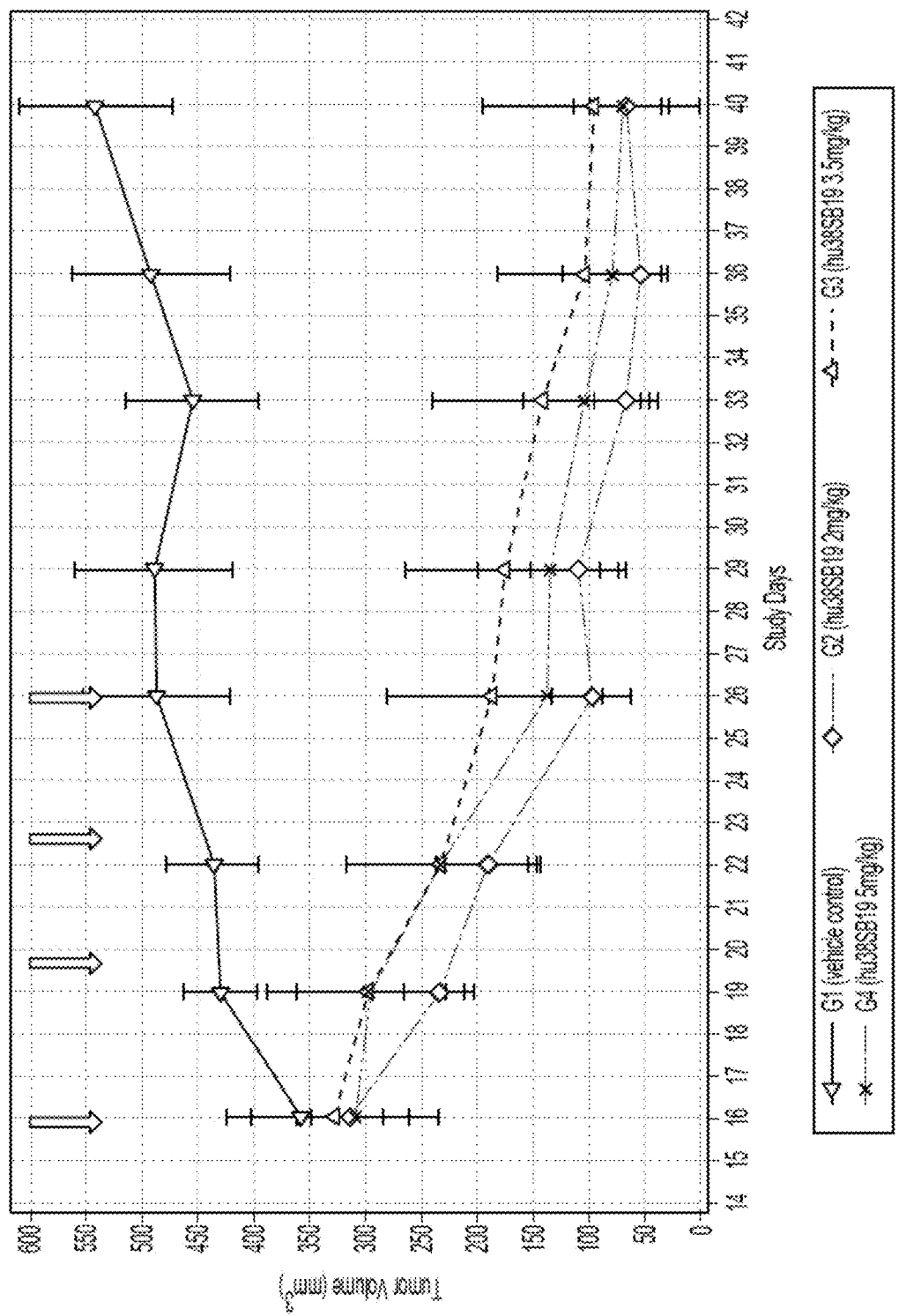
FIG. 6A shows the tumor volume of tumors in H929 models after treatment with the indicated dose of hu38SB19 at the indicated times (arrows).
Figure 7A:
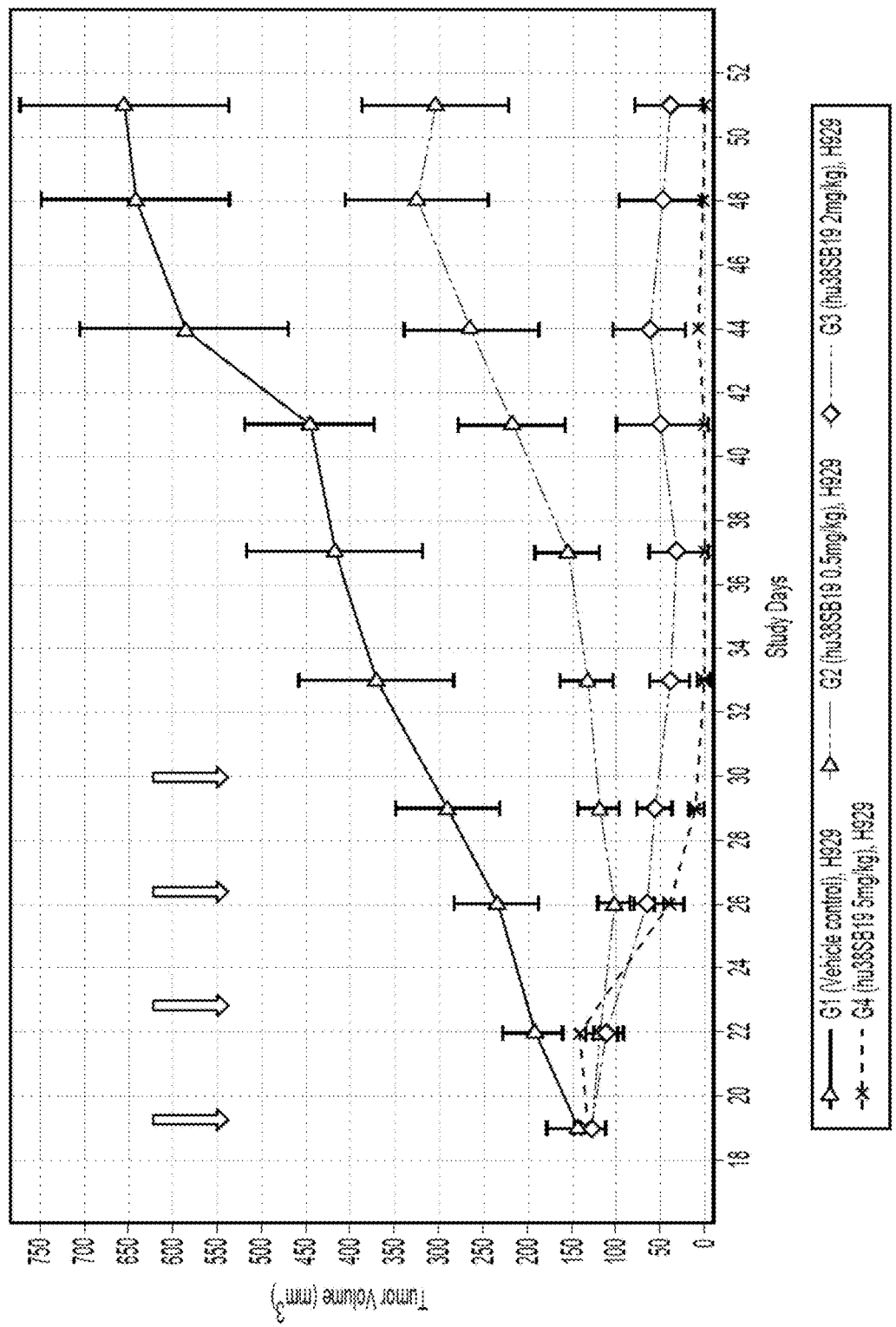
FIG. 7A shows the tumor volume of tumors in H929 models after treatment with the indicated dose of hu38SB19 at the indicated times (arrows).
Figure 7B:
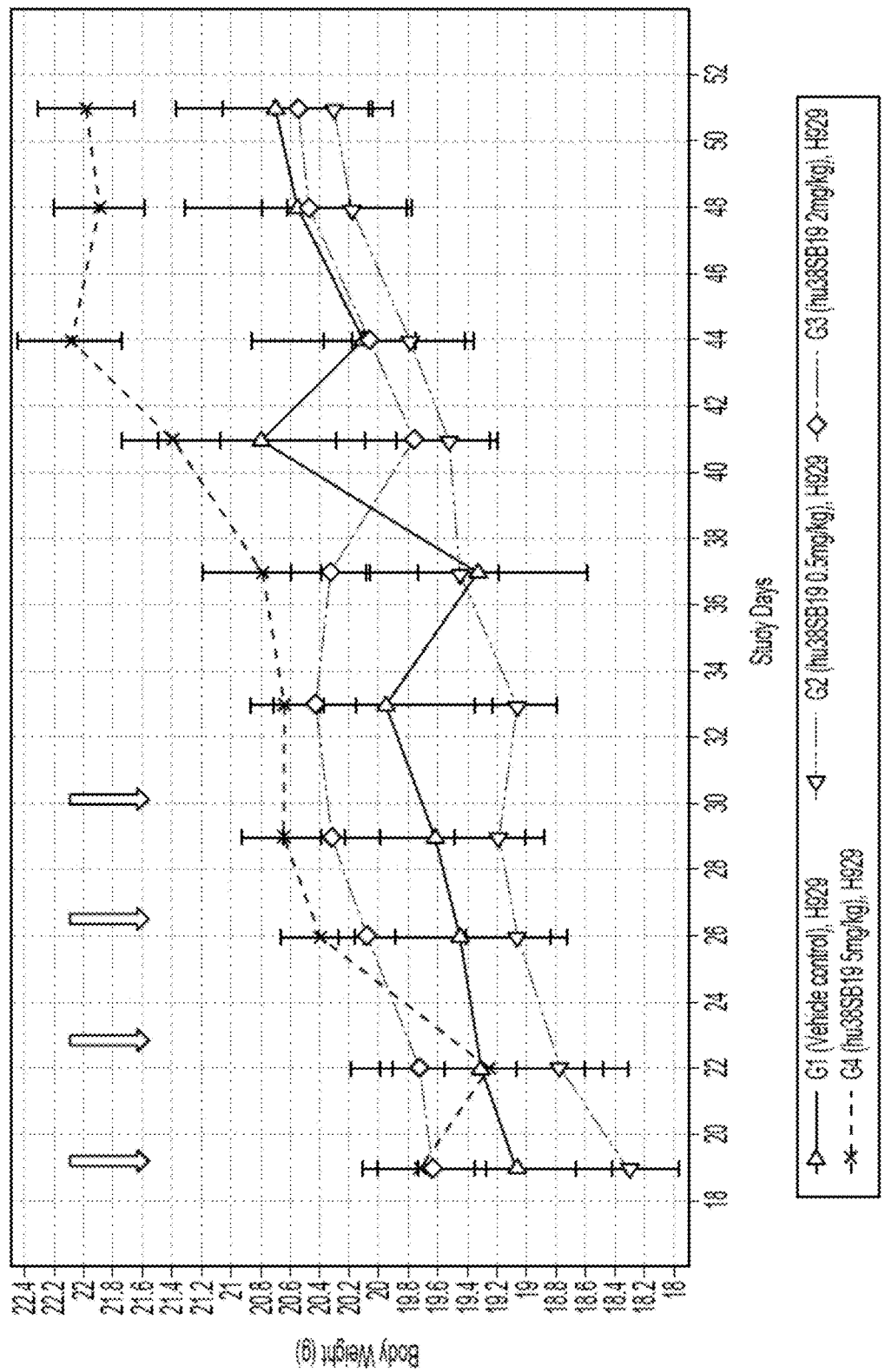
FIG. 7B shows the body weight of the H929 models after treatment with the indicated dose of hu38SB19 at the indicated times (arrows).
Figure 8A:
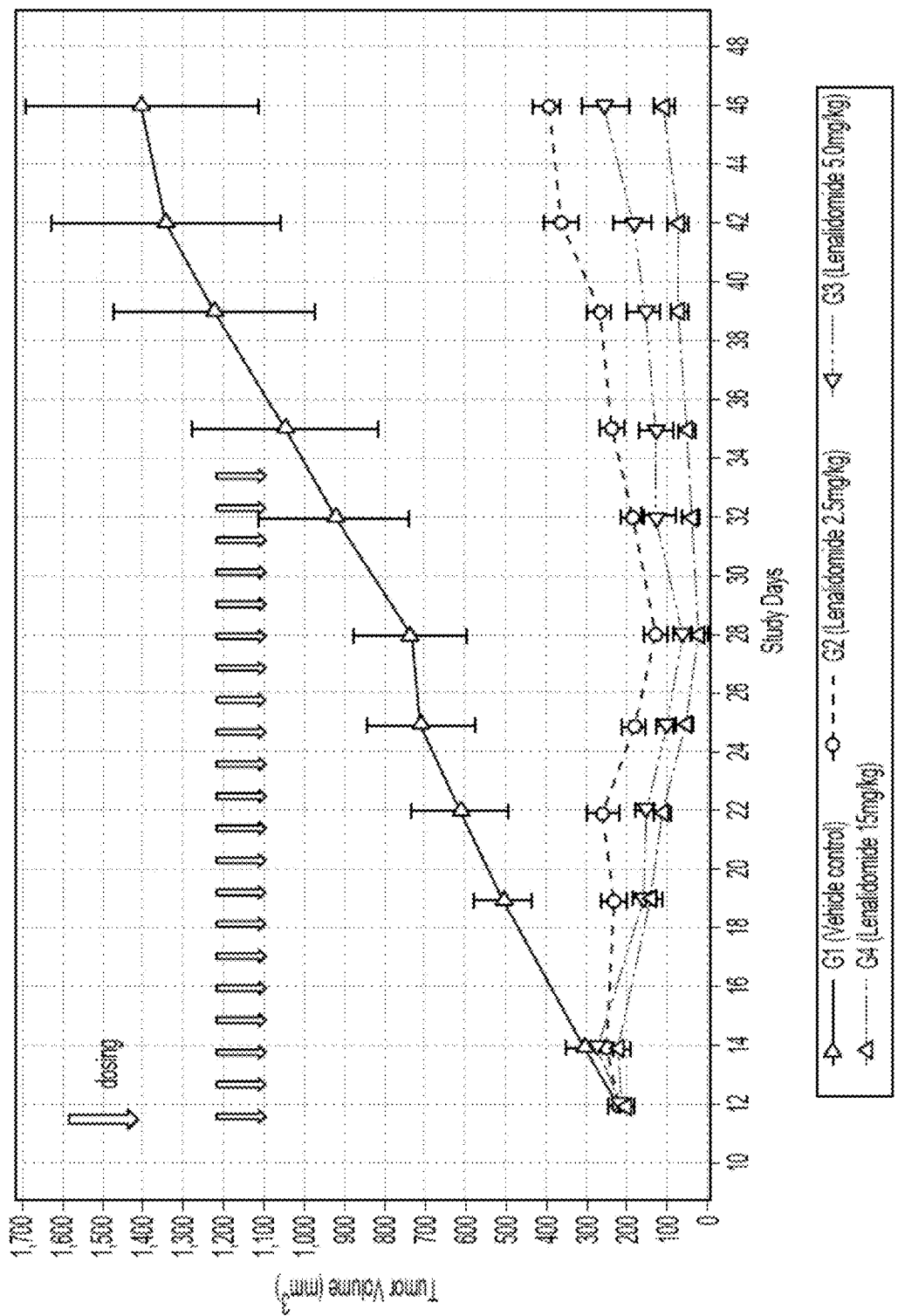
FIG. 8A shows the tumor volume of tumors in H929 models after treatment with the indicated dose of lenalidomide at the indicated times (arrows).
Figure 8B:
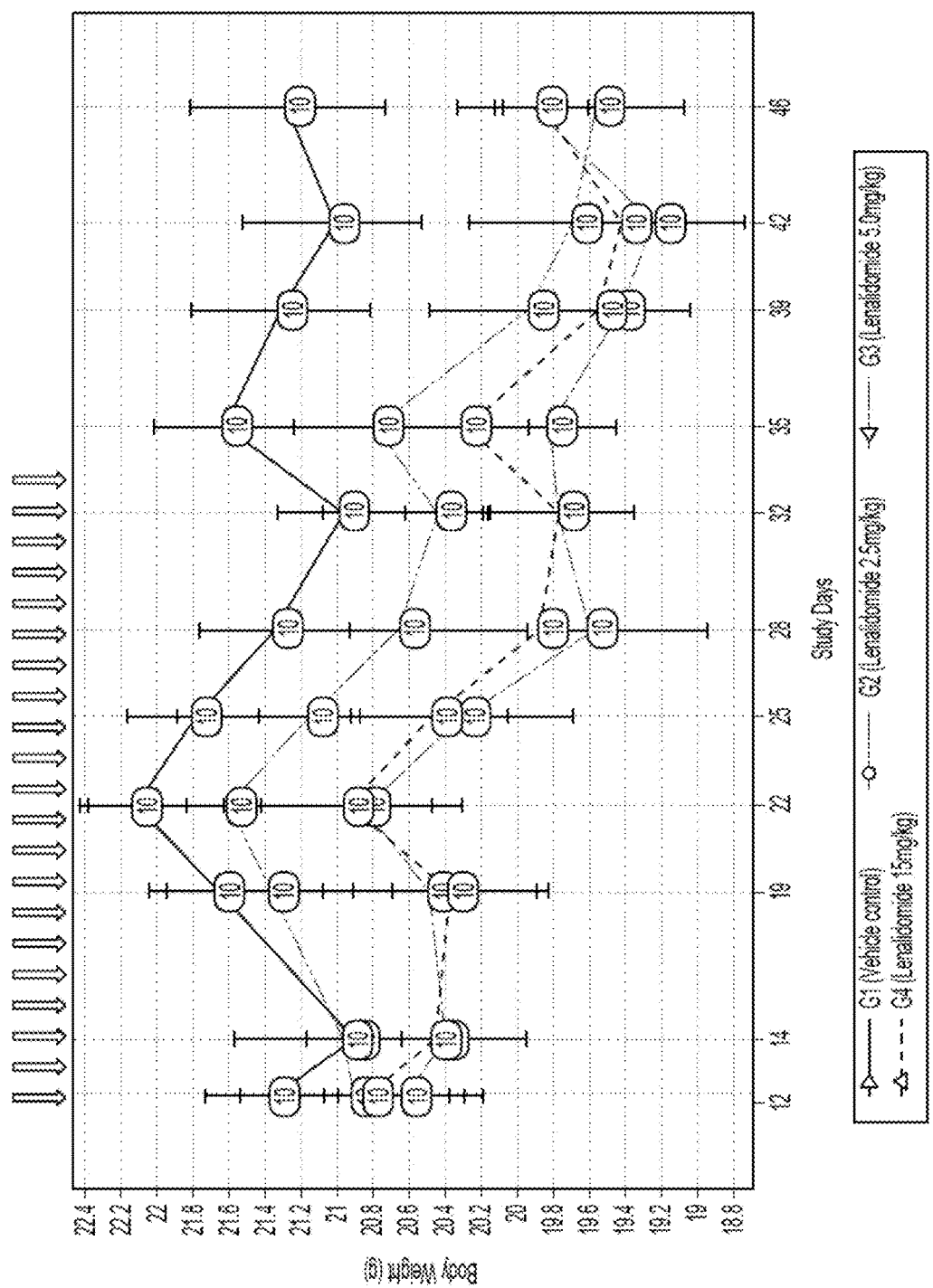
FIG. 8B shows the body weight of the H929 models after treatment with the indicated dose of lenalidomide at the indicated times (arrows).
Figure 9A:
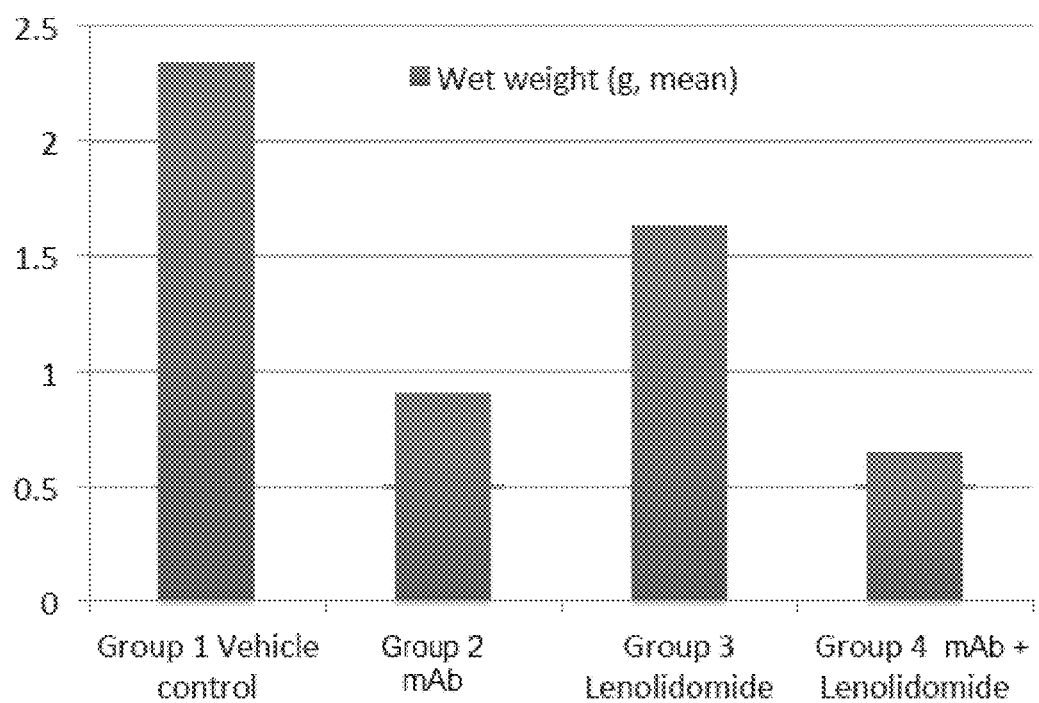
FIG. 9A is a graph showing the mean wet tumor weights of the RPMI8226 models after the indicated treatment with lenalidomide and/or hu38SB19 (mAb).
Figure 9B:
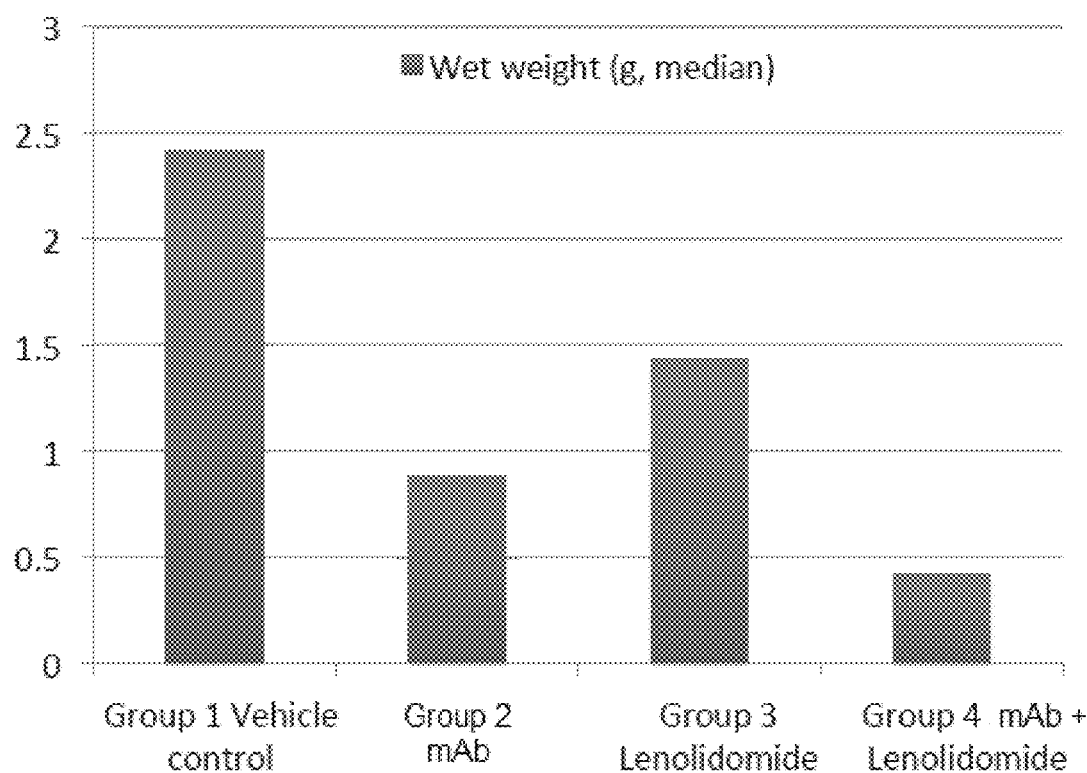
FIG. 9B is a graph showing the median wet tumor weights of the RPMI8226 models after the indicated treatment with lenalidomide and/or hu38SB19 (mAb).

In the RPMI-8226 model, hu38SB19 alone at 15 mg/kg/ injection (twice a week for 2 weeks) was inactive with a % $\Delta T/\Delta C$ of 44%. Treatment with lenalidomide alone at 15 mg/kg/day (dosed daily for three weeks) was inactive (61% $\Delta T/\Delta C$). The combination of hu38SB19 (15 mg/kg/injection) and lenalidomide (15 mg/kg/day) had higher activity with % T/C of 13% (FIG. 4). The results are summarized in Table 1.

TABLE 1

Anti-tumor efficacy of hu38SB19 in combination with lenalidomide against RPMI-8226 multiple myeloma model

| Agent | Dose in mg/kg (total dose) | Schedule of Administration IV or PO route | % $\Delta T/\Delta C$ (D69) | Activity |
|---|---|---|---|---|
| PBS | — | 2x/wk × 2 wk (IV) | | |
| hu38SB19 | 15 (60) | 2x/wk × 2 wk (IV) | 44 | Inactive |
| Lenalidomide | 15 (315) | QD × 21 d (PO) | 61 | Inactive |
| hu38SB19 + Lenalidomide | 15 (60) + 15 (315) | 2x/wk × 2 wk (IV) + QD × 21 d (PO) | 13 | Active |

Figure 10A:
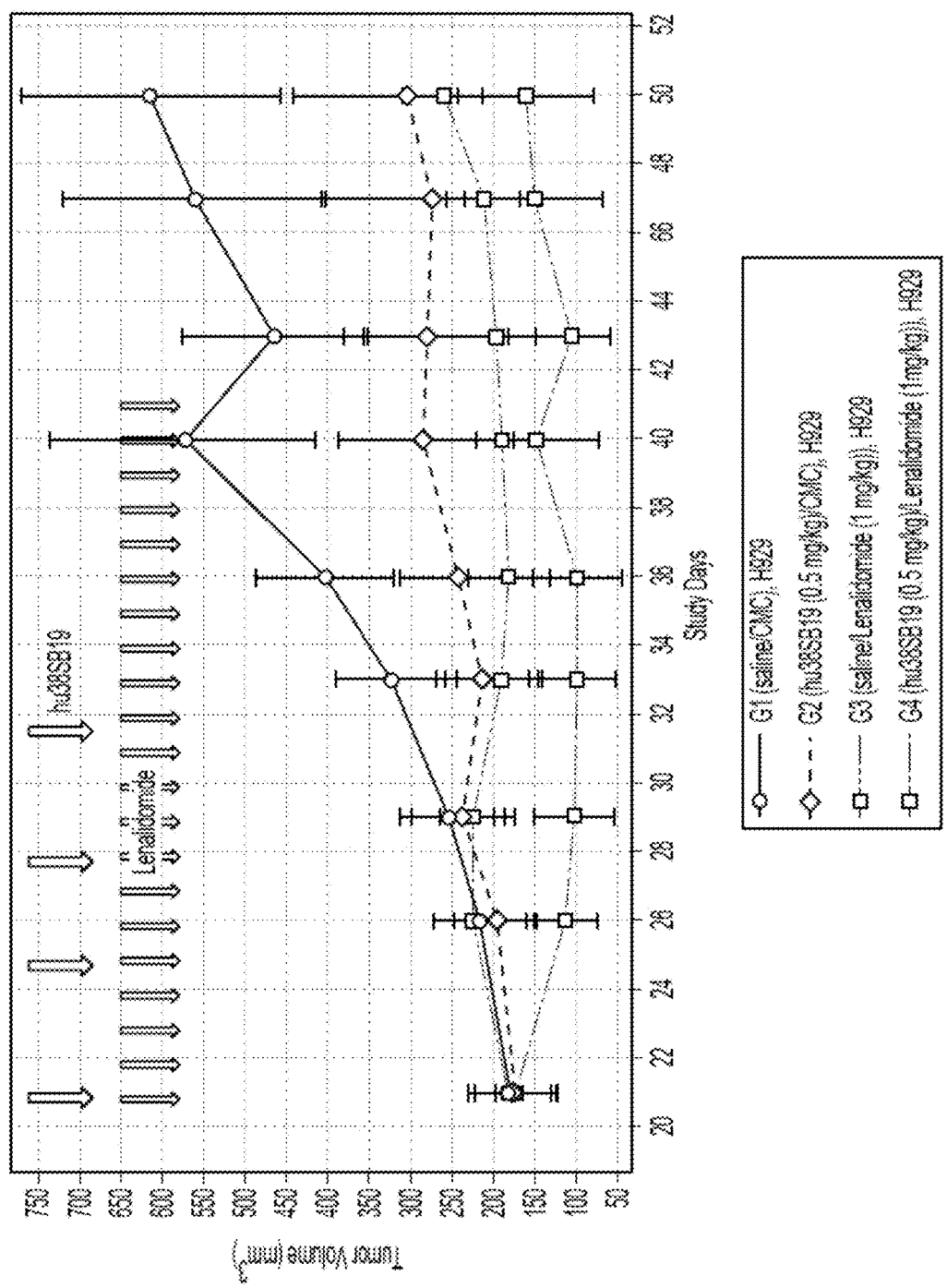
FIG. 10A shows the tumor volume of tumors in H929 models after treatment with the indicated dose of hu38SB19 at the indicated times (top arrows) and the indicated dose of lenalidomide at the indicated times (bottom arrows).
Figure 10B:
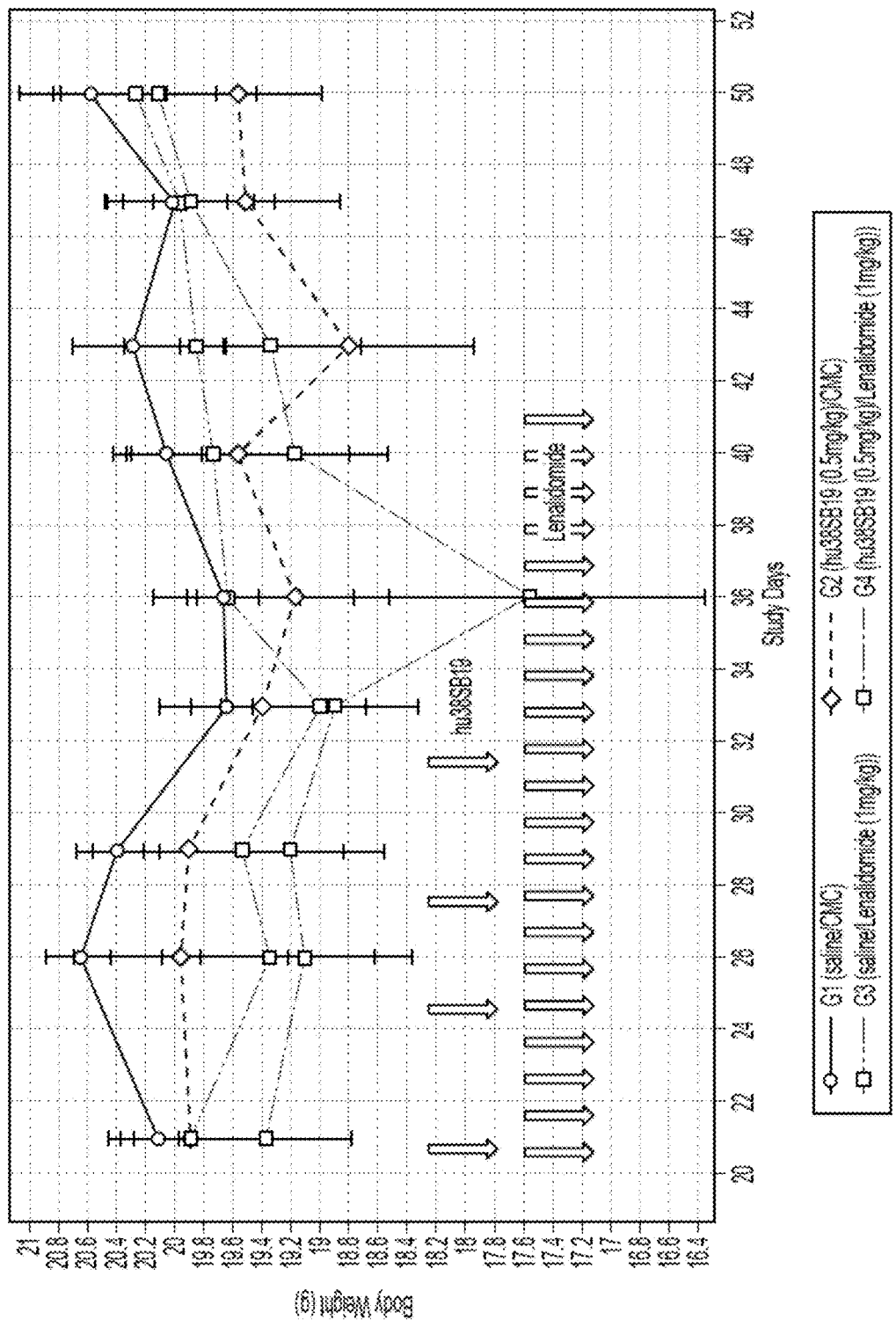
FIG. 10B shows the body weight of the H929 models after treatment with the indicated dose of hu38SB19 at the indicated times (top arrows) and the indicated dose of lenalidomide at the indicated times (bottom arrows).
Figure 11A:
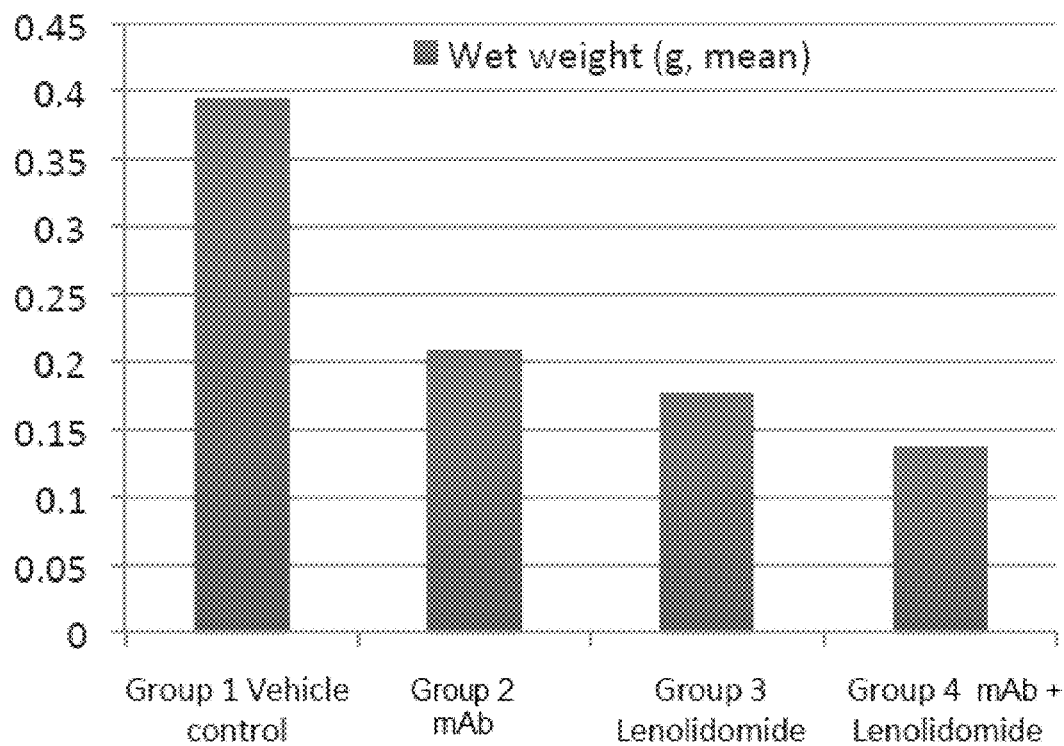
FIG. 11A is a graph showing the mean wet tumor weights of the H929 models after the indicated treatment with lenalidomide and/or hu38SB19 (mAb).
Figure 11B:
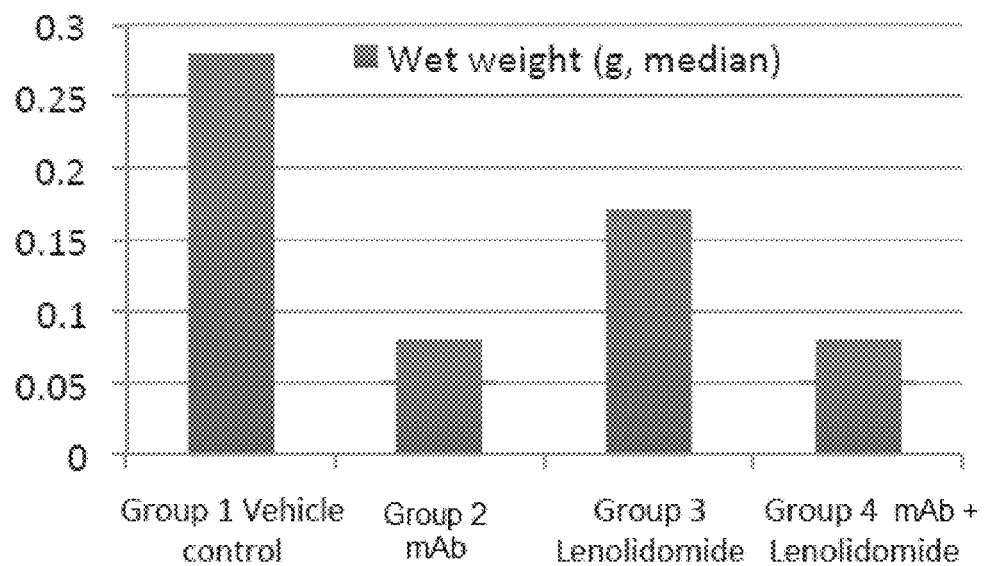
FIG. 11B is a graph showing the median wet tumor weights of the H929 models after the indicated treatment with lenalidomide and/or hu38SB19 (mAb).

% $\Delta T/\Delta C$ Median tumor volume change of the treated/Median tumor volume change of the control × 100, IV = intravenous, PO = oral, d = days, wk = week, QD = once daily, PBS: phosphate buffered saline In the NCI-H929 model, hu38SB19 alone at 0.5 mg/kg/ injection (twice a week for 2 weeks) was active with a % $\Delta T/\Delta C$ of 10%. Treatment with lenalidomide alone at 1 mg/kg/day (dosed daily for three weeks) was active (20% $\Delta T\Delta/C$). The combination of hu38SB19 (0.5 mg/kg/injection) and lenalidomide (1 mg/kg/day) had higher activity (tumor regression) with % $\Delta T/\Delta C$ of −8% (FIG. 10). The results are summarized in Table 2.

TABLE 2

Anti-tumor efficacy of hu38SB19 in combination with lenalidomide against NCI-H929 multiple myeloma model

| Agent | Dose in mg/kg (total dose) | Schedule of Administration IV or PO route | % $\Delta T/\Delta C$ (D69) | Activity |
|---|---|---|---|---|
| PBS | — | 2x/wk × 2 wk (IV) | | |
| hu38SB19 | 0.5 (2) | 2x/wk × 2 wk (IV) | 10 | Active |
| Lenalidomide | 1 (21) | QD × 21 d (PO) | 20 | Active |
| hu38SB19 + Lenalidomide | 0.5 (2) + 1 (21) | 2x/wk × 2 wk (IV) + QD × 21 d (PO) | −8 | Highly Active |

% $\Delta T/\Delta C$ Median tumor volume change of the treated/Median tumor volume change of the control × 100, IV = intravenous, PO = oral, d = days, wk = week, QD = once daily, PBS: phosphate buffered saline In both models, the combination treatment inhibited tumor growth to a much greater extent than a single agent alone, indicating the combination of hu38SB19 and lenalidomide blocked tumor cell growth through potential synergistic mechanisms. Although the molecular mechanisms of action of lenalidomide is still unknown, it is generally believed that lenalidomide enhances natural killer cell activity which is important for antibody dependent cellular cytotoxicity (ADCC) and directly induces apoptosis in tumor cells. Hu38SB19 has demonstrated potent ADCC and direct apoptosis induction activity on tumor cells and these activities are further enhanced by lenalidomide as evidenced by the experiments herein.

It has been reported that some CD38 antibodies such as Daratumumab is able to induce apoptosis only after cross-linking with a secondary antibody without much direct effect by itself. However, in preclinical studies, hu38SB19 demonstrated potent direct pro-apoptotic activity on tumor cells without cross-linking Thus, this unique property of hu38SB19 may also lead to greater tumor cell killing when in combination with lenalidomide compared to other CD38 antibodies combined with lenalidomide.

Example 2

Effect of the Administration of Both Anti-CD38 Antibody and Lenalidomide in Humans A Phase 1b study for evaluating the effects of a treatment with hu38SB19 combined with lenalidomide and low dose dexamethasone in patients with relapsed or refractory multiple myeloma is performed as described below.

The main goals of the Phase 1b study include:

To determine the efficacy and the maximum tolerated dose;

To evaluate the safety, including immunogenicity, of hu38SB19 in combination with lenalidomide in relapse or refractory multiple myeloma. The severity, frequency and incidence of all toxicities is assessed;

To evaluate the pharmacokinetics (PK) of hu38SB19 when administered in combination with lenalidomide and the PK of lenalidomide in combination with HU38SB19 and dexamethasone.

To assess the relationship between clinical (adverse event and/or tumor response) effects and pharmacologic parameters (PK/pharmacodynamics), and/or biologic (correlative laboratory) results;

Estimate the activity (response rate) using International Myeloma Working Group defined response criteria of hu38SB19 plus lenalidomide and dexamethasone; and To describe overall survival, progression free survival (PFS) and time to disease progression in patients treated with this combination.

About 20 to 40 patients may be selected based on the following criteria: The patients are male or female, but must be diagnosed with multiple myeloma and be aged of at least 18 years. For each patient, there is a documentation of at least 2 prior therapies (induction therapy is considered one prior therapy). There is no maximum number of prior regimens and prior bone marrow transplant is acceptable. There is a confirmed evidence of disease progression from immediately prior MM therapy or refractory to the immediately prior therapy. Patients may have received prior immunomodulatory drugs (IMiDs) (e.g., lenalidomide or thalidomide). Patients are with measurable disease. Patients are with a Karnofsky≥60% performance status. Females of childbearing potential are included provided they have a negative serum or urine pregnancy test with a sensitivity of at least 50 mIU/mL within 10 to 4 days and again within 24 hours prior to prescribing lenalidomide for Cycle 1 (prescriptions must be filled within 7 days as required by RevAssist®) and must either commit to continued abstinence from heterosexual intercourse or begin two acceptable methods of birth control, one highly effective method and one additional effective method at the same time, at least 28 days before she starts taking lenalidomide. Females of childbearing potential must also agree to ongoing pregnancy testing. Ability to understand the purpose and risks of the study and provide signed and dated informed consent and authorization to use protected health information (in accordance with national and local subject privacy regulations). The patient must be able to take aspirin daily as prophylactic anti-coagulation therapy (patients intolerant to aspirin may use warfarin, low molecular weight heparin or equivalent anti-platelet therapy).

In addition, patients meeting at least one of the following criteria are excluded:

Diagnosed or treated for another malignancy within 3 years prior to enrollment, with the exception of complete resection of basal cell carcinoma or squamous cell carcinoma of the skin, an in situ malignancy, or low risk prostate cancer after curative therapy;

Prior anti-cancer therapy (chemotherapy, targeted agents, radiotherapy, and immunotherapy) within 21 days except for alkylating agents (e.g., melphalan) where 28 days will be required or participated in another clinical trial during the past 30 days;

History of significant cardiovascular disease within the past 6 months, unless the disease is well-controlled. Significant cardiac diseases includes second/third degree heart block; significant ischemic heart disease (eg, angina); QTc interval>450 msec at baseline (read by local cardiologist); poorly controlled hypertension; congestive heart failure of New York Heart Association (NYHA) Class II (slight limitation of physical activity; comfortable at rest, but ordinary physical activity results in fatigue, palpitation, or dyspnea) or worse; left-ventricular ejection fraction (LVEF)<50%;

Prior peripheral stem cell transplant within 12 weeks of the first dose of study treatment;

Daily requirement for corticosteroids (>10 mg/kg prednisone qd) (except for inhalation corticosteroids);

Evidence of mucosal or internal bleeding;

Prior radiation therapy or major surgical procedure within 4 weeks of the first dose of study treatment;

Known active infection requiring parenteral or oral anti-infective treatment;

Serious psychiatric illness, active alcoholism, or drug addiction that may hinder or confuse follow-up evaluation;

Any medical conditions that, in the Investigator's opinion, would impose excessive risk to the patient. Examples of such conditions include any pre-existing kidney disease (acute or chronic, unless renal insufficiency is felt to be secondary to MM, hypertension, active seizure disorder or pulmonary diseases that would impose excessive risk to the patient;

Hypersensitivity to any of the components of study therapy that is not amenable to premedication with steroids and H2 blockers;

Known human immunodeficiency virus (HIV) or active hepatitis B or C viral infection;

Neuropathy≥Grade 3 or painful neuropathy≥Grade 2 (National Cancer Institute Common Terminology Criteria for Adverse Events [NCI CTCAE] v 4.0);

Gastro-intestinal abnormalities, including bowel obstruction, inability to take oral medication, requirement for intravenous (IV) alimentation, active peptic ulcer or prior surgical procedures or bowel resection affecting absorption; and Pregnancy.

The patients are treated with hu38SB19 combined with lenalidomide and dexamethasone. hu38SB19 is administered intravenously as a solution. Lenalidomide is administered orally as capsules. Dexamethasone is administered orally as tablets. The study duration for an individual patient includes a screening period for inclusion of up to 21 days, and at least 4 weeks of treatment in the absence of severe adverse reaction, dose limiting toxicity or disease progression plus up to 60 days post-treatment follow up. The total duration of the study may be up to one year.

The following parameters are measured during and/or at the end of the study:

Number of patients with adverse events when treated with hu38SB19 in combination with Lenalidomide Assessment of partial response, complete response, progression free survival, and survival;

Assessment of the following PK parameters: area under curve (AUC), maximum concentration (Cmax) and plasma half-life (T ½)

Number of CD38 receptors occupied by hu38SB19; and

Number of anti-SAR antibodies in response to hu38SB19.

Example 3

Efficacy of Anti-CD38 Antibody in In Vivo Tumor Models of Multiple Myeloma as a Single-Agent or in Combination with and Lenalidomide in Humans the Standard-of-Care Immunomodulatory Targeting Agent, Lenalidomide A. Materials and Methods CD38 Density: CD38 density was determined using anti-CD38-PE Quantibrite (BD Biosciences; Cat.342371) per the manufacturer's recommended protocols.

Reagents & Compounds: hu38SB19 was provided by Sanofi Oncology in solution at 5 mg/ml and stored at 4° C. hu38SB19 was diluted into sterile saline in preparation for dosing and used within 10 days of dilution. hu38SB19 was administered twice weekly×2 wk IV. Lenolidomide (TC27682) was obtained from AK Scientific Inc. (Mountain View, Calif.) and prepared as a suspension in 1% (w/v) carboxymethyl cellulose (Sigma). Preparation was made using a mortar and pestle to generate a slurry suspension in the vehicle, diluted to the appropriate concentration, and used for dosing by oral gavage. Lenalidomide was administered qdx7×3 wk PO.

Test Animals: 5-6 week old female Balb/c Scid mice were obtained from Jackson Lab. Mice were housed for 7-10 days prior to implantation of multiple myeloma (MM) cell lines. Mice were housed in a dedicated room in the UCSF Mt. Zion Animal Barrier Facility.

Cell culture: RPMI-8226 cells were obtained from the German Collection of Microorganisms and Cell Cultures, DSMZ, (Deutsche Sammlung von Mikroorganismen and Zellkulturen), and grown in sterile suspension culture in T225 flasks. RPMI-8226 were cultured in RPMI1640+10% FBS+4 mM L-glutamine.

Xenograft Model: At the time of implantation, mice were shaved on the right flank and shoulder. MM cells were suspended in serum free RPMI 1640 media diluted 1:1 with Matrigel (BD) at a concentration of $1×10^8$ cells per ml were injected sc into the right flank in 100 ul volume ($1×10^7$ cells) using a 1 ml syringe and 25 g needle. Mice were monitored twice weekly for the appearance of tumors and once tumors were visible, measurements were collected twice weekly for body weight and tumor volume. Electronic balance and calipers were used and data was collected directly into a study management program (Study Director). When the mean tumor volume reached approximately 150-200 $mm^3$, mice were distributed into treatment groups of 8-10 mice per group and dosing was initiated.

Figure 12:
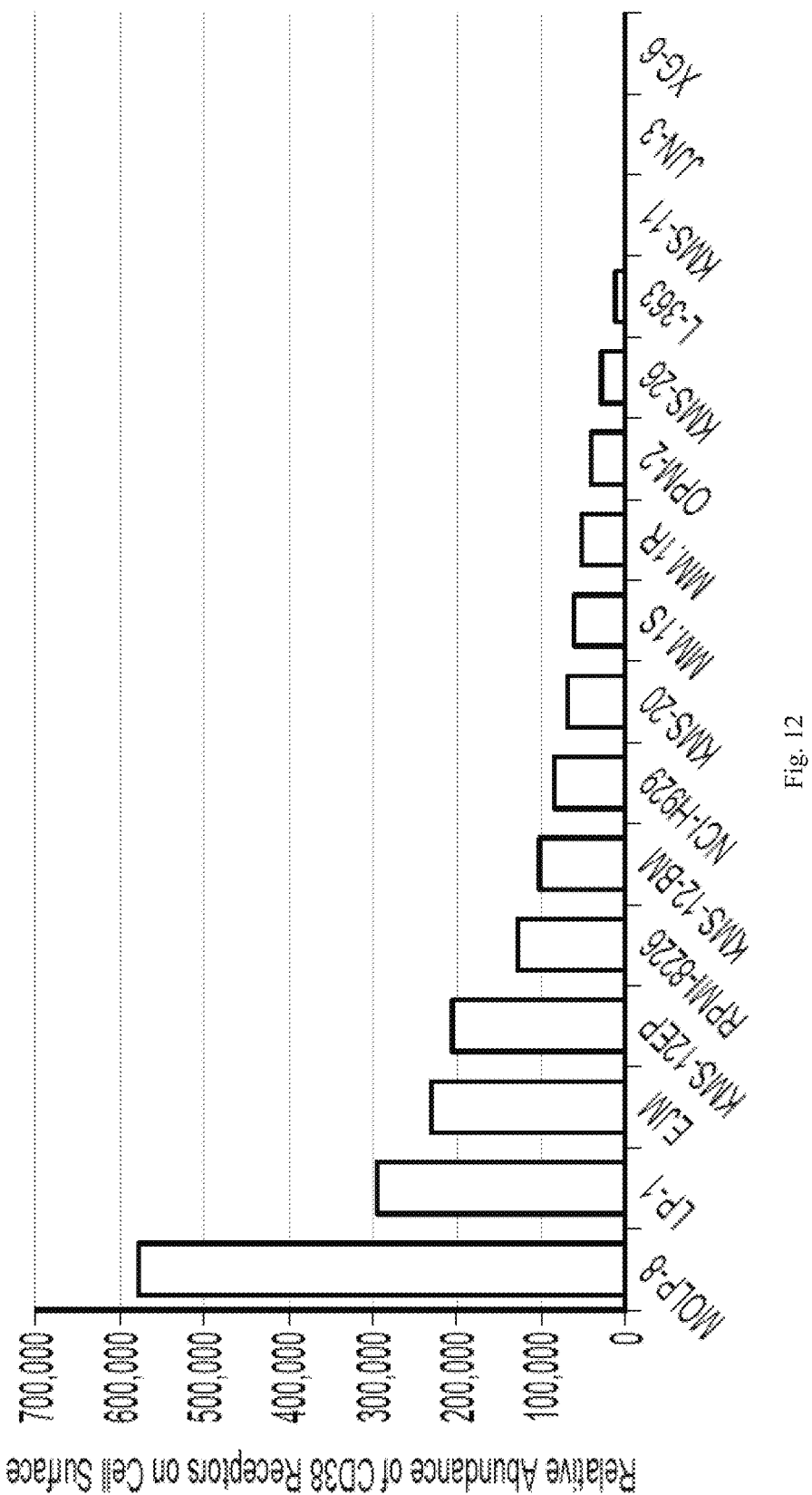
FIG. 12 is a graph showing the cell surface density of CD38 in multiple myeloma cell lines.
Figure 13:
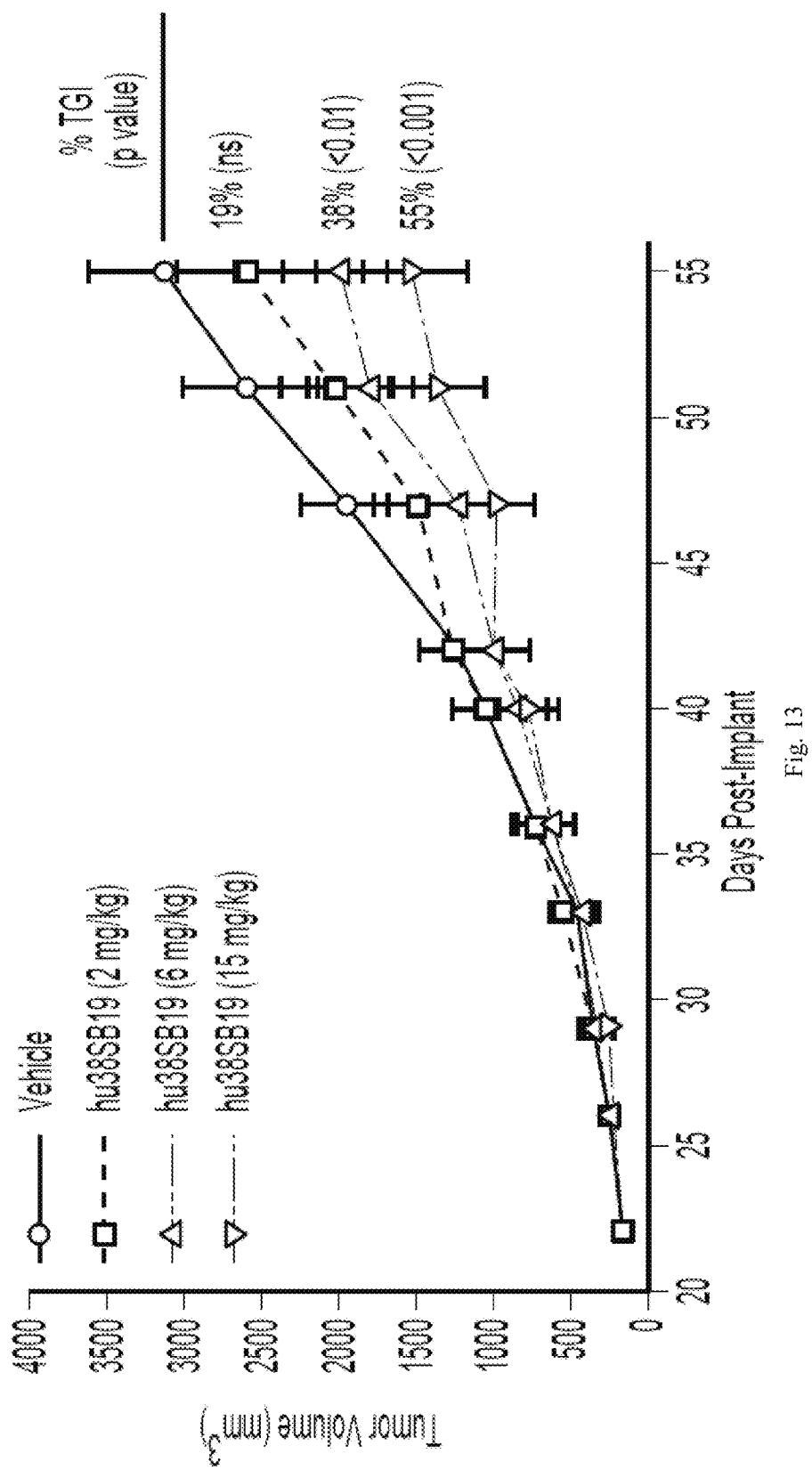
FIG. 13 is a graph showing that hu38SB19 inhibits RPMI-8226 tumor growth as a single-agent, i.e., as the sole active ingredient.
Figure 14:
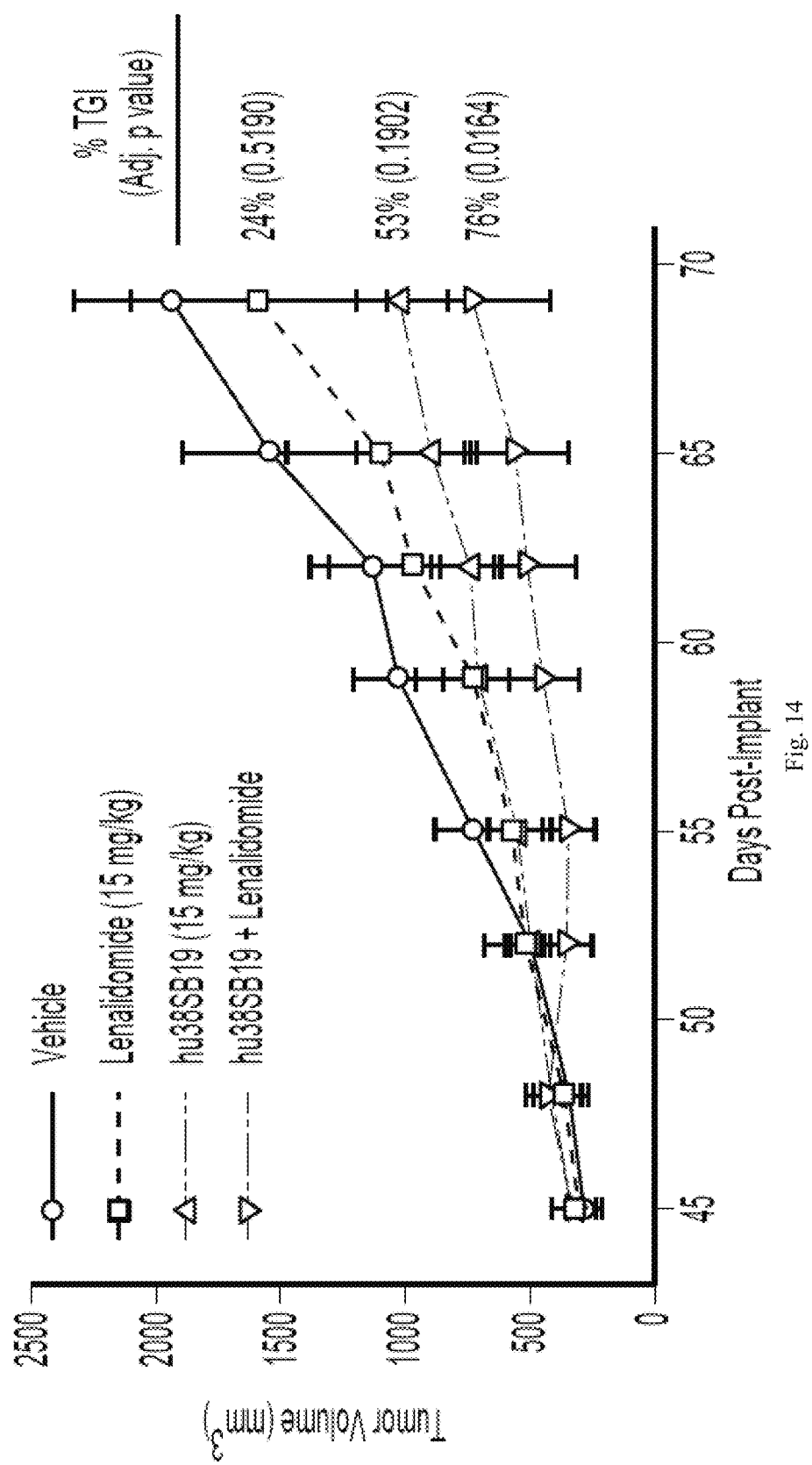
FIG. 14 is a graph showing that treatment with both hu38SB19 and lenalidomide inhibits growth of RPMI-8226 tumors.

B. Summary and Conclusions hu38SB19 is a humanized anti-CD38 antibody whose anti-myeloma effects incorporate mechanisms of ADCC, CDC, and direct apoptosis. FIG. 12 shows the cell surface density of CD38 in multiple myeloma cell lines. See Kim D, Park C Y, Medeiros B C, Weissman I L. CD19-CD45 low/-CD38 high/CD138+ plasma cells enrich for human tumorigenic myeloma cells. *Leukemia.* 2012 Dec., 26(12): 2530-7. CD38-positive multiple myeloma plasma cells demonstrate variable CD38 cell surface densities. All cell lines, with the exception of XG-6, are reported as CD38-positive. See Bataille R, Jego G, Robillard N, et al. The phenotype of normal, reactive and malignant plasma cells. Identification of "many and multiple myelomas" and of new targets for myeloma therapy. *Haematologica.* 2006 September, 91(9): 1234-40. Binding of hu38SB19 to CD38 also impinges on the ADPRC enzymatic activity of CD38. In vivo, hu38SB19 demonstrates potent anti-tumor effects in multiple myeloma xenografts, a disease largely characterized by neoplastic plasma cells expressing CD38. FIG. 13 shows that single-agent administration of hu38SB19 results in dose-dependent inhibition of tumor growth in an RPMI-8226 hind-flank model. The magnitude and significance of tumor growth inhibition at the end of the study increased with increased doses of hu38SB19. FIG. 14 shows that a combined regimen of hu38SB19 and Lenalidomide results in significant tumor growth inhibition in an RPMI-8226 xenograft model that is not robustly sensitive to single-agent therapy with Lenalidomide. These data demonstrate that single-agent hu38SB19 inhibits growth of RPMI-8226 tumors and combines with sub-efficacious doses of Lenalidomide to produce significant inhibition of tumor growth. Taken together, these data support further evaluation of hu38SB19, both as a single-agent and in combination with standard-of-care treatment regimens, as a potential therapy for the treatment of multiple myeloma.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating multiple myeloma in a subject comprising administering a therapeutically effective amount of an anti-CD38 antibody and a therapeutically effective amount of a lenalidomide compound to the subject,
   wherein the subject has undergone at least two prior therapies for multiple myeloma and at least one of the at least two prior therapies was lenalidomide,
   wherein the subject was refractory to lenalidomide, and
   wherein the anti-CD38 antibody comprises a heavy chain variable region of SEQ ID NO: 66, and a light chain variable region of SEQ ID NO: 62.

2. The method of claim 1, wherein the lenalidomide compound is lenalidomide.

3. The method of claim 1, wherein the anti-CD38 antibody is capable of killing a $CD38^+$ cell by apoptosis, antibody-dependent cell-mediated cytotoxicity (ADCC), and complement-dependent cytotoxicity (CDC).

4. The method of claim 1, wherein the anti-CD38 antibody is administered intravenously.

5. The method of claim 1, wherein the lenalidomide compound is administered orally.

6. The method of claim 1, wherein the anti-CD38 antibody and the lenalidomide compound are administered sequentially.

7. The method of claim 1, further comprising administering a dexamethasone compound to the subject.

8. The method of claim 7, wherein the dexamethasone compound is administered orally.

9. The method of claim 7, wherein the dexamethasone compound is administered at a low dose.

10. The method of claim 7, wherein the anti-CD38 antibody, the lenalidomide compound, and the dexamethasone compound are administered sequentially.

11. The method of claim 1, and further comprising administering an anti-coagulation agent to the subject.

12. The method of claim 11, wherein the anti-coagulation agent is selected from the group consisting of aspirin, warfarin, and low molecular weight heparin.

13. The method of claim 11, wherein the anti-CD38 antibody, the lenalidomide compound, and the anti-coagulation agent are administered sequentially.

14. The method of claim 1, wherein the subject has undergone at least three prior therapies for multiple myeloma.

* * * * *